(12) United States Patent
Miura et al.

(10) Patent No.: US 10,988,462 B2
(45) Date of Patent: Apr. 27, 2021

(54) PYRAZOLE COMPOUNDS SUBSTITUTED WITH HETEROARYL AND PHARMACEUTICAL USE THEREOF

(71) Applicant: Japan Tobacco Inc., Tokyo (JP)

(72) Inventors: Tomoya Miura, Osaka (JP); Shintaro Hirashima, Osaka (JP); Tomoyuki Manabe, Osaka (JP); Tetsuya Iida, Osaka (JP); Kentaro Sakurai, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/374,460

(22) Filed: Apr. 3, 2019

(65) Prior Publication Data

US 2019/0330193 A1 Oct. 31, 2019

(30) Foreign Application Priority Data

Apr. 4, 2018 (JP) .............................. JP2018-072557

(51) Int. Cl.
*C07D 403/14* (2006.01)
*C07D 401/14* (2006.01)

(52) U.S. Cl.
CPC ......... *C07D 403/14* (2013.01); *C07D 401/14* (2013.01)

(58) Field of Classification Search
CPC ........................... C07D 403/14; C07D 401/14
See application file for complete search history.

(56) References Cited

U.S. PATENT DOCUMENTS

| | | | |
|---|---|---|---|
| 5,420,141 A | 5/1995 | Boigegrain | |
| 5,624,941 A | 4/1997 | Barth | |
| 8,846,746 B2 * | 9/2014 | Miura .................. | C07D 403/14 514/407 |
| 2006/0128685 A1 | 6/2006 | Kanaya | |
| 2007/0219210 A1 | 9/2007 | Kanaya | |
| 2008/0027014 A1 | 1/2008 | Nomura | |
| 2013/0085132 A1 | 4/2013 | Miura | |
| 2016/0256440 A1 | 9/2016 | Short | |
| 2018/0346449 A1 | 12/2018 | Miura | |
| 2019/0352284 A1 | 11/2019 | Miura et al. | |

FOREIGN PATENT DOCUMENTS

| | | |
|---|---|---|
| AU | 2004200420 A1 | 9/2004 |
| EP | 1889842 A1 | 2/2008 |
| JP | H04247081 A | 9/1992 |
| JP | 2007332034 A | 12/2007 |
| JP | 2008007405 A | 1/2008 |
| JP | 2009544572 A | 12/2009 |
| WO | WO2004069824 A1 | 8/2004 |
| WO | WO2004089937 A1 | 10/2004 |
| WO | WO2004110351 A2 | 12/2004 |
| WO | WO2004110351 A3 | 4/2005 |
| WO | WO2005049578 A1 | 6/2005 |
| WO | WO2005063737 A1 | 7/2005 |
| WO | WO2006017055 A2 | 2/2006 |
| WO | WO2006054057 A2 | 5/2006 |
| WO | WO2006054057 A3 | 7/2006 |
| WO | WO2006017055 A3 | 8/2006 |
| WO | WO2007034279 A2 | 3/2007 |
| WO | WO2007098826 A2 | 9/2007 |
| WO | WO2007098826 A3 | 2/2008 |
| WO | WO2008061795 A2 | 5/2008 |
| WO | WO2008061796 A2 | 5/2008 |
| WO | WO2008061795 A3 | 7/2008 |
| WO | WO2008087529 A1 | 7/2008 |
| WO | WO2008061796 A3 | 7/2009 |
| WO | WO2009091813 A1 | 7/2009 |

(Continued)

OTHER PUBLICATIONS

International Search Report and Written Opinion dated Jun. 18, 2019 for PCT Application No. PCT/JP2019/014721 filed on Apr. 3, 2019, 8 pages. English Translation of ISR.
International Search Report and Written Opinion dated May 21, 2019 for PCT Application No. PCT/JP2019/007799 filed on Feb. 28, 2019, 9 pages. English Translation of ISR.
U.S. Appl. No. 16/289,500, filed Feb. 28, 2019. (Copy not submitted herewith persuant to the waiver of 37 C.F.R. § 1.98(a)(2)(iii) issued by the Office on Sep. 21, 2004).
U.S. Appl. No. 16/677,523, for Miura et al., filed Nov. 7, 2019. (Copy not submitted herewith pursuant to the waiver of 37 C.F.R. § 1.98(a)(2)(iii) issued by the Office on Sep. 21, 2004).
Written Opinion dated Jun. 18, 2019 for PCT Application No. PCT/JP2019/014721 filed Apr. 03, 2019, 4 pages. English Translation of WOISA.

(Continued)

*Primary Examiner* — Kamal A Saeed
(74) *Attorney, Agent, or Firm* — Morrison & Foerster LLP

(57) ABSTRACT

Pyrazole compounds substituted with heteroaryl or pharmaceutically acceptable salts thereof that have an SGLT1 inhibitory activity and are useful for a drug, pharmaceutical compositions comprising the same, and pharmaceutical use thereof are disclosed. Specifically, a compound of Formula [X]:

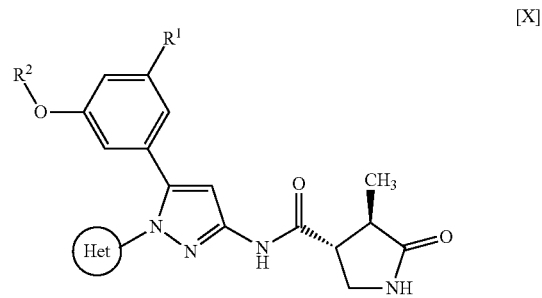

wherein $R^1$ is hydrogen or halogen, $R^2$ is $C_{1-6}$ alkyl or halo-$C_{1-6}$ alkyl, Ring Het is substituted pyridyl or optionally substituted pyrazinyl, pyrimidinyl, or pyridazinyl, or a pharmaceutically acceptable salt thereof, a pharmaceutical composition comprising it, and pharmaceutical use thereof is provided.

18 Claims, No Drawings

(56) References Cited

FOREIGN PATENT DOCUMENTS

| WO | WO2010007046 A2 | 1/2010 |
| WO | WO2010007046 A3 | 7/2010 |
| WO | WO2011126903 A2 | 10/2011 |
| WO | WO2011126903 A3 | 2/2012 |
| WO | WO2013031922 A1 | 3/2013 |

OTHER PUBLICATIONS

Written Opinion dated May 21, 2019 for PCT Application No. PCT/JP20191007799 filed Feb. 28, 2019, 5 pages. English Translation of WOISA.

* cited by examiner

PYRAZOLE COMPOUNDS SUBSTITUTED WITH HETEROARYL AND PHARMACEUTICAL USE THEREOF

CROSS REFERENCE TO RELATED APPLICATIONS

This application claims priority and benefit to Japanese Patent Application No. 2018-072557, filed Apr. 4, 2018, the disclosure of which is incorporated herein by reference in its entirety.

TECHNICAL FIELD

The present invention relates to pyrazole compounds substituted with heteroaryl or pharmaceutically acceptable salts thereof having an SGLT1 inhibitory activity, pharmaceutical compositions comprising the same, and pharmaceutical use thereof.

BACKGROUND ART

SGLT1, i.e., Sodium-Glucose Cotransporter 1, is known to contribute to a great portion of absorption of glucose and galactose in the small intestine. It is reported that human SGLT1-deficient patients cause glucose-galactose malabsorption. Furthermore, it is confirmed that the expression of SGLT1 in the small intestine increases in diabetic patients and it is thought that increased sugar absorption in diabetic patients is caused by the high expression of SGLT1 in the small intestine.

Based on the knowledge, an SGLT1 inhibitor is expected to normalize the blood glucose level by blocking glucose absorption in the small intestine. An SGLT1 inhibitor is, therefore, considered to be effective against diabetes and diabetic complications associated with hyperglycemia. It is also considered to be effective against obesity by inhibiting the inflow of glucose into the body (Non Patent Literatures 1 and 2).

Voglibose, a generic name, is a drug approved for manufacturing and marketing under the Japan Pharmaceutical Affairs Act Article 14 (Approval number: 21600AMZ00368). Voglibose improves excess blood glucose after eating by inhibiting disaccharidase, α-glucosidase, that degrades disaccharides existing in the intestinal mucosa into monosaccharides and inhibiting or delaying the digestion and absorption of carbohydrate in the intestinal tract. Such a pharmacological effect is known to be effective against delayed onset of type 2 diabetes in imparied glucose tolerance.

Based on the knowledge, inhibition of sugar absorption through small intestine with an SGLT1 inhibitor and thereby improvement of excess blood glucose after eating is thought to be effective against delayed onset of type 2 diabetes in imparied glucose tolerance.

The expression of SGLT1 is confirmed in cardiac muscle cells. It is known that GLUT1 (Glucose Transporter Type 1) and GLUT4 (Glucose Transporter Type 4) usually have a role in uptake of glucose into cardiac muscle cells and the contribution of SGLT1 is reduced. The expression of SGLT1 is, however, induced in the cardiac muscle of mice into which is introduced mutated genes of PRKAG2 (gamma 2 subunit of AMPK (AMP-Activated Protein Kinase)) which is a responsible gene of familial hypertrophic cardiomyopathy (glycogen accumulation-type myocardosis), or mice which undergo myocardial ischemia treatment, and SGLT1 is reported to contribute to the uptake of glucose to cardiac muscle cells in these pathologies. Glucose incorporated by SGLT1 is thought to be excessively accumulated or metabolized within cardiac muscle cells and impair the cells. It is reported in the former mouse model that accumulation of glycogen in the cardiac muscle is actually inhibited by the treatment of a non-selective SGLT inhibitor, phlorizin.

Based on the knowledge, an SGLT1 inhibitor is thought to be effective against hypertrophic cardiomyopathy and ischemic heart disease by inhibiting uptake of excess glucose into cardiac muscle cells (Non Patent Literatures 3 and 4).

SGLT1 is stabilized in cancer cells by epidermal growth factor receptors, i.e., surface proteins on many kinds of cancer cells. It is known that transporters of glucose, lactic acid, and amino acid, etc. are involved in nutrition supply to cancer cells, and especially, regarding the transportation of glucose, SGLT1 and GLUT1 continuously supply glucose to cancer cells. When glucose is not supplied over a long period of time, cells are destroyed by autophagy.

Based on the knowledge, an SGLT1 inhibitor is thought to inhibit supply of glucose to cancer cells and show anticancer activity (Non Patent Literatures 5 and 6).

Since carbohydrate is degraded to monosaccharides in the gastrointestinal tract in diet and is absorbed in the upper gastrointestinal tract, many sugars never reach the lower gastrointestinal tract. When, however, drugs that delay or inhibit glucose absorption are administered, or a large amount of resistant polysaccharides are ingested, then undigested sugars are retained in the lower gastrointestinal tract and the undigested sugars retained in the lower gastrointestinal tract cause osmotic diarrhea.

An SGLT1 inhibitor inhibits the glucose absorption and increases the amount of monosaccharides in the lower gastrointestinal tract. The SGLT1 inhibitor is, therefore, believed to be effective against constipation.

Non Patent Literatures

[Non Patent Literature 1] Am J Physiol Gastrointest Liver Physiol. 2002; 282(2):G241-8

[Non Patent Literature 2] Nature. 1991; 350(6316):354-6

[Non Patent Literature 3] J Mol Cell Cardiol. 2010; 49(4): 683-92

[Non Patent Literature 4] Cardiovasc Res. 2009; 84(1):111-8

[Non Patent Literature 5] Cancer Cell. 2008, 13: 385-93

[Non Patent Literature 6] Pharmacol Ther. 2009, 121: 29-40

SUMMARY OF INVENTION

Pyrazole compounds substituted with heteroaryl that have an SGLT1 inhibitory activity and are useful for a drug or pharmaceutically acceptable salts thereof; pharmaceutical compositions comprising the same; and pharmaceutical use thereof are provided.

After extensive studies, the present inventors found specific pyrazole compounds substituted with heteroaryl and achieved the present invention.

In one embodiment, a compound of Formula [X]:

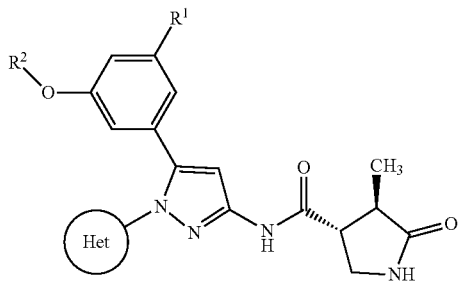
[X]

wherein $R^1$ is hydrogen or halogen;
$R^2$ is $C_{1-6}$ alkyl or halo-$C_{1-6}$ alkyl;
Ring Het is:
(1) pyridyl substituted with $R^3$; or
(2) pyrazinyl, pyrimidinyl, or pyridazinyl, optionally substituted with $R^4$;
$R^3$ is cyano, halogen, or halo-$C_{13}$ alkyl;
$R^4$ is halogen, hydroxy, $C_{1-3}$ alkyl, halo-$C_{13}$ alkyl, $C_{1-3}$ alkoxy, or —N($R^5$)($R^6$); and
$R^5$ and $R^6$ are each independently hydrogen or $C_{1-3}$ alkyl, or a pharmaceutically acceptable salt thereof, and pharmaceutical use thereof are provided.

In another embodiment, a compound of Formula [I] or a pharmaceutically acceptable salt thereof and pharmaceutical use thereof are provided.

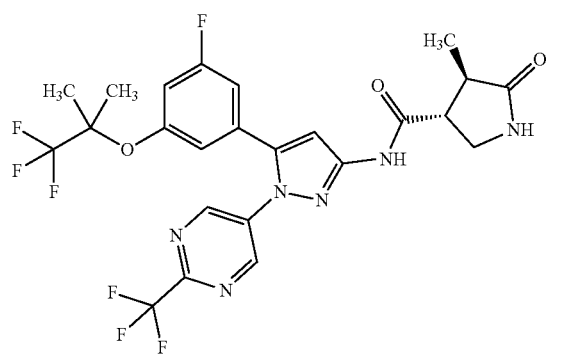
[I]

In another embodiment, a compound of Formula [II] or a pharmaceutically acceptable salt thereof and pharmaceutical use thereof are provided.

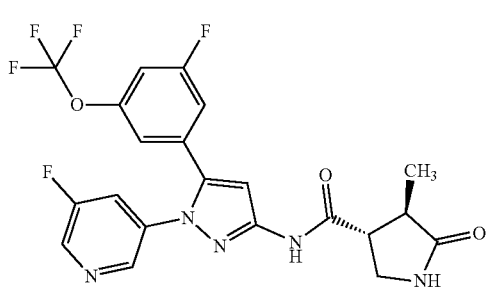
[II]

In another embodiment, a compound of Formula [III] or a pharmaceutically acceptable salt thereof and pharmaceutical use thereof are provided.

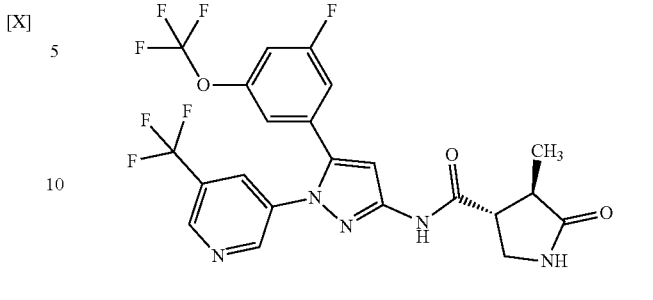
[III]

In another embodiment, a compound of Formula [IV] or a pharmaceutically acceptable salt thereof and pharmaceutical use thereof are provided.

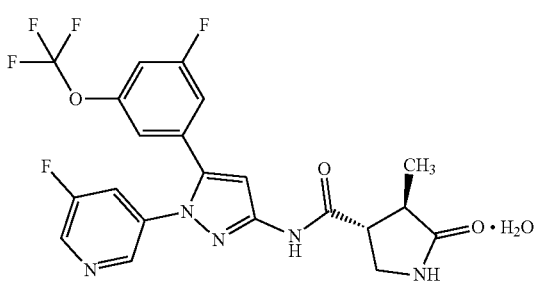
[IV]

DESCRIPTION OF EMBODIMENTS

The present invention includes the embodiments illustrated as follows.
Item 1. A compound of Formula [X]:

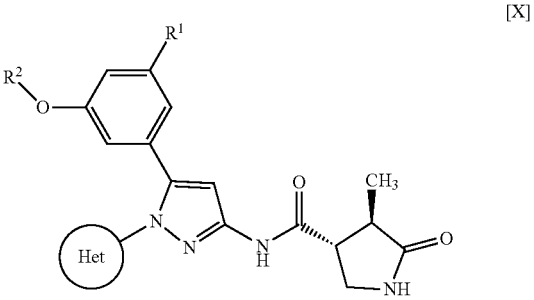
[X]

wherein $R^1$ is hydrogen or halogen;
$R^2$ is $C_{1-6}$ alkyl or halo-$C_1$ 6 alkyl;
Ring Het is:
(1) pyridyl substituted with $R^3$; or
(2) pyrazinyl, pyrimidinyl, or pyridazinyl, optionally substituted with $R^4$;
$R^3$ is cyano, halogen, or halo-$C_1$ 3 alkyl;
$R^4$ is halogen, hydroxy, $C_1$ 3 alkyl, halo-$C_1$ 3 alkyl, $C_{1-3}$ alkoxy, or —N($R^5$)($R^6$); and
$R^5$ and $R^6$ are each independently hydrogen or $C_{1-3}$ alkyl, or a pharmaceutically acceptable salt thereof.
Item 2. The compound or pharmaceutically acceptable salt thereof according to Item 1, wherein $R^1$ is halogen.

Item 3. The compound or pharmaceutically acceptable salt thereof according to either Item 1 or 2, wherein $R^2$ is halo-$C_{1-6}$ alkyl.

Item 4. The compound or pharmaceutically acceptable salt thereof according to any one of Items 1 to 3, wherein Ring Het is pyridyl substituted with $R^3$.

Item 5. The compound or pharmaceutically acceptable salt thereof according to any one of Items 1 to 3, wherein Ring Het is pyrazinyl, pyrimidinyl, or pyridazinyl, optionally substituted with $R^4$.

Item 6. A compound of Formula [I]:

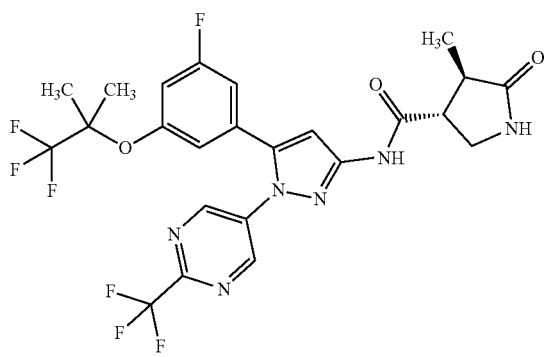

or a pharmaceutically acceptable salt thereof.

Item 7. A compound of Formula [II]:

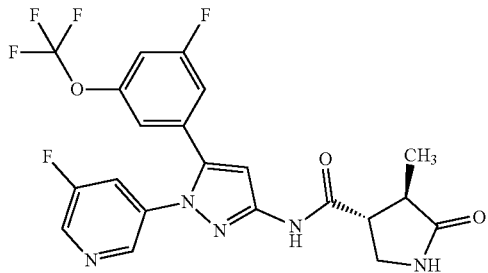

or a pharmaceutically acceptable salt thereof.

Item 8. A compound of Formula [III]:

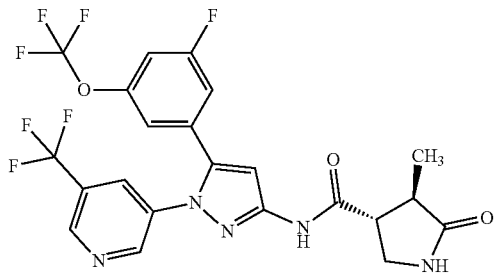

or a pharmaceutically acceptable salt thereof.

Item 9. A compound of Formula [IV]:

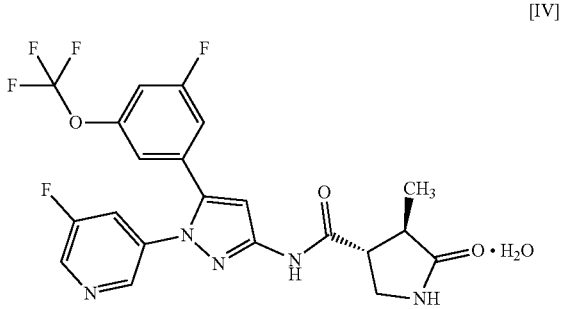 [SMILES: C[C@H]1C(=O)NC[C@@H]1C(=O)Nc1cc(-c2cc(F)cc(OC(F)(F)F)c2)n(-c2cncc(F)c2)n1]

or a pharmaceutically acceptable salt thereof.

Item 10. A pharmaceutical composition comprising the compound or pharmaceutically acceptable salt thereof according to any one of Items 1 to 9 and a pharmaceutically acceptable carrier.

Item 11. An SGLT1 inhibitor comprising the compound or pharmaceutically acceptable salt thereof according to any one of Items 1 to 9.

Item 12. A therapeutic or preventive agent for diabetes comprising the compound or pharmaceutically acceptable salt thereof according to any one of Items 1 to 9.

Item 13. The therapeutic or preventive agent according to Item 12, wherein the diabetes is type 2 diabetes.

Item 14. A method for inhibiting SGLT1 comprising administering a therapeutically effective amount of the compound or pharmaceutically acceptable salt thereof according to any one of Items 1 to 9 to a mammal.

Item 15. A method for treating or preventing diabetes comprising administering a therapeutically effective amount of the compound or pharmaceutically acceptable salt thereof according to any one of Items 1 to 9 to a mammal.

Item 16. The method according to Item 15, wherein the diabetes is type 2 diabetes.

Item 17. Use of the compound or pharmaceutically acceptable salt thereof according to any one of Items 1 to 9 for the manufacture of an SGLT1 inhibitor.

Item 18. Use of the compound or pharmaceutically acceptable salt thereof according to any one of Items 1 to 9 for the manufacture of a therapeutic or preventive agent for diabetes.

Item 19. The use according to Item 18, wherein the diabetes is type 2 diabetes.

Item 20. The compound or pharmaceutically acceptable salt thereof according to any one of Items 1 to 9 for use in inhibiting SGLT1.

Item 21. The compound or pharmaceutically acceptable salt thereof according to any one of Items 1 to 9 for use in treating or preventing diabetes.

Item 22. The compound or pharmaceutically acceptable salt thereof according to Item 21, wherein the diabetes is type 2 diabetes.

Item 23. A commercial package comprising the composition according to Item 10 and a written matter associated therewith, the written matter indicating that the composition may or should be used for the treatment or prevention of diabetes.

Item 24. A kit comprising the composition according to Item 10 and a written matter associated therewith, the written matter indicating that the composition may or should be used for the treatment and/or prevention of diabetes.

A double wavy line as follows:

in a partial structure shows a binding site of the structure.

The term "halogen" includes fluoro, chloro, bromo, and iodo.

The term "$C_{1-3}$ alkyl" means a straight- or branched-chain saturated hydrocarbon group with 1 to 3 carbon atoms. The "$C_{1-3}$ alkyl" group includes methyl, ethyl, n-propyl, and isopropyl.

The term "$C_{1-6}$ alkyl" means a straight- or branched-chain saturated hydrocarbon group with 1 to 6 carbon atoms. The "$C_{1-6}$ alkyl" group includes, for example, methyl, ethyl, n-propyl, isopropyl, n-butyl, isobutyl, sec-butyl, tert-butyl, n-pentyl, isopentyl, and n-hexyl.

The term "halo-$C_{1-3}$ alkyl" means the "$C_{1-3}$ alkyl" group substituted with 1 to 5 halogen atoms independently selected from the group of the term "halogen". The "halo-$C_{1-3}$ alkyl" group includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, and 3,3,3-trifluoropropyl.

The term "fluoro-$C_{1-3}$ alkyl" means the "$C_{1-3}$ alkyl" group substituted with 1 to 5 fluoro atoms. The "fluoro-$C_{13}$ alkyl" group includes, for example, monofluoromethyl, difluoromethyl, trifluoromethyl, 2-fluoroethyl, 1,1-difluoroethyl, 2,2,2-trifluoroethyl, pentafluoroethyl, 3-fluoropropyl, 1,1-difluoropropyl, and 3,3,3-trifluoropropyl.

The term "halo-$C_{1-6}$ alkyl" means the "$C_{1-6}$ alkyl" group substituted with 1 to 5 halogen atoms independently selected from the group of the term "halogen". The "halo-$C_{1-6}$ alkyl" group includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, 3,3,3-trifluoropropyl, 4,4,4-trifluorobutyl, 5,5,5-trifluoropentyl, and 6,6,6-trifluorohexyl.

The term "fluoro-$C_{1-6}$ alkyl" means the "$C_{1-6}$ alkyl" group substituted with 1 to 5 fluoro atoms. The "fluoro-$C_{1-6}$ alkyl" group includes, for example, monofluoromethyl, difluoromethyl, trifluoromethyl, 2-fluoroethyl, 1,1-difluoroethyl, 2,2,2-trifluoroethyl, pentafluoroethyl, 3-fluoropropyl, 1,1-difluoropropyl, 3,3,3-trifluoropropyl, 4,4,4-trifluorobutyl, 5,5,5-trifluoropentyl, and 6,6,6-trifluorohexyl.

The term "$C_{1-3}$ alkoxy" means a group wherein the "$C_{1-3}$ alkyl" group binds to an oxygen atom. The "$C_{1-3}$ alkoxy" group includes methoxy, ethoxy, n-propoxy, and isopropoxy.

The term "pyridyl" means any one of the following groups:

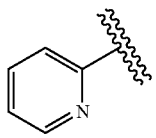

[P1-1]

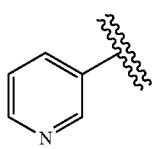

[P1-2]

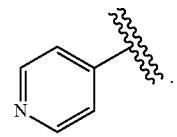

[P1-3]

The term "pyrazinyl" means the following group:

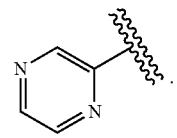

[P2-1]

The term "pyrimidinyl" means any one of the following groups:

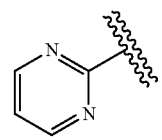

[P3-1]

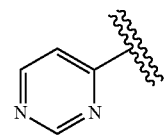

[P3-2]

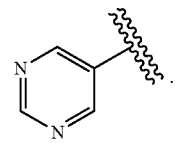

[P3-3]

The term "pyridazinyl" means any one of the following groups:

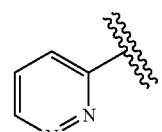

[P4-1]

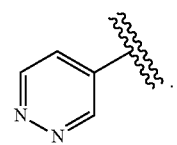

[P4-2]

The term "substituted" includes any chemically acceptable substitutions. For example, the phrase "pyridyl substituted with $R^3$" means any one of the following groups:

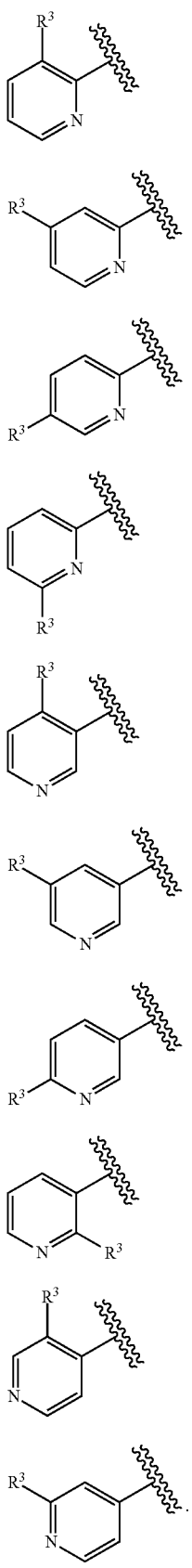

Embodiments of each substituent of a compound of Formula [X] are illustrated as below, but each substituent of a compound of Formula [X] is not limited to those embodiments. A compound of Formula [X] includes any combinations of two or more embodiments and elements optionally selected from the embodiments and elements in each substituent.

In one embodiment, $R^1$ is hydrogen or fluoro. In another embodiment, $R^1$ is fluoro.

In one embodiment, $R^2$ is halo-$C_{1-6}$ alkyl. In another embodiment, $R^2$ is fluoro-$C_{1-6}$ alkyl.

In one embodiment, Ring Het is:
(1) pyridyl substituted with $R^3$; or
(2) pyrazinyl or pyrimidinyl, optionally substituted with $R^4$.

In another embodiment, Ring Het is selected from the group consisting of Formulae [H1] to [H14].

In still another embodiment, Ring Het is selected from the group consisting of Formulae [H2], [H3], [H5], [H8] to [H12], and [H14].

In still another embodiment, Ring Het is Formula [H2] or [H8].

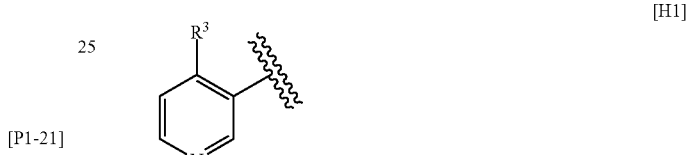

[H1]

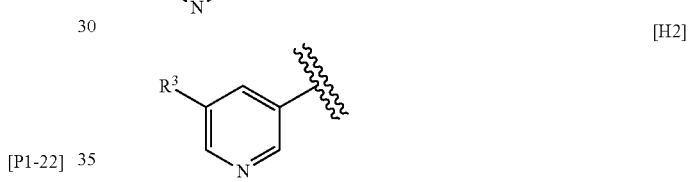

[H2]

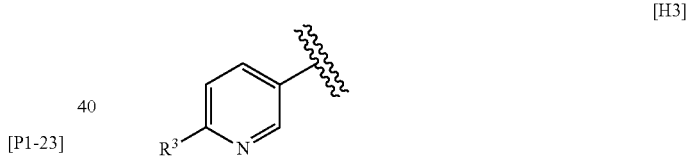

[H3]

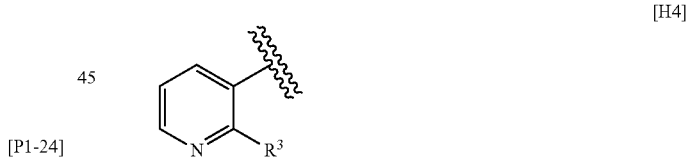

[H4]

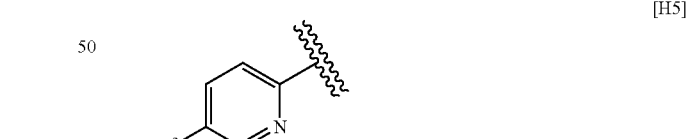

[H5]

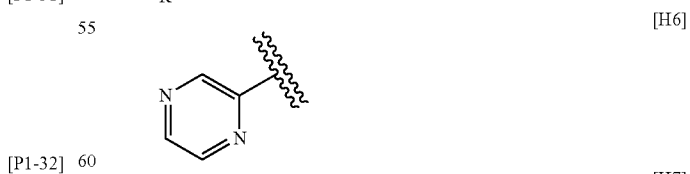

[H6]

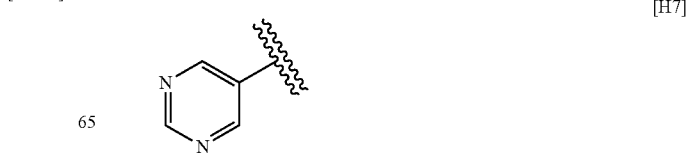

[H7]

-continued

[H8] 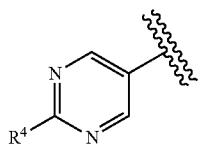

[H9] 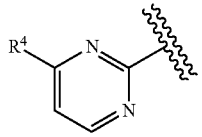

[H10] 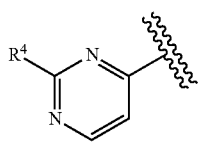

[H11] 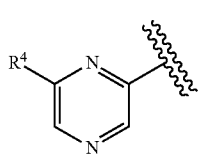

[H12] 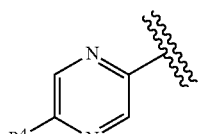

[H13] 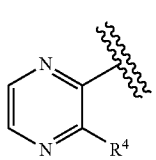

[H14] 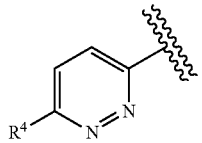

In one embodiment, $R^3$ is halogen or halo-$C_{1-3}$ alkyl. In another embodiment, $R^3$ is fluoro or fluoro-$C_{1-3}$ alkyl.

In one embodiment, $R^4$ is halogen or halo-$C_{1-3}$ alkyl. In another embodiment, $R^4$ is fluoro-$C_{1-3}$ alkyl.

In one embodiment, $R^5$ and $R^6$ are each independently $C_{1-3}$ alkyl.

The term "pharmaceutically acceptable salt" includes any salts known in the art that are not associated with excessive toxicity. Such a pharmaceutically acceptable salt includes, specifically, salts with inorganic acids, salts with organic acids, salts with inorganic bases, and salts with organic bases. Various forms of pharmaceutically acceptable salts are well known in the art and are described in, for example, the following references:
(a) Berge et al., J. Pharm. Sci., 66, p 1-19 (1977),
(b) Stahl et al., "Handbook of Pharmaceutical Salt: Properties, Selection, and Use" (Wiley-VCH, Weinheim, Germany, 2002),
(c) Paulekuhn et al., J. Med. Chem., 50, p 6665-6672 (2007).

A compound of Formula [X] may be reacted with an inorganic acid, organic acid, inorganic base, or organic base according to methods known per se to give a corresponding pharmaceutically acceptable salt thereof.

Such a salt with inorganic acid includes a salt with hydrofluoric acid, hydrochloric acid, hydrobromic acid, hydroiodic acid, nitric acid, phosphoric acid, and sulfuric acid. Such a salt preferably includes a salt with hydrochloric acid, nitric acid, sulfuric acid, phosphoric acid, and hydrobromic acid.

Such a salt with organic acid includes a salt with acetic acid, adipic acid, alginic acid, 4-aminosalicylic acid, anhydromethylenecitric acid, benzoic acid, benzenesulfonic acid, calcium edetate, camphor acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glucoheptonic acid, glycollylarsanilic acid, hexylresorcinol acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, aspartic acid, and glutamic acid. Such a salt preferably includes a salt with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, and 2-hydroxy-1-ethanesulfonic acid.

Such a salt with inorganic base includes a salt with lithium, sodium, potassium, magnesium, calcium, barium, aluminum, zinc, bismuth, and ammoinum. Such a salt preferably includes a salt with sodium, potassium, calcium, magnesium, and zinc.

Such a salt with organic base includes a salt with arecoline, betaine, choline, clemizole, ethylenediamine, N-methylglucamine, N-benzylphenethylamine, tris(hydroxymethyl)methylamine, arginine, and lysine. Such a salt preferably includes a salt with tris(hydroxymethyl)methylamine, N-methylglucamine, and lysine.

A compound of Formula [X] or a pharmaceutically acceptable salt thereof may exist in its solvate form. The term "solvate" means a compound where a solvent molecule is coordinated with a compound of Formula [X] or a pharmaceutically acceptable salt thereof, and includes a hydrate. The solvate is preferably a pharmaceutically acceptable solvate; and includes, for example, a hydrate, an ethanolate, and a dimethyl sulfoxide solvate. Such a solvate specifically includes a hemihydrate, monohydrate, dihydrate, and monoethanolate of a compound of Formula [X], [I], [II], or [III]; and a monohydrate of sodium salt of a compound of Formula [X], [I], [II], or [III] and a 2/3 ethanolate of dihydrochloride salt thereof. These solvates may be obtained according to any of the known methods.

For example, a compound of Formula [II] can exist as a monohydrate as shown in the following Formula [IV]:

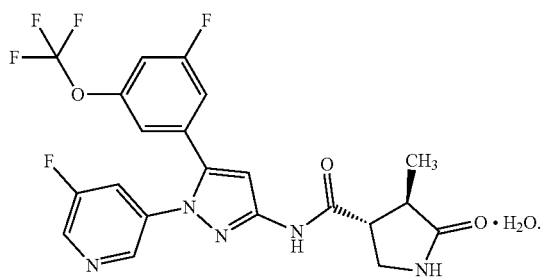

[IV]

A compound of Formula [X] or a pharmaceutically acceptable salt thereof may exist in its tautomeric form. Such a compound of Formula [X] or a pharmaceutically acceptable salt thereof may exist in each tautomeric form or in the form of a mixture of its tautomers.

A compound of Formula [X] or a pharmaceutically acceptable salt thereof may have a carbon-carbon double bond. Such a compound of Formula [X] or a pharmaceutically acceptable salt thereof may exist in its E or Z form or in the form of a mixture of the E- and Z-isomers.

A compound of Formula [X] or a pharmaceutically acceptable salt thereof may have stereoisomers to be recognized as cis/trans isomers. Such a compound of Formula [X] or a pharmaceutically acceptable salt thereof may exist in its cis or trans form, or in the form of a mixture of the cis and trans isomers.

A compound of Formula [X] or a pharmaceutically acceptable salt thereof may have one or more asymmetric carbon atoms. Such a compound of Formula [X] or a pharmaceutically acceptable salt thereof may exist in a single enantiomeric form or a single diastereomeric form, or in the form of a mixture of its enantiomers or diastereomers.

A compound of Formula [X] or a pharmaceutically acceptable salt thereof may exist in its atropisomeric form. Such a compound of Formula [X] or a pharmaceutically acceptable salt thereof may exist in each atropisomeric form or in the form of a mixture of its atropisomers.

A compound of Formula [X] or a pharmaceutically acceptable salt thereof may simultaneously include multiple structural features derived from the above isomers. A compound of Formula [X] or a pharmaceutically acceptable salt thereof may include the above isomers in any ratios.

Formulae, chemical structures, or compound names herein described without specifying stereochemistry include any of the above isomers available, unless otherwise specified.

A diastereomeric mixture may be separated into each diastereomer by conventional methods such as chromatography and crystallization. Each diastereomer may also be prepared from a stereochemically-single starting material or by synthetic methods with stereoselective reactions.

An enantiomeric mixture may be separated into each single enantiomer by methods well known in the art. For example, an enantiomeric mixture may be reacted with a substantially pure enantiomer that is known as a chiral auxiliary to form a diastereomeric mixture, followed by separation from the diastereomeric mixture by ordinary methods such as fractional crystallization and chromatography to give a single diastereomer with an enhanced isomeric ratio or a substantially pure single diastereomer. Then, the separated diastereomer may be converted into a desired enantiomer by removal of the added chiral auxiliary in a cleavage reaction.

An enantiomeric mixture may also be directly separated into each enantiomer by chromatography methods with a chiral stationary phase well known in the art. Alternatively, either of enantiomers may also be obtained from a substantially-pure optically-active starting material or by stereoselective synthesis, i.e., asymmetric induction, for a prochiral intermediate with a chiral auxiliary or asymmetric catalyst.

Absolute configurations may be determined by X-ray crystallography for crystalline products or intermediates. Crystalline products or intermediates derivatized with a reagent with a known configuration and an asymmetric center may optionally be used in the determination.

A compound of Formula [X] may be labelled with an isotope such as $^{2}H$, $^{3}H$, $^{14}C$, and $^{35}S$.

A compound of Formula [X] or a pharmaceutically acceptable salt thereof is preferably a compound of Formula [X] or a pharmaceutically acceptable salt thereof that is substantively purified, and more preferably a compound of Formula [X] or a pharmaceutically acceptable salt thereof that has a purity of 80% or more.

A compound of Formula [X] or a pharmaceutically acceptable salt thereof has an SGLT1 inhibitory activity, and thus may be useful for the treatment and/or prevention of various diseases or conditions that can be expected to be improved by regulating the SGLT1 activity, for example, diabetes (e.g., type 1 diabetes and type 2 diabetes), obesity, diabetic complication (e.g., retinopathy, nephropathy, and neuropathy, which are all known as microangiopathy; and cerebrovascular disease, ischemic heart disease, and membrum-inferius arteriosclerosis obliterans, which are all known as macroangiopathy), hypertrophic cardiomyopathy, ischemic heart disease, cancer, and constipation.

The term "inhibiting SGLT1" means that the function of SGLT1 is inhibited so as to disappear or reduce its activity; and, for example, it means that the function of SGLT1 is inhibited on the basis of the following Test Example 1. The term "inhibiting SGLT1" means preferably "inhibiting human SGLT1". The inhibition of function, or the disperrance or reduction of activity is preferably carried out in human clinical indication.

The term "SGLT1 inhibitor" may be any substance that inhibits SGLT1, and includes small molecule compounds, nucleic acids, polypeptides, proteins, antibodies, and vaccines. The term "SGLT1 inhibitor" means preferably a "human SGLT1 inhibitor".

The term "treating" used herein includes the amelioration of conditions, prevention of aggravation, maintenance of remission, prevention of exacerbation, and prevention of relapse.

The term "preventing" used herein includes delaying the onset of conditions. For example, the phrase "preventing diabetes" includes delaying the onset of type 1 diabetes and/or type 2 diabetes in imparied glucose tolerance.

A pharmaceutical composition herein may be prepared from a therapeutically effective amount of a compound of Formula [X] or a pharmaceutically acceptable salt thereof and at least one or more pharmaceutically acceptable carriers, optionally followed by mixing, according to methods known in the art of medicinal preparations. The amount of a compound of Formula [X] or a pharmaceutically acceptable salt thereof contained in the pharmaceutical composition varies depending on a factor such as dosage forms and dosage amounts and ranges, for example, from 0.1 to 100% by weight of the total amount of the composition.

A dosage form to be formulated with a compound of Formula [X] or a pharmaceutically acceptable salt thereof includes oral preparations such as tablets, capsules, granules, powders, lozenges, syrups, emulsions, and suspensions; and parenteral preparations such as external preparations, suppositories, injections, eye drops, nasal preparations, and pulmonary preparations.

The term "pharmaceutically acceptable carrier" includes various organic or inorganic carrier substances which are conventionally used for a component of a formulation. Such substances include, for example, excipients, disintegrants, binders, fluidizers, and lubricants for solid preparations; solvents, solubilization agents, suspending agents, tonicity agents, buffering agents, and soothing agents for liquid preparations; and bases, emulsifying agents, wetting agents, stabilizers, stabilizing agents, dispersing agents, plasticizing agents, pH adjusters, absorption promoters, gelators, antiseptic agents, bulking agents, solubilizers, solubilization agents, and suspending agents for semisolid preparations. Additives such as preserving agents, antioxidant agents, coloring agents, and sweetening agents may be further added, if needed.

Such an "excipient" includes, for example, lactose, white soft sugar, D-mannitol, D-sorbitol, corn starch, dextrin, microcrystalline cellulose, crystalline cellulose, carmellose, carmellose calcium, sodium carboxymethylstarch, low-substituted hydroxypropylcellulose, and gum arabic.

Such a "disintegrant" includes, for example, carmellose, carmellose calcium, carmellose sodium, sodium carboxymethylstarch, crosscarmellose sodium, crospovidone, low-substituted hydroxypropylcellulose, hydroxypropylmethyl cellulose, and crystalline cellulose.

Such a "binder" includes, for example, hydroxypropylcellulose, hydroxypropylmethyl cellulose, povidone, crystalline cellulose, white soft sugar, dextrin, starch, gelatin, carmellose sodium, and gum arabic.

Such a "fluidizer" includes, for example, light anhydrous silicic acid and magnesium stearate.

Such a "lubricant" includes, for example, magnesium stearate, calcium stearate, and talc.

Such a "solvent" includes, for example, purified water, ethanol, propylene glycol, macrogol, sesame oil, corn oil, and olive oil.

Such a "solubilization agent" includes, for example, propylene glycol, D-mannitol, benzyl benzoate, ethanol, triethanolamine, sodium carbonate, and sodium citrate.

Such a "suspending agent" includes, for example, benzalkonium chloride, carmellose, hydroxypropylcellulose, propylene glycol, povidone, methylcellulose, and glyceryl monostearate.

Such a "tonicity agent" includes, for example, glucose, D-sorbitol, sodium chloride, and D-mannitol.

Such a "buffering agent" includes, for example, disodium hydrogen phosphate, sodium acetate, sodium carbonate, and sodium citrate.

Such a "soothing agent" includes, for example, benzyl alcohol.

Such a "base" includes, for example, water, oils from animals or vegetables such as olive oil, corn oil, *arachis* oil, sesame oil, and castor oil, lower alcohols such as ethanol, propanol, propylene glycol, 1,3-butylene glycol, and phenol, higher fatty acids and esters thereof, waxes, higher alcohol, polyhydric alcohol, hydrocarbons such as white petrolatum, liquid paraffin, and paraffin, hydrophilic petrolatum, purified lanolin, absorption ointment, hydrous lanolin, hydrophilic ointment, starch, pullulan, gum arabic, tragacanth gum, gelatin, dextran, cellulose derivatives such as methylcellulose, carboxymethyl cellulose, hydroxyethyl cellulose, and hydroxypropyl cellulose, synthetic polymers such as carboxyvinyl polymer, sodium polyacrylate, polyvinylalcohol, and polyvinylpyrrolidone, propylene glycol, macrogol such as Macrogol 200 to 600, and a combination of two or more of them.

Such a "preserving agent" includes, for example, ethyl parahydroxybenzoate, chlorobutanol, benzyl alcohol, sodium dehydroacetate, and sorbic acid.

Such an "anti-oxidant agent" includes, for example, sodium sulfite and ascorbic acid.

Such a "coloring agent" includes, for example, food colors (e.g., Food Red No. 2 or No. 3, Food Yellow No. 4, or No. 5) and β-carotene.

Such a "sweetening agent" includes, for example, saccharin sodium, dipotassium glycyrrhizinate, and aspartame.

A pharmaceutical composition herein may be administered orally or parenterally (e.g., topically, rectally, intravenously, intramuscularly, and subcutaneously) to humans as well as mammals other than humans such as mice, rats, hamsters, guinea pigs, rabbits, cats, dogs, pigs, cows, horses, sheep, and monkeys. The dosage amount varies depending on the subjects which will be administered to, diseases, conditions, dosage forms, and administration routes. For example, the daily dose for oral administration to an adult patient is typically within the range of about 0.01 mg to about 1 g of the active ingredient, i.e., a compound of Formula [X]. Such a dosage amount can be administered at one time or several times.

A kit such as kits for administration, treatment, and/or prevention, a package such as packaged goods, and a set and/or case of medicine which comprises a pharmaceutical composition comprising a compound of Formula [X] or a pharmaceutically acceptable salt thereof as the active ingredient or active agent and a written matter concerning the composition indicating that the composition may or should be used for treatment and/or prevention are also useful. Such a kit, package, and set of medicine may comprise one or more containers filled with the pharmaceutical composition or one or more active ingredients and other drugs or medicines (or ingredients) used for the composition. Examples of such a kit, package, and set of medicine include commercial kits, commercial packages, and commercial medicine set for appropriate use in the treatment and/or prevention of intended diseases. The written matter comprised in such a kit, package, and set of medicine includes a cautionary note or package insert in the form designated by the government organization that regulates manufactures, use, or sales of pharmaceutical or biological products which ensures an approval by the government organization on manufactures, use, or sales of products concerning administration to humans. The kit, package, and set of medicine may include packaged products as well as structures configured for appropriate administration steps and configured so as to be able to achieve more preferable medical treatment and/or prevention including treatment and/or prevention of intended diseases.

A general preparation of a compound of Formula [X] or a pharmaceutically acceptable salt thereof is illustrated as below. Compounds of Formulae [1] to [20] include their pharmaceutically acceptable salts if they can exist. For example, the term "compound of Formula [1]" includes a compound of Formula [1] and a pharmaceutically acceptable salt thereof if such a pharmaceutically acceptable salt exists.

The term "room temperature" used as below ranges, for example, from about 15° C. to about 30° C., preferably from about 20° C. to about 25° C.

General Preparation: A Compound of Formula [X] or a Pharmaceutically Acceptable Salt Thereof A compound of Formula [X] or a pharmaceutically acceptable salt thereof can be obtained according to, for example, the following processes.

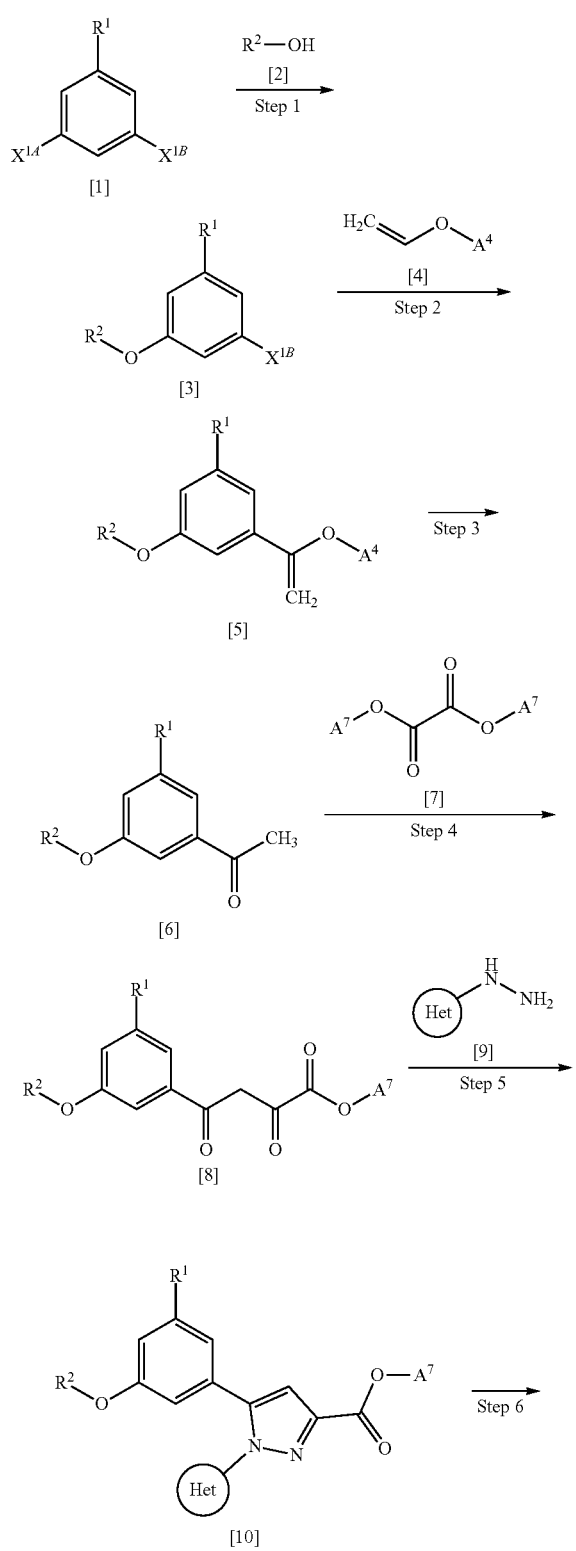

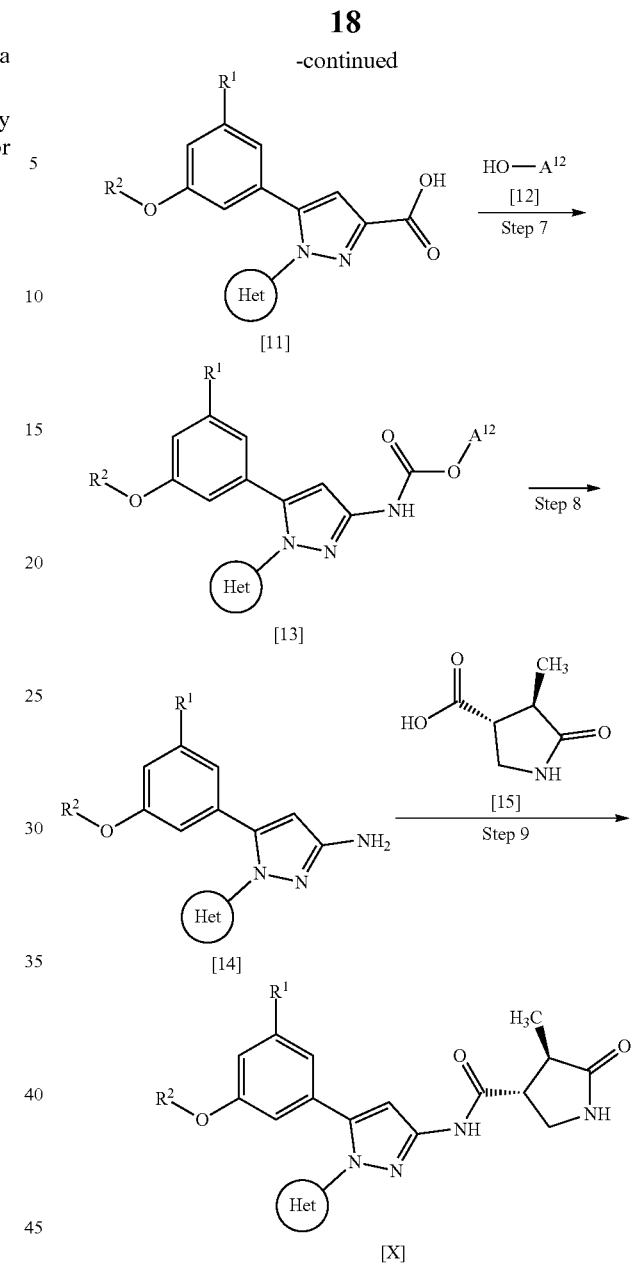

In the scheme, $R^1$, $R^2$, and Ring Het are defined as above, $X^{1A}$ and $X^{1B}$ are each independently halogen, provided that $X^{1A}$ is more reactive than $X^{1B}$ in Step 1, when $R^1$ is halogen, $R^1$ is preferably the same halogen as $X^{1A}$, $A^4$ is n-butyl, $A^7$ is $C_{1-4}$ alkyl or benzyl, and $A^{12}$ is tert-butyl or benzyl.

(Step 1)

A compound of Formula [3] can be obtained by reaction of a compound of Formula [1] with a compound of Formula [2] in a solvent in the presence of a base.

Such a solvent includes, for example, ether solvents such as 1,2-dimethoxyethane; and polar solvents such as N,N-dimethylformamide, N-methylpyrrolidone, 1,3-dimethyl-2-imidazolidinone, and N,N'-dimethylpropyleneurea. A preferable solvent herein is 1,3-dimethyl-2-imidazolidinone.

Such a base includes, for example, cesium carbonate and sodium hydride. A preferable base herein is sodium hydride.

The reaction temperature herein ranges, for example, from 60° C. to 170° C., preferably from 100° C. to 140° C.

Both compounds of Formulae [1] and [2] may be commercially available or prepared according to known methods.

Alternatively, when $R^2$ is trifluoromethyl, a compound of Formula [3] may be commercially available.

(Step 2)

A compound of Formula [5] can be obtained by Mizoroki-Heck reaction of a compound of Formula [3] with a compound of Formula [4]. For example, a compound of Formula [5] can be obtained by reaction of a compound of Formula [3] with a compound of Formula [4] in a solvent in the presence of a palladium catalyst and base.

Such a solvent includes, for example, alcoholic solvents such as ethylene glycol; and polar solvents such as N,N-dimethylformamide. A preferable solvent herein is ethylene glycol.

Such a palladium catalyst includes, for example, a mixture of palladium (II) acetate with 1,1'-bis(diphenylphosphino)ferrocene or 1,3-bis(diphenylphosphino)propane. A preferable palladium catalyst herein is a mixture of palladium (II) acetate with 1,1'-bis(diphenylphosphino)ferrocene.

Such a base includes, for example, organic bases such as triethylamine. A preferable base herein is triethylamine.

The reaction temperature herein ranges, for example, 80° C. to 150° C., preferably from 100° C. to 140° C.

A compound of Formula [4] may be commercially available or prepared according to known methods.

(Step 3) A compound of Formula [6] can be obtained by conversion of the "—C(=CH$_2$)OA$^4$" group into a "—C(=O)CH$_3$" group in a compound of Formula [5]. For example, a compound of Formula [6] can be obtained by reaction of a compound of Formula [5] in a solvent in the presence of an acid.

Such a solvent includes, for example, ketone solvents such as acetone; alcoholic solvents such as ethylene glycol; ether solvents such as tetrahydrofuran and 1,4-dioxane; halogenated hydrocarbons such as dichloromethane; polar solvents such as N,N-dimethylformamide; water; and a mixed solvent of any of them. A preferable solvent herein is a mixed solvent of tetrahydrofuran and water.

Such an acid includes, for example, hydrochloric acid and trifluoroacetic acid. A preferable acid herein is hydrochloric acid.

The reaction temperature herein ranges, for example, from 20° C. to 50° C. and is preferably room temperature.

(Step 4)

A compound of Formula [8] can be obtained by reaction of a compound of Formula [6] with a compound of Formula [7] in a solvent in the presence of a base.

Such a solvent includes, for example, ether solvents such as tetrahydrofuran, diethyl ether, and 1,2-dimethoxyethane; alcoholic solvents such as methanol and ethanol; hydrocarbons such as toluene; polar solvents such as N,N-dimethylformamide; and a mixed solvent of any of them. A preferable solvent herein is tetrahydrofuran.

Such a base includes, for example, lithium tert-butoxide, sodium tert-butoxide, potassium tert-butoxide, sodium methoxide, sodium ethoxide, lithium diisopropylamide, lithium hexamethyldisilazane, and sodium hydride. A preferable base herein is lithium tert-butoxide.

The reaction temperature herein ranges, for example, from −78° C. to 110° C., preferably from 0° C. to room temperature.

A compound of Formula [7] may be commercially available or prepared according to known methods.

(Step 5)

A compound of Formula [10] can be obtained by reaction of a compound of Formula [8] with a compound of Formula [9] in a solvent in the presence of an acid.

Such a solvent includes, for example, ether solvents such as tetrahydrofuran; alcoholic solvents such as methanol and ethanol; and hydrocarbons such as toluene.

Such an acid includes, for example, hydrochloric acid, sulfuric acid, acetic acid, trifluoroacetic acid, and p-toluenesulfonic acid. A preferable acid herein is acetic acid. These acids may also be used as a solvent herein.

The reaction temperature ranges, for example, from 20° C. to 130° C., preferably from 80° C. to 110° C.

A compound of Formula [9] may be commercially available or prepared according to known methods, or may also be obtained according to the general preparation as described below.

(Step 6)

A compound of Formula [11] can be obtained by elimination of the "–A$^7$" group from a compound of Formula [10]. The elimination reaction may be performed under suitable conditions depending on A$^7$. For example, when A$^7$ is ethyl, a compound of Formula [11] can be obtained by reaction of a compound of Formula [10] in a solvent in the presence of a base.

Such a solvent includes, for example, alcoholic solvents such as methanol and ethanol; ether solvents such as tetrahydrofuran; water; and a mixed solvent of any of them. A preferable solvent herein is a mixed solvent of two or more solvents selected from the group consisting of methanol, tetrahydrofuran, and water.

Such a base includes, for example, lithium hydroxide, sodium hydroxide, and potassium hydroxide. A preferable base herein is sodium hydroxide.

The reaction temperature herein ranges, for example, from 0° C. to 100° C., preferably from room temperature to 40° C.

(Step 7)

A compound of Formula [13] can be obtained by Curtius rearrangement of a compound of Formula [11] and a compound of Formula [12]. For example, a compound of Formula [13] can be obtained by reaction of a compound of Formula [11] with an azidation agent in the presence of a base in a solvent, followed by reaction of a compound of Formula [12].

Such a solvent includes, for example, ether solvents such as tetrahydrofuran and 1,4-dioxane; and hydrocarbons such as toluene. Alternatively, a compound of Formula [12] may also be used as a solvent herein. A preferable solvent herein is toluene or a mixed solvent of toluene and a compound of Formula [12].

Such an azidation agent includes, for example, diphenylphosphoryl.

Such a base includes, for example, organic bases such as triethylamine and N,N-diisopropylethylamine. A preferable base herein is triethylamine.

The reaction temperature herein ranges, for example, from 65° C. to 130° C., preferably from 90° C. to 110° C.

A compound of Formula [12] may be commercially available or prepared according to known methods.

(Step 8)

A compound of Formula [14] can be obtained by elimination of the "—C(=O)OA$^{12}$" group from a compound of Formula [13] in a solvent. The elimination reaction may be performed under suitable conditions depending on A$^{12}$. For example, when $A^{12}$ is tert-butyl, a compound of Formula [14] can be obtained by reaction of a compound of Formula [13] in a solvent in the presence of an acid.

Such a solvent includes, for example, ester solvents such as ethyl acetate; alcoholic solvents such as methanol and ethanol; ether solvents such as tetrahydrofuran and 1,4-dioxane; halogenated hydrocarbons such as dichloromethane; water; and a mixed solvent of any of them. A preferable solvent herein is 1,4-dioxane.

Such an acid includes, for example, hydrochloric acid, sulfuric acid, and trifluoroacetic acid. A preferable acid herein is hydrochloric acid. These acids may also be used as a solven herein.

The reaction temperature herein ranges, for example, from 0° C. to 60° C., preferably from 0° C. to room temperature.

(Step 9)

A compound of Formula [X] can be obtained by condensation reaction of a compound of Formula [14] with a compound of Formula [15] in a solvent.

Such a solvent includes, for example, halogenated hydrocarbons such as chloroform; ether solvents such as tetrahydrofuran; polar solvents such as pyridine, acetonitrile, and N,N-dimethylformamide; and a mixed solvent of any of them. A preferable solvent herein is pyridine.

The condensation agent includes, for example, dicyclohexylcarbodiimide (DCC), 1-ethyl-3-(3-dimethylaminopropyl)carbodiimide hydrochloride (WSC.HCl), diisopropylcarbodiimide, 1,1'-carbonyldiimidazole (CDI), O-(7-azabenzotriazol-1-yl)-N,N,N',N'-tetramethyluronium hexafluorophosphate (HATU), {{[(1-cyano-2-ethoxy-2-oxoethyliden)amino]oxy}-4-morpholinomethylene}dimethylammonium hexafluorophosphate (COMU), 4-(4,6-dimethoxy-1,3,5-triazin-2-yl)-4-methylmorpholinium chloride n-hydrate (DMT-MM), (benzotriazol-1-yloxy)tripyrrolidinophosphonium hexafluorophosphate (PyBOP), diphenylphosphoryl azide, and anhydrous propylphosphonic acid. A preferable condensation agent herein is 1-ethyl-3-(3-dimethylaminopropyl)carbodiimide hydrochloride (WSC.HCl).

The reaction temperature herein ranges, for example, from 0° C. to 100° C. and is preferably room temperature.

A compound of Formula [15] can be obtained by, for example, the method of Reference Example A as described below.

General Preparation: A Compound of Formula [9]

A compound of Formula [9] can be obtained in, for example, the following process.

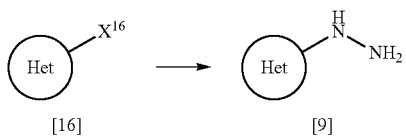

[16]  [9]

In the scheme, Ring Het is defined as above, and $X^{16}$ is halogen.

A compound of Formula [9] can be obtained by reaction of a compound of Formula [16] with hydrazine monohydrate in a solvent.

Such a solvent includes, for example, ether solvents such as tetrahydrofuran and 1,4-dioxane; alcoholic solvents such as ethanol and 2-propanol; halogenated hydrocarbons such as dichloromethane; polar solvents such as N,N-dimethylformamide and pyridine; water; and a mixed solvent of any of them. Alternatively, hydrazine monohydrate may also be used as a solvent herein. A preferable solvent herein is a mixed solvent of 2-propanol and hydrazine monohydrate.

The reaction temperature herein ranges, for example, from room temperature to 140° C., preferably from 60° C. to 100° C.

A compound of Formula [16] may be commercially available or prepared according to known methods.

When Ring Het is pyridyl substituted with $R^3$, a compound of Formula [9] may be obtained in, for example, the following process.

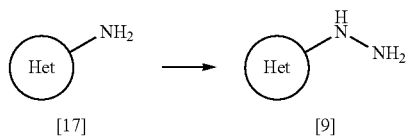

[17]  [9]

In the scheme, Ring Het is pyridyl substituted with $R^3$, and $R^3$ is defined as above.

A compound of Formula [9] can be obtained by diazotization of a compound of Formula [17] in the presence of an acid in a solvent, followed by reduction.

Such a solvent includes, for example, water.

Such a diazotization agent includes, for example, sodium nitrite.

Such an acid includes, for example, hydrochloric acid and sulfuric acid. A preferable acid herein is hydrochloric acid.

The reducing agent herein includes, for example, tin (II) chloride and sodium sulfite. A preferable reducing agent herein is tin (II) chloride.

The reaction temperature for the diazatization ranges, for example, from −20° C. to 5° C., preferably from −5° C. to 0° C.

The reaction temperature for the reduction ranges, for example, from −5° C. to room temperature, preferably from 0° C. to room temperature.

A compound of Formula [17] may be commercially available or prepared according to known methods.

Alternatively, when Ring Het is (1) pyridyl substituted with $R^3$ or (2) pyrimidinyl optionally substituted with $R^4$, a compound of Formula [9] can also be obtained in, for example, the following process.

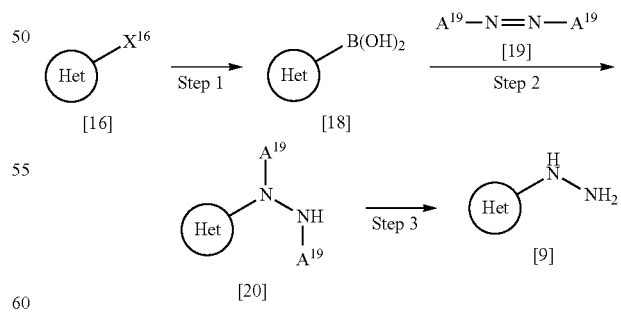

In the scheme,

Ring Het is (1) pyridyl substituted with $R^3$ or (2) pyrimidinyl optionally substituted with $R^4$, $R^3$, $R^4$, and $X^{16}$ are defined as above, and $A^{19}$ is tert-butoxycarbonyl or benzyloxycarbonyl.

(Step 1)

A compound of Formula [18] can be obtained by reaction of a compound of Formula [16] with a base and boronic acid ester in a solvent.

Such a solvent includes, for example, ether solvents such as tetrahydrofuran; hydrocarbons such as toluene; and a mixed solvent of any of them. A preferable solvent herein is tetrahydrofuran.

Such a base includes, for example, n-butyllithium and isopropylmagnesium bromide. A preferable base herein is n-butyllithium.

Such a boronic acid ester includes, for example, triisopropyl borate and trimethyl borate. A preferable boronic acid ester herein is triisopropyl borate.

The reaction temperature herein ranges, for example, from −78° C. to room temperature, preferably from −78° C. to 0° C.

A compound of Formula [16] may be commercially available or prepared according to known methods.

(Step 2)

A compound of Formula [20] can be obtained by reaction of a compound of Formula [18] with a compound of Formula [19] in the presence of a copper catalyst in a solvent.

Such a solvent includes, for example, ether solvents such as tetrahydrofuran; and alcoholic solvents such as methanol. A preferable solvent herein is methanol.

Such a copper catalyst includes, for example, copper (II) acetate.

The reaction temperature herein ranges, for example, from room temperature to 100° C., preferably from 45° C. to 65° C.

(Step 3)

A compound of Formula [9] can be obtained by elimination of the "−$A^{19}$" groups in a compound of Formula [20]. The elimination reaction may be performed under suitable conditions depending on $A^{19}$. For example, when $A^{19}$ is tert-butoxycarbonyl, a compound of Formula [9] can be obtained by reaction of a compound of Formula [20] in the presence of an acid in a solvent.

Such a solvent includes, for example, ester solvents such as ethyl acetate; alcoholic solvents such as methanol and ethanol; ether solvents such as tetrahydrofuran and 1,4-dioxane; halogenated hydrocarbons such as dichloromethane; water; and a mixed solvent of any of them. A preferable solvent herein is 1,4-dioxane.

Such an acid includes, for example, hydrochloric acid, sulfuric acid, and trifluoroacetic acid. A preferable acid herein is hydrochloric acid.

The reaction temperature herein ranges, for example, from 0° C. to 60° C., preferably from 0° C. to room temperature.

EXAMPLES

The present invention is illustrated in more detail with Reference Examples, Examples, Test Examples, and Formulation Examples as below, but is not intended to be limited thereto.

Abbreviations used herein are defined as follows.
DMF: N,N-Dimethylformamide
DMSO: Dimethyl sulfoxide
THF: Tetrahydrofuran
CPME: Cyclopentyl methyl ether
WSC.HCl: 1-Ethyl-3-(3-dimethylaminopropyl)carbodiimide hydrochloride $^1$H-NMR spectra were measured in CDCl$_3$ or DMSO-d$_6$ with tetramethylsilane for an internal standard, and all δ values are shown in ppm. The measurement was carried out with an NMR spectrometer with 400 MHz, unless otherwise specified.

Symbols in the Examples mean as follows.
s: singlet
d: doublet
t: triplet
q: quartet
dd: double doublet
ddd: double double doublet
brs: broad singlet
m: multiplet
J: coupling constant

[Reference Example A] Preparation of (3R,4R)-4-methyl-5-oxopyrrolidine-3-carboxylic acid

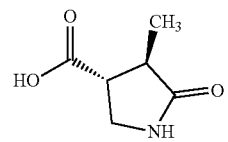

(Step A-1) Preparation of diethyl 2-methyl-3-methylenesuccinate

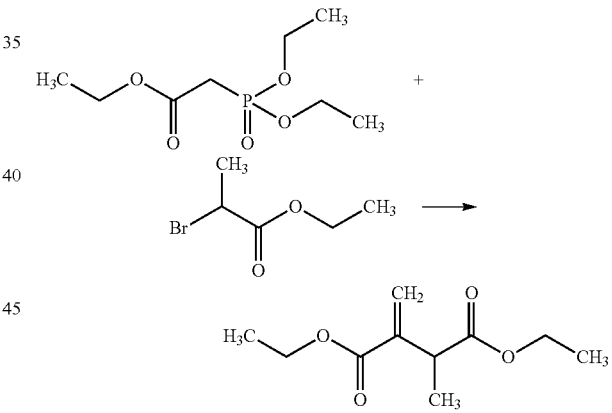

To potassium tert-butoxide (180 g) was added THF (2.55 L) at room temperature under nitrogen flow. To the mixture was added dropwise triethyl phosphonoacetate (314 g) under ice cooling over 13 minutes. The dropping funnel used was washed with THF (511 mL), and the washings were added to the reaction mixture. The reaction mixture was stirred for 2 hours 9 minutes under ice cooling. To the reaction mixture was added dropwise ethyl 2-bromopropionate (247 g) over 20 minutes under ice cooling. The dropping funnel used was washed with THF (79 mL), and the washings were added to the reaction mixture. The reaction mixture was stirred at room temperature for 22 hours 45 minutes. To the reaction mixture was added potassium carbonate (188 g) over 1 minute under ice cooling. To the reaction mixture was added dropwise 37% by weight of aqueous formaldehyde solution (152 mL) over 10 minutes under ice cooling. The reaction mixture was stirred at room temperature for 19 hours 44 minutes. To the reaction mixture was added water (1.57 L) at room temperature over 1 minute. The reaction mixture was stirred at room temperature for 1 hour 48 minutes. The reaction mixture was separated. The resulted aqueous layer was extracted with THF (200 mL) twice. The resulted organic layers were combined and concentrated. To the residue were added toluene (471 mL) and brine (471 mL). The reaction mixture was stirred and separated. The organic layer was dried over sodium sulfate (63 g). Sodium sulfate was filtered off. Separately, a similar reaction was performed with triethyl phosphonoacetate (300 g) to give a filtrate, which was then combined with the filtrate obtained above to give a solution of the title compound (equivalent to 2.66 mol) in toluene (about 921 mL). The resulted solution of the title compound in toluene was deemed to afford the yield of 100% and used in the next step. The generation of the title compound was confirmed by HPLC analysis.

The measuring instrument and conditions for HPLC are shown as follows.

Measuring instrument: HPLC system, Shimadzu Corporation, High-Performance Liquid Chromatograph Prominence Measuring conditions:

Column: Kinetex C18: 2.6 μm, 50 mm×2.1 mm (Phenomenex)

Column temperature: 40° C.

Flow rate: 0.4 mL/min.

Time for analysis: 10 min.

Detection wavelength: UV (220 nm)

Mobile phase: (Solutin A) water, (Solution B) acetonitrile

Delivery of mobile phase: A mixing ratio (Solution A/Solution B (volume %)) of Solution A and Solution B was maintained 80/20 from 0 minute to 0.01 minute after injection, changed linearly from 80/20 to 10/90 from 0.01 minute to 7 minutes, maintained 10/90 from 7 minutes to 8 minutes, changed linearly from 10/90 to 80/20 from 8 minutes to 9 minutes, and maintained 80/20 from 9 minutes to 10 minutes.

The retention time of the title compound was about 3.7 minutes under the measuring conditions for HPLC.

(Step A-2) Preparation of a mixture of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate To a solution of diethyl 2-methyl-3-methylenesuccinate (equivalent to 2.66 mol) obtained in Step A-1 in toluene (about 921 mL) was added dropwise 2,4-dimethoxybenzylamine (468 g) over 2 minutes at room temperature under nitrogen flow. The reaction mixture was stirred at 120° C. for 5 hours 45 minutes. The reaction mixture was let stand for a weekend at room temperature. The reaction mixture was cooled with ice to about 15° C. of the internal temperature. To the reaction mixture was added dropwise 2N hydrochloric acid (1.33 L), and the mixture was stirred. The reaction mixture was separated. The resulted aqueous layer was extracted with toluene (150 mL). The resulted organic layers were combined, washed with a mixed solution of brine and water (600 mL, brine/water=1/1), dried over sodium sulfate (120 g), concentrated, and dried under reduced pressure at room temperature overnight to give a crude product of the title compound (790 g; cis/trans=about 1/1, 5.5% by weight of toluene inclusive). The generation of the title compound was confirmed by HPLC analysis.

The measuring instrument and conditions for HPLC are shown as follows.

Measuring instrument: HPLC system, Shimadzu Corporation, High-Performance Liquid Chromatograph Prominence Measuring conditions:

Column: Atlantis T3: 5 μm, 150 mm×4.6 mm (Waters)

Column temperature: 40° C.

Flow rate: 1.15 mL/min.

Time for analysis: 18 min.

Detection wavelength: UV (220 nm)

Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40 from 0 minute to 0.5 minute after injection, changed linearly from 60/40 to 10/90 from 0.5 minute to 8 minutes, maintained 10/90 from 8 minutes to 12.5 minutes, changed linearly from 10/90 to 60/40 from 12.5 minutes to 13.5 minutes, and maintained 60/40 from 13.5 minutes to 18 minutes.

The retention time was about 6.6 minutes for ethyl (cis)-1-(2,4-dimethoxybenzyl)-4-methyl-5-oxopyrrolidine-3-carboxylate and about 6.9 minutes for ethyl (trans)-1-(2,4-dimethoxybenzyl)-4-methyl-5-oxopyrrolidine-3-carboxylate under the measuring conditions for HPLC.

(Step A-3) Preparation of (trans)-1-(2,4-dimethoxybenzyl)-4-methyl-5-oxopyrrolidine-3-carboxylic acid

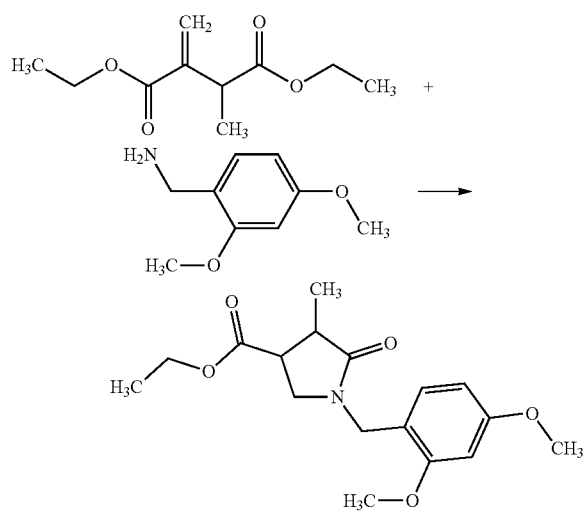

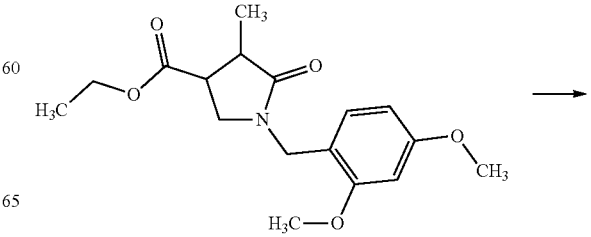

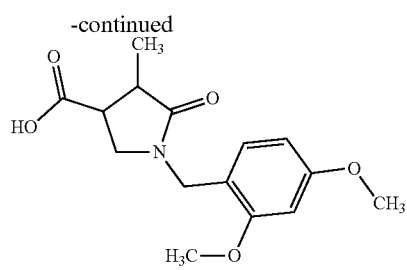

To a crude mixture (790 g, 5.5% by weight of toluene inclusive) of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate, obtained in step A-2, was added ethanol (1.15 L) at room temperature under nitrogen flow. To the reaction mixture was added dropwise sodium ethoxide (20% by weight solution in ethanol, 1.15 L) at room temperature over 31 minutes. The reaction mixture was stirred at room temperature for 2 hours 57 minutes. The reaction mixture was cooled with ice, and thereto was added dropwise water (1.84 L) over 33 minutes. To the reaction mixture were added CPME (1.8 L) and toluene (1.8 L) at room temperature, and the mixture was separated (Organic layer 1). To the resulted aquesous layer was added CPME (1.8 L), and the mixture was separated (Organic layer 2). Solvent (1.8 L) was removed from the resulted aqueous layer by evaporation. To the resulted aqueous layer was added dropwise 6N hydrochloric acid (110 mL) under ice cooling, and thereto was added ethyl acetate (1.8 L). To the mixture was added dropwise 6N hydrochloric acid (300 mL) under ice cooling, and the mixture was stirred for about 10 minutes. To the mixture were sequentially added water (2.2 L), 6N hydrochloric acid (50 mL), water (1.0 L), 10% by weight of aqueous sodium hydrogen sulfate solution (300 mL), and ethanol (300 mL) under ice cooling. The mixture was stirred at room temperature overnight. To the mixture was added ethyl acetate (600 mL), and the mixture was separated. The resulted aqueous layer was extracted with ethyl acetate (600 mL) twice. The resulted organic layers were combined (except for Organic layer 1 and Organic layer 2) and washed with a mixture of brine and water (1 L, brine/water=1/1). To the resulted organic layer were added sodium sulfate (120 g) and activated carbon (30 g), and the mixture was stirred at room temperature for 1 hour. The mixture was filtered through Celite to remove insoluble substances. The insoluble substances were washed with ethyl acetate (3 L). The resulted filtrates were combined and concentrated, and dried under reduced pressure at room temperature for 3 hours to give a crude product of the title compound (561 g).

Separately, the above Organic layer 1 and Organic layer 2 were combined and concentrated. To the residue were added toluene (450 mL) and water (450 mL), and the mixture was separated. The resulted aqueous layer was washed with toluene (450 mL) twice. To the aqueous layer was added ethyl acetate (450 mL). To the mixture was added dropwise 6N hydrochloric acid (70 mL) under ice cooling. To the mixture was added ethyl acetate (300 mL), and the mixture was separated. The resulted aqueous layer was extracted with ethyl acetate (150 mL). The resulted organic layers of ethyl acetate were combined and washed with a mixture of brine and water (225 mL, brine/water=1/1). To the organic layer were added sodium sulfate (30 g) and activated carbon (7.5 g), and the mixture was stirred at room temperature for 1 hour. The mixture was filtered to remove insoluble substances. The insoluble substances were washed with ethyl acetate (750 mL). The resulted filtrates were combined and cocentrated, and dried under reduced pressure at room temperature for 3 hours to give a crude product of the title compound (87.3 g).

This crude product was combined with the crude product of the title compound obtained above, and thereto was added CPME (3 L) under nitrogen flow. The mixture was stirred at 120° C. The mixture was slowly cooled to room temperature with stirring for 17 hours 34 minutes. The mixture was cooled with ice and stirred at about 1° C. of the internal temperature for 3 hours. The precipitate was filtered and washed with cooled CPME (900 mL). The precipitate was dried under reduced pressure at 50° C. overnight to give the title compound (585 g) in the total yield of 75% in the 3 steps. The generation of the title compound was confirmed by HPLC analysis and NMR.

The measuring instrument and conditions for HPLC are the same as those in Step A-2. The retention time of the title compound was about 3.1 minutes under the measuring conditions for HPLC.

$^1$H-NMR (CDCl$_3$) δ: 1.33 (d, 3H, J=6.5 Hz), 2.68-2.85 (m, 2H), 3.33-3.48 (m, 2H), 3.80 (s, 6H), 4.43 (s, 2H), 6.42-6.46 (m, 2H), 7.11-7.15 (m, 1H).

(Step A-4) Preparation of a Diastereomer Salt of (3R,4R)-1-(2,4-dimethoxybenzyl)-4-methyl-5-oxopyrrolidine-3-carboxylic acid with (1R,2R)-(−)-2-amino-1-(4-nitrophenyl)-1,3-propanediol

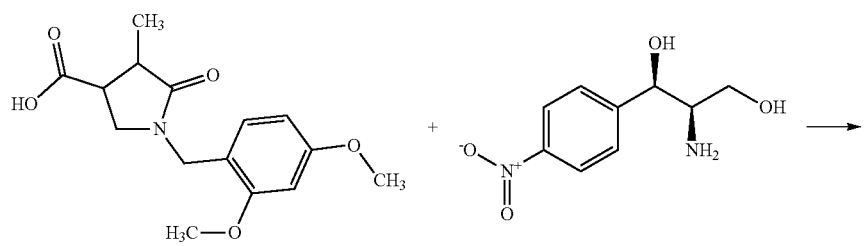

-continued

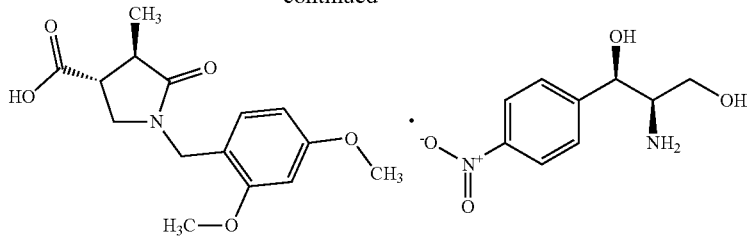

To (trans)-1-(2,4-dimethoxybenzyl)-4-methyl-5-oxopyrrolidine-3-carboxylic acid (585 g) obtained in Step A-3 was added acetonitrile (2.9 L) at room temperature under nitrogen flow. The mixture was stirred at 85° C. To the mixture was added (1R,2R)-(−)-2-amino-1-(4-nitrophenyl)-1,3-propanediol (254 g) over 14 minutes at 85° C. The reaction mixture was stirred at 90° C. for 2 hours 48 minutes. The reaction mixture was cooled to room temperature with stirring overnight. The precipitate was filtered and washed with acetonitrile (2.4 L). The precipitate was dried under ordinary pressure for 8.5 hours at room temperature to give a crude crystal of the title compound (516 g). To the crude crystal were added acetonitrile (2.5 L) and water (0.5 L) at room temperature under nitrogen flow. The mixture was stirred at 100° C. for 1 hour 14 minutes. To the mixture was added dropwise acetonitrile (1.5 L) at 100° C. over 1 hour 7 minutes. The mixture was stirred at 100° C. for 10 minutes. The mixture was cooled to room temperature with stirring for 21 hours 10 minutes. The mixture was stirred for 3 hours 54 minutes under ice cooling. The precipitate was collected by filtration and washed with acetonitrile (1.5 L). The precipitate was dried under ordinary pressure at room temperature for 4 hours to give the title compound (448 g, 99.8% de) in the yield of 45%. The generation of the title compound was confirmed by HPLC analysis.

The measuring instrument and conditions for HPLC are shown as follows.

Measuring instrument: HPLC system, Shimadzu Corporation,
High-Performance Liquid Chromatograph Prominence
Measuring conditions:
Column: CHIRAL PAK AD-3R: 3 μm, 150 mm×4.6 mm (Daicel)
Column temperature: 40° C.
Flow rate: 0.50 mL/min.
Time for analysis: 10 min.
Detection wavelength: UV (220 nm)
Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40.

The retention time was about 5.6 minutes for (3R,4R)-1-(2,4-dimethoxybenzyl)-4-methyl-5-oxopyrrolidine-3-carboxylic acid and about 6.5 minutes for (3S,4S)-1-(2,4-dimethoxybenzyl)-4-methyl-5-oxopyrrolidine-3-carboxylic acid under the measuring conditions for HPLC.

The conformation of the title compound was determined by X-ray crystallography of its single crystal obtained after recrystallization from methyl isobutyl ketone.

Diastereomeric excess was determined from HPLC area percentages in the measurement results ((3R,4R)/(3S,4S) =99.886%/0.114%).

(Step A-5) Preparation of (3R,4R)-1-(2,4-dimethoxybenzyl)-4-methyl-5-oxopyrrolidine-3-carboxylic acid

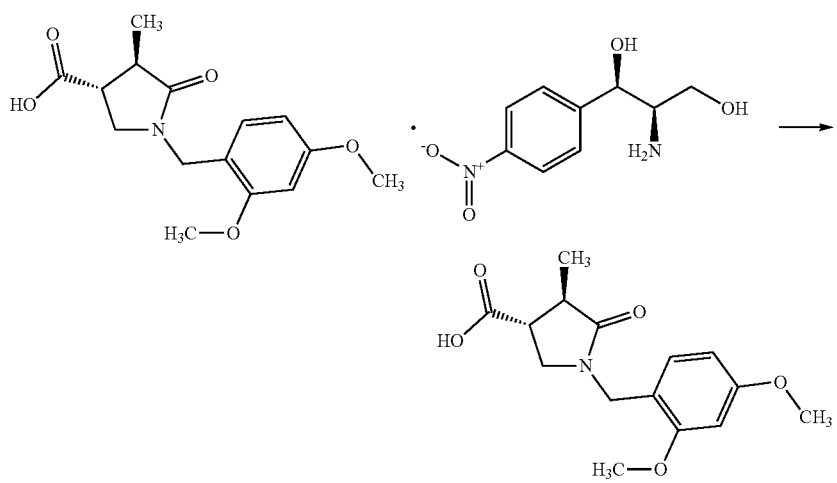

To a diastereomer salt of (3R,4R)-1-(2,4-dimethoxybenzyl)-4-methyl-5-oxopyrrolidine-3-carboxylic acid with (1R, 2R)-(−)-2-amino-1-(4-nitrophenyl)-1,3-propanediol (448 g) obtained in Step A-4 were added ethyl acetate (1.8 L) and water (1.34 L) at room temperature. To the mixture was added dropwise 6N hydrochloric acid (168 mL) at room temperature over 16 minutes. The mixture was separated. The resulted aqueous layer was extracted with ethyl acetate (450 mL) three times. The resulted organic layers were combined and washed sequentially with 2N hydrochloric acid (224 mL) and brine (224 mL), and then dried over sodium sulfate (90 g) and concentrated. To the residue was added toluene (220 mL), and the mixture was concentrated. The residue was dried under reduced pressure at room temperature to give the title compound (254 g) in the yield of 98%.

$^1$H-NMR (DMSO-D$_6$) δ: 1.15 (d, 3H, J=7.2 Hz), 2.50-2.58 (m, 1H), 2.73-2.83 (m, 1H), 3.18-3.25 (m, 1H), 3.30-3.38 (m, 1H), 3.75 (s, 3H), 3.77 (s, 3H), 4.19-4.35 (m, 2H), 6.48 (dd, 1H, J=8.4, 2.3 Hz), 6.56 (d, 1H, J=2.3 Hz), 7.00 (d, 1H, J=8.4 Hz), 12.61 (br s, 1H).

(Step A-6) Preparation of (3R,4R)-4-methyl-5-oxopyrrolidine-3-carboxylic acid

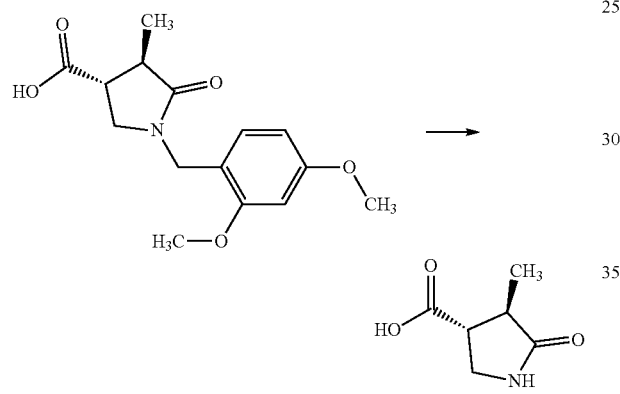

To a mixture of (3R,4R)-1-(2,4-dimethoxybenzyl)-4-methyl-5-oxopyrrolidine-3-carboxylic acid (254 g) obtained in Step A-5 and that compound (33 g) obtained in a similar manner to Step A-5 was added a solution of anisole (160 mL) in trifluoroacetic acid (1.44 L) at room temperature under nitrogen flow. The reaction mixture was stirred at 80° C. for 4 hours 4 minutes. The reaction mixture was cooled with water to room temperature. The reaction mixture was concentrated. To the residue was added toluene (287 mL), and the mixture was concentrated. The residue was let stand at room temperature overnight. To the residue was added toluene (287 mL), and the mixture was concentrated. To the residue was added toluene (80 mL) at room temperature. To the mixture was added diisopropyl ether (2.9 L) under water cooling. The mixture was stirred under water cooling. A solid precipitated from the mixture was collected by filtration and washed with diisopropyl ether (431 mL). The solid was dried under ambient pressure at room temperature to give the title compound (137 g) in 98% yield.

$^1$H-NMR (DMSO-D$_6$) δ: 1.10 (d, 3H, J=7.2 Hz), 2.35-2.44 (m, 1H), 2.79-2.87 (m, 1H), 3.19-3.25 (m, 1H), 3.34-3.40 (m, 1H), 7.64 (s, 1H), 12.56 (s, 1H).

[Reference Example B] Preparation of 5-hydrazinyl-2-(trifluoromethyl)pyrimidine

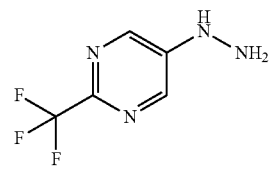 [SMILES: NNc1cnc(C(F)(F)F)nc1]

(Step B-1) Preparation of 5-hydrazinyl-2-(trifluoromethyl)pyrimidine

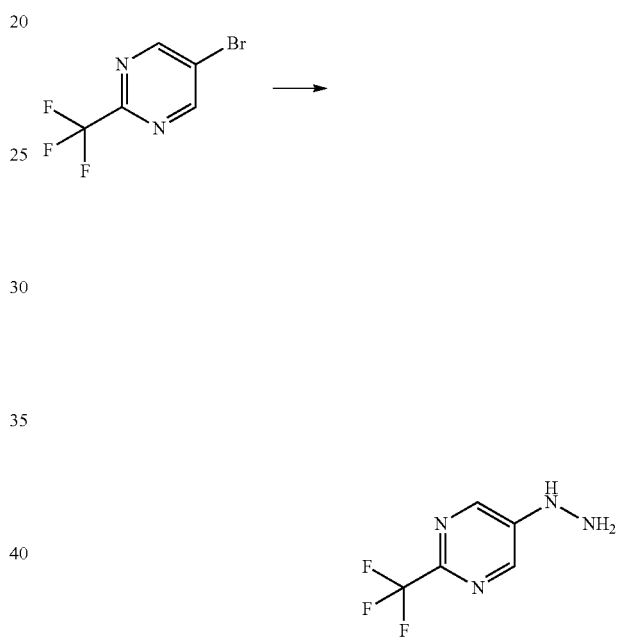

To 5-bromo-2-(trifluoromethyl)pyrimidine (2 g) were added hydrazine monohydrate (4.27 mL) and 2-propanol (1 mL) under argon atmosphere. The reaction mixture was stirred at 95° C. for 22 hours with explosion-proof shields. The reaction mixture was cooled to room temperature. To the reaction mixture were added water and saturated aqueous sodium hydrogen carbonate solution, and the mixture was extracted 5 times with ethyl acetate. The obtained organic layers were combined, washed with brine, dried over sodium sulfate, and concentrated. To the residue was added a mixture of n-hexane/ethyl acetate (3/1) at room temperature. The suspension was stirred at room temperature. A solid was filtered from the suspension and washed with a mixture of n-hexane/ethyl acetate (3/1). The solid was dried under reduced pressure at room temperature to give the title compound (647 mg) in 41% yield.

$^1$H-NMR (DMSO-D$_6$) δ: 4.43 (br s, 2H), 7.94 (br s, 1H), 8.33 (s, 2H).

[Example 1] Synthesis of (3R,4R)—N-(5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)-4-methyl-5-oxopyrrolidine-3-carboxamide

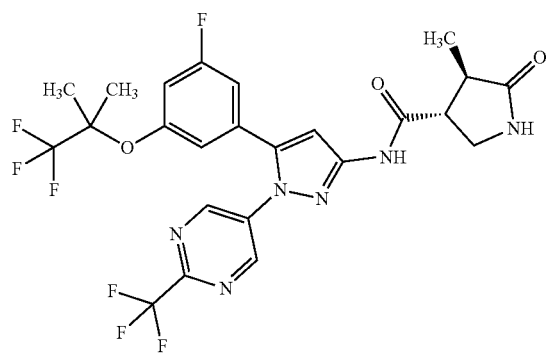 [SMILES: C[C@H]1C(=O)NC[C@@H]1C(=O)Nc1cc(-c2cc(F)cc(OC(C)(C)C(F)(F)F)c2)n(-c2cnc(C(F)(F)F)nc2)n1]

(Step 1-1) Preparation of 1-bromo-3-fluoro-5-((1,1,1-trifluoro-2-methylpropan-2-yl)oxy)benzene

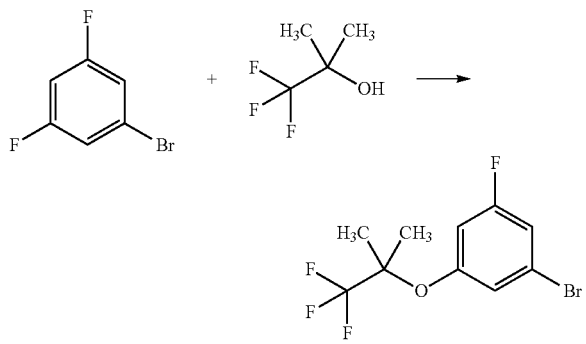

To a solution of 1-bromo-3,5-difluorobenzene (5.97 mL) in 1,3-dimethyl-2-imidazolidinone (10 mL) was added sodium hydride (4.14 g) at room temperature under nitrogen flow. To the mixture was added dropwise 1,1,1-trifluoro-2-methylpropan-2-ol (8 mL) under water cooling. To the reaction mixture was added 1,3-dimethyl-2-imidazolidinone (2 mL) at room temperature. To the reaction mixture was added dropwise 1,1,1-trifluoro-2-methylpropan-2-ol (3.16 mL) at room temperature. The total addition of these alcohols by dropping took 45 minutes. The reaction mixture was stirred at room temperature for 20 minutes, at 80° C. for 20 minutes, at 100° C. for 20 minutes, and at 130° C. for 20 hours 40 minutes. To the reaction mixture was added water under ice cooling. The mixture was extracted 3 times with n-hexane. The obtained organic layers were combined, washed 3 times with water, washed with brine, dried over sodium sulfate, and concentrated under reduced pressure of 140 mmHg at 35° C. The residue was purified by silica gel column chromatography (eluent: n-hexane/ethyl acetate=100/0 to 0/100) to give the title compound (8.31 g; including 12% by weight of n-hexane) in 47% yield.

$^1$H-NMR (DMSO-D$_6$) δ: 1.46 (s, 6H), 7.08 (dt, 1H, J=10.2, 2.1 Hz), 7.18 (s, 1H), 7.39-7.45 (m, 1H).

(Step 1-2) Preparation of 1-(1-butoxyvinyl)-3-fluoro-5-((1,1,1-trifluoro-2-methylpropan-2-yl)oxy)benzene

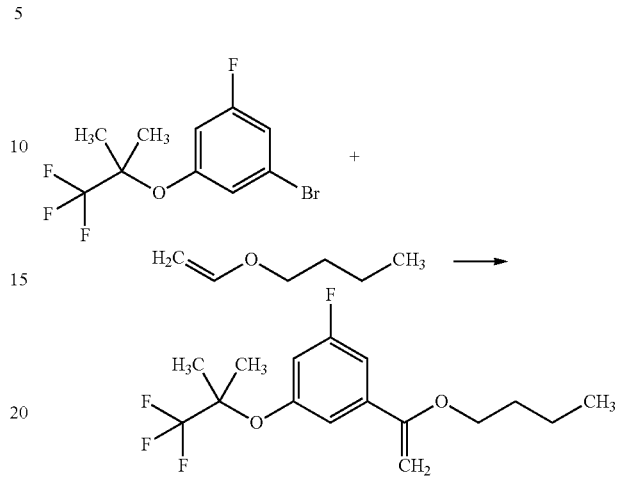

To a solution of a mixture of 1-bromo-3-fluoro-5-((1,1,1-trifluoro-2-methylpropan-2-yl)oxy)benzene (2.86 g; including 12% by weight of n-hexane) obtained in Step 1-1 and that compound obtained in a similar manner to Step 1-1 in ethylene glycol (69 mL) were added butylvinyl ether (19.77 mL), triethylamine (10.65 mL), 1,1'-bis(diphenylphosphino)ferrocene (1.271 g), and palladium (II) acetate (0.257 g) at room temperature. The reaction mixture was stirred at 110° C. under argon atmosphere for 19 hours. The reaction mixture was cooled to room temperature. To the reaction mixture were added water and n-hexane. The mixture was filtered through Celite. The filtrate was extracted twice with n-hexane. The obtained organic layers were combined, washed with water (twice) and brine, dried over magnesium sulfate, and concentrated under reduced pressure of 140 mmHg at 35° C. The residue was purified by silica gel column chromatography (eluent: n-hexane/ethyl acetate=100/0 to 95/5) to give the title compound (6.39 g; including 15% by weight of n-hexane) in 44% yield.

$^1$H-NMR (DMSO-D$_6$) δ: 0.95 (t, 3H, J=7.3 Hz), 1.40-1.51 (m, 2H), 1.44 (s, 6H), 1.69-1.76 (m, 2H), 3.84 (t, 2H, J=6.3 Hz), 4.39 (d, 1H, J=3.0 Hz), 4.90 (d, 1H, J=3.0 Hz), 6.96-7.01 (m, 1H), 7.12 (s, 1H), 7.24-7.29 (m, 1H).

(Step 1-3) Preparation of 1-(3-fluoro-5-((1,1,1-trifluoro-2-methylpropan-2-yl)oxy)phenyl)ethan-1-one

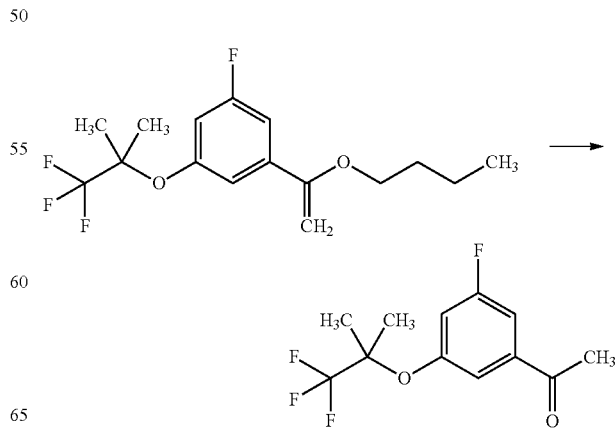

To a solution of 1-(1-butoxyvinyl)-3-fluoro-5-((1,1,1-trifluoro-2-methylpropan-2-yl)oxy)benzene (6.39 g; including 15% by weight of n-hexane) obtained in Step 1-2 in THF (25 mL) was added 2N hydrochloric acid (12.71 mL) at 0° C. This reaction mixture was stirred for 1 hour 10 minutes at room temperature. The reaction mixture was adjusted to pH 12 by addition of 2N aqueous sodium hydroxide solution under ice cooling. The mixture was extracted twice with n-hexane. The obtained organic layers were combined and washed twice with brine, dried over sodium sulfate, and concentrated under reduced pressure of 120 mmHg at 35° C. The residue was purified by silica gel column chromatography (eluent: n-hexane/ethyl acetate=98/2 to 85/15) to give the title compound (4.09 g; including 6% by weight of n-hexane) in 86% yield.

$^1$H-NMR (DMSO-D$_6$) δ: 1.47 (s, 6H), 2.60 (s, 3H), 7.32 (dt, 1H, J=9.7, 2.3 Hz), 7.42-7.43 (m, 1H), 7.58-7.62 (m, 1H).

(Step 1-4) Preparation of ethyl 4-(3-fluoro-5-((1,1,1-trifluoro-2-methylpropan-2-yl)oxy)phenyl)-2,4-dioxobutanoate

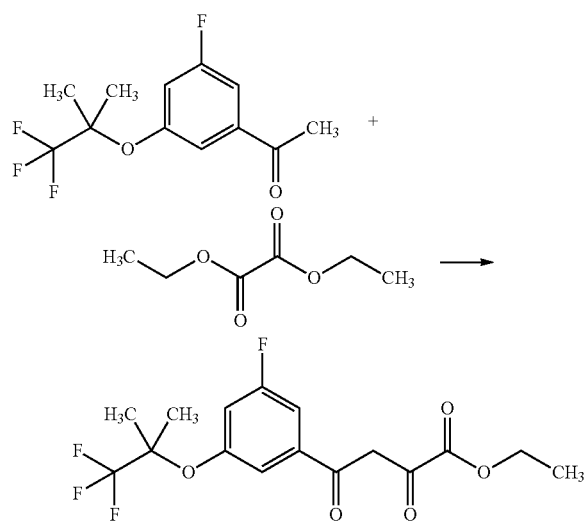

To a solution of 1-(3-fluoro-5-((1,1,1-trifluoro-2-methylpropan-2-yl)oxy)phenyl)ethan-1-one (4.09 g; including 6% by weight of n-hexane) obtained in Step 1-3 in THF (38.4 mL) were added diethyl oxalate (2.171 mL) under argon atmosphere. To the mixture was added lithium tert-butoxide (1.396 g) at 0° C. The reaction mixture was stirred at 0° C. for 3 hours 10 minutes. The reaction mixture was adjusted to pH 1 by addition of 1N hydrochloric acid under ice cooling. To the mixture was added water, and the mixture was extracted twice with ethyl acetate. The obtained organic layers were washed twice with brine and dried over sodium sulfate. The organic layer was concentrated to give the title compound (5.53 g; including 4% by weight of diethyl oxalate and 6% by weight of ethyl acetate) in 94% yield.

$^1$H-NMR (CDCl$_3$) δ: 1.42 (t, 3H, J=7.5 Hz), 1.50 (s, 6H), 4.42 (q, 2H, J=7.5 Hz), 6.97 (s, 1H), 7.01 (dt, 1H, J=9.3, 2.2 Hz), 7.42-7.45 (m, 1H), 7.48 (dt, 1H, J=8.8, 2.2 Hz), 15.02 (br s, 1H).

(Step 1-5) Preparation of ethyl 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylate

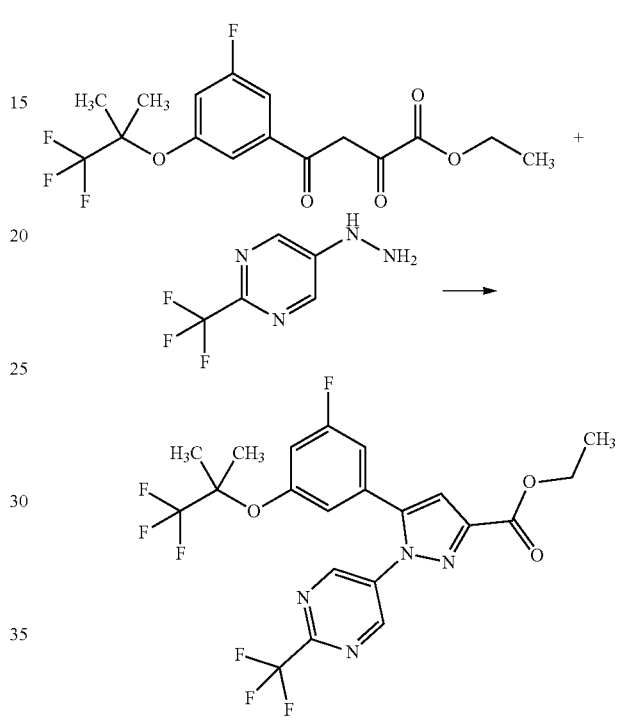

To a solution of ethyl 4-(3-fluoro-5-((1,1,1-trifluoro-2-methylpropan-2-yl)oxy)phenyl)-2,4-dioxobutanoate (500 mg; including 4% by weight of diethyl oxalate and 6% by weight of ethyl acetate) obtained in Step 1-4 in acetic acid (2.25 mL) was added 5-hydrazinyl-2-(trifluoromethyl)pyrimidine (242 mg) obtained in Step B-1 under argon atmosphere at room temperature. The reaction mixture was stirred at 100° C. for 21 hours and 30 minutes. The reaction mixture was let stand at room temperature over a weekend. The reaction mixture was concentrated. Acetic acid was azeotroped with toluene three times. The residue was purified by silica gel column chromatography (eluent: n-hexane/ethyl acetate=75/25 to 0/100) to give a crude product of the title compound. To the crude product was added a mixture of n-hexane/ethyl acetate (20/1) at room temperature. The suspension was stirred at room temperature. The solid was collected from the suspension by filtration and washed with a mixture of n-hexane/ethyl acetate (20/1). The obtained solid was dried under reduced pressure at room temperature to give the title compound (541 mg) in 86% yield.

$^1$H-NMR (DMSO-D$_6$) δ: 1.29 (s, 6H), 1.33 (t, 3H, J=7.1 Hz), 4.38 (q, 2H, J=7.1 Hz), 6.83-6.84 (m, 1H), 7.13 (dt, 1H, J=10.0, 2.3 Hz), 7.31-7.35 (m, 1H), 7.39 (s, 1H), 9.12 (s, 2H).

37

(Step 1-6) Preparation of 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylic acid

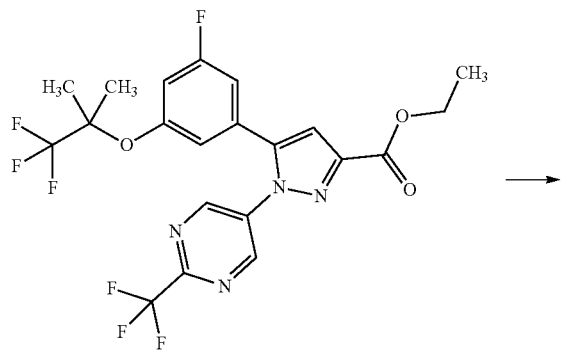

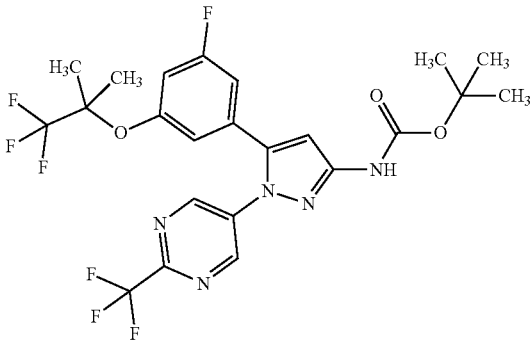

To a solution of ethyl 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylate (541 mg) obtained in Step 1-5 in THF (1.623 mL)/methanol (3.246 mL) was added 2N aqueous sodium hydroxide solution (1.068 mL) at room temperature. To the reaction mixture was added methanol (4 mL) at room temperature. The reaction mixture was stirred at room temperature for 25 hours 30 minutes. The reaction mixture was adjusted to pH 1 by addition of 1N hydrochloric acid under ice cooling. To the reaction mixture was added water, and the mixture was extracted twice with ethyl acetate. The obtained organic layers were combined, washed twice with brine, and dried over sodium sulfate. The organic layer was concentrated to give the title compound (504 mg) in 99% yield.

$^1$H-NMR (DMSO-D$_6$) δ: 1.29 (s, 6H), 6.84 (s, 1H), 7.11-7.15 (m, 1H), 7.30-7.34 (m, 2H), 9.10 (s, 2H), 13.35 (br s, 1H).

38

(Step 1-7) Preparation of tert-butyl (5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)carbamate

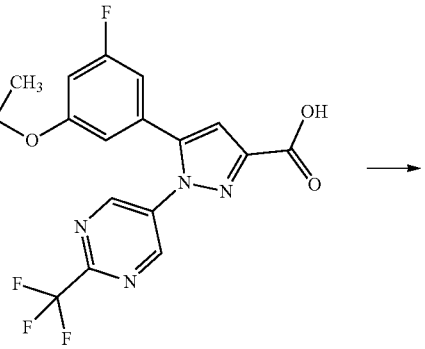

To a mixture of 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylic acid (495 mg) obtained in Step 1-6 in toluene (4.95 mL) were added triethylamine (0.346 mL) and diphenylphosphoryl azide (0.267 mL) under argon atmosphere at room temperature. The reaction mixture was stirred at room temperature for 1 hour. To the reaction mixture was added tert-butanol (4.26 mL) at room temperature. The reaction mixture was stirred at 100° C. for 27 hours 15 minutes. The reaction mixture was concentrated. The residue was purified by silica gel column chromatography (eluent: n-hexane/ethyl acetate=99/1 to 50/50) to give the title compound (315 mg) in 55% yield.

$^1$H-NMR (DMSO-D$_6$) δ: 1.32 (s, 6H), 1.48 (s, 9H), 6.85 (s, 1H), 6.92 (s, 1H), 7.09-7.14 (m, 1H), 7.27-7.31 (m, 1H), 8.90 (s, 2H), 10.18 (br s, 1H).

(Step 1-8) Preparation of 5-(3-fluoro-5-((1,1,1-trifluoro-2-methylpropan-2-yl)oxy)phenyl)-1-(2-(trifluoromethyl)pyrimidin-5-yl)-1H-pyrazol-3-amine (Step 1-9) Preparation of (3R,4R)—N-(5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)-4-methyl-5-oxopyrrolidine-3-carboxamide

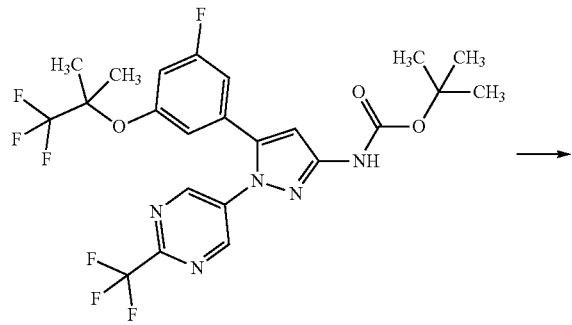

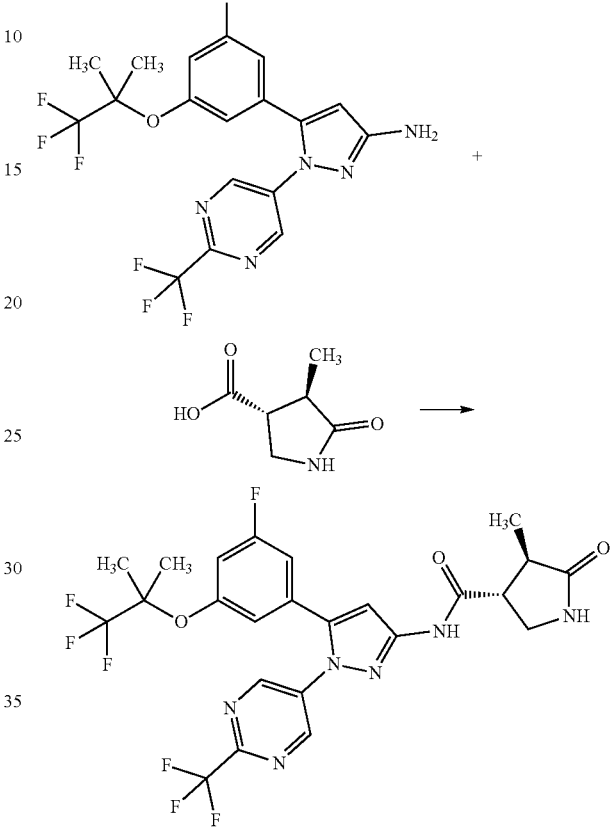

To tert-butyl (5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)carbamate (315 mg) obtained in Step 1-7 was added a solution of 4N hydrochloric acid in 1,4-dioxane (1.575 mL) at 0° C. under argon atmosphere. The reaction mixture was stirred at 0° C. for 10 minutes and stirred at room temperature for 27 hours 40 minutes. The reaction mixture was concentrated. To the residue was added a saturated aqueous sodium hydrogen carbonate solution, and the mixture was extracted twice with ethyl acetate. The obtained organic layers were combined, washed with brine, dried over sodium sulfate, and concentrated. The residue was purified by silica gel column chromatography (eluent: n-hexane/ethyl acetate=90/10 to 50/50) to give a solid. To the solid was added a mixture of n-hexane/ethyl acetate (10/1) at room temperature. The suspension was stirred at room temperature. The solid was collected from the suspension by filtration and washed with a mixture of n-hexane/ethyl acetate (10/1). The obtained solid was dried under reduced pressure at room temperature to give the title compound (224 mg) in 87% yield.

$^1$H-NMR (DMSO-D$_6$) δ: 1.34 (s, 6H), 5.50 (br s, 2H), 6.11 (s, 1H), 6.82-6.85 (m, 1H), 7.10 (dt, 1H, J=10.1, 2.3 Hz), 7.21-7.26 (m, 1H), 8.76 (s, 2H).

To a solution of 5-(3-fluoro-5-((1,1,1-trifluoro-2-methylpropan-2-yl)oxy)phenyl)-1-(2-(trifluoromethyl)pyrimidin-5-yl)-1H-pyrazol-3-amine (60 mg) obtained in Step 1-8 and (3R,4R)-4-methyl-5-oxopyrrolidine-3-carboxylic acid (21.0 mg) obtained in a similar manner to Step A-6 in pyridine (1 mL) was added WSC.HCl (28.2 mg) under argon atmosphere at room temperature. The reaction mixture was stirred at room temperature for 29 hours. The reaction mixture was concentrated. To the residue was added water, and the mixture was extracted with ethyl acetate. The obtained organic layer was sequentially washed with 1N hydrochloric acid (twice), water, saturated aqueous sodium hydrogen carbonate, and brine, dried over sodium sulfate, and concentrated. The residue was purified by silica gel thin-layer chromatography (eluent: ethyl acetate/methanol=50/1) to give the title compound (69 mg; including 4% by weight of ethyl acetate and 1% by weight of n-hexane) in 86% yield.

$^1$H-NMR (DMSO-D$_6$) δ: 1.09 (d, 3H, J=7.2 Hz), 1.32 (s, 6H), 2.50-2.59 (m, 1H), 3.03-3.11 (m, 1H), 3.20-3.27 (m, 1H), 3.43-3.50 (m, 1H), 6.85-6.87 (m, 1H), 7.13 (dt, 1H, J=9.9, 2.3 Hz), 7.17 (s, 1H), 7.27-7.32 (m, 1H), 7.68 (s, 1H), 8.95 (s, 2H), 11.20 (br s, 1H).

MS (M+H) 575, MS (M−H) 573

[Reference Example C] Preparation of 3-hydrazinyl-5-(trifluoromethyl)pyridine

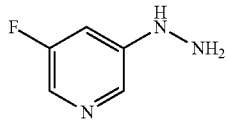

(Step C-1) Preparation of 3-fluoro-5-hydrazinylpyridine

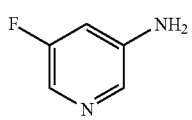

To a solution of 5-fluoropyridin-3-amine (1.5 g) in 6N hydrochloric acid (15 mL) was added a solution of sodium nitrite (0.923 g) in water (7.5 mL) dropwise over 2 minutes at 0° C. The reaction mixture was stirred at 0° C. for 1 hour 7 minutes. To the reaction mixture was added a suspension of tin (II) chloride (6.34 g) in 6N hydrochloric acid (15 mL) dropwise over 3 minutes at 0° C. The reaction mixture was stirred at 0° C. for 30 minutes and at room temperature for 23 hours. To the reaction mixture was added dropwise 8N aqueous sodium hydroxide (about 34 mL) at 0° C. The mixture was stirred at 0° C. The mixture was extracted 8 times with ethyl acetate. The obtained organic layers were combined, washed with brine, dried over sodium sulfate, and concentrated. To the obtained residue was added a mixture of methyl tert-butyl ether (6 mL)/n-hexane (36 mL) at room temperature. The suspension was stirred at room temperature. The solid was collected from the suspension by filtration and washed with n-hexane. The solid was dried under reduced pressure at 60° C. to give the title compound (965.8 mg) in 57% yield.

$^1$H-NMR (CDCl$_3$) δ: 3.64 (br s, 2H), 5.41 (br s, 1H), 6.99 (dt, 1H, J=10.8, 2.5 Hz), 7.89 (d, 1H, J=2.5 Hz), 7.97-7.99 (m, 1H)

[Example 2] Synthesis of (3R,4R)—N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide

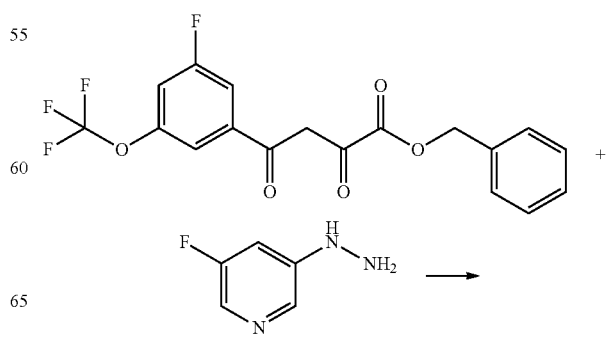

(Step 2-1) Preparation of Benzyl 4-(3-fluoro-5-(trifluoromethoxy)phenyl)-2,4-dioxobutanoate

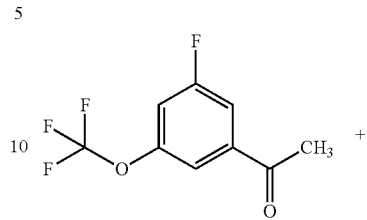

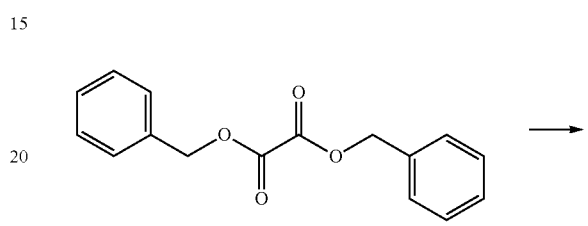

To a solution of 1-(3-fluoro-5-(trifluoromethoxy)phenyl)ethan-1-one (5 g) and dibenzyloxalate (6.69 g) in THF (50 mL) was added litium tert-butoxide (1.982 g) under ice cooling under argon atmosphere. The reaction mixture was stirred under ice cooling for 1 hour. To the reaction mixture were added 2N hydrochloric acid (12.5 mL), ethyl acetate, and water under ice cooling. The mixture was separated. The obtained organic layer was washed with brine and dried over sodium sulfate. The organic layer was concentrated to give a crude product of the title compound (11.7 g).

(Step 2-2) Preparation of benzyl 5-(3-fluoro-5-(trifluoromethoxy)phenyl)-1-(5-fluoropyridin-3-yl)-1H-pyrazole-3-carboxylate

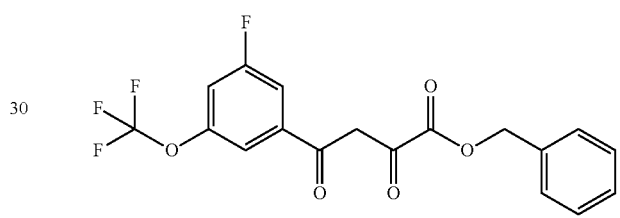

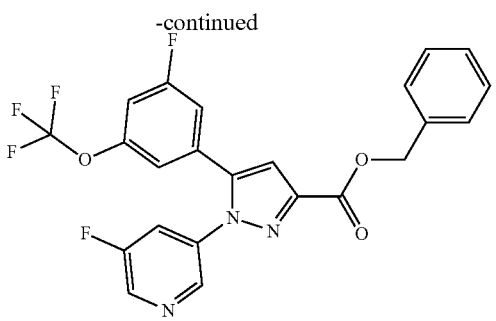

To a solution of the crude product (800 mg) of benzyl 4-(3-fluoro-5-(trifluoromethoxy)phenyl)-2,4-dioxobutanoate obtained in Step 2-1 in acetic acid (6 mL) was added 3-fluoro-5-hydrazinylpyridine (218 mg) obtained in Step C-1 under argon atmosphere at room temperature. The reaction mixture was stirred at 100° C. for 19 hours 42 minutes. The reaction mixture was cooled to room temperature and concentrated. To the residue was added toluene, and the mixture was concentrated. The residue was purified by silica gel column chromatography (eluent: n-hexane/ethyl acetate=90/10 to 69/31) to give the title compound (589.5 mg) in 79% yield for 2 steps.

$^1$H-NMR (CDCl$_3$) δ: 5.44 (s, 2H), 6.83-6.86 (m, 1H), 6.93 (ddd, 1H, J=8.4, 2.3, 1.6 Hz), 6.99-7.03 (m, 1H), 7.12 (s, 1H), 7.34-7.42 (m, 3H), 7.46-7.50 (m, 2H), 7.60 (ddd, 1H, J=8.6, 2.5, 1.8 Hz), 8.32 (d, 1H, J=1.8 Hz), 8.53 (d, 1H, J=2.5 Hz).

(Step 2-3) Preparation of 5-(3-fluoro-5-(trifluoromethoxy)phenyl)-1-(5-fluoropyridin-3-yl)-1H-pyrazole-3-carboxylic acid

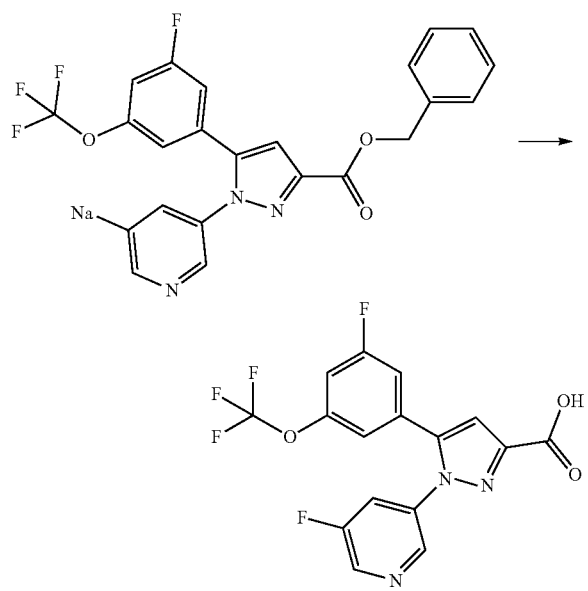

To a solution of benzyl 5-(3-fluoro-5-(trifluoromethoxy)phenyl)-1-(5-fluoropyridin-3-yl)-1H-pyrazole-3-carboxylate (589.5 mg) obtained in Step 2-2 in ethyl acetate (5.90 mL) was added 5% by weight of palladium on carbon (88 mg) under argon atmosphere at room temperature. The reaction mixture was stirred under 1 atm of hydrogen flow at room temperature for 2 hours. After the atmosphere was replaced with nitrogen, palladium on carbon was removed from the reaction mixture through Celite. The used Celite was washed with a mixture of ethyl acetate/methanol (9/1). The obtained filtrates were combined and concentrated. To the residue was added toluene, and the mixture was concentrated. The residue was dried under reduced pressure at room temperature to give the title compound (425.9 mg) in 89% yield.

$^1$H-NMR (DMSO-D$_6$) δ: 7.06-7.09 (m, 1H), 7.33 (s, 1H), 7.45 (ddd, 1H, J=9.2, 2.4, 1.5 Hz), 7.47-7.52 (m, 1H), 7.96 (ddd, 1H, J=9.2, 2.5, 2.1 Hz), 8.44-8.47 (m, 1H), 8.73 (d, 1H, J=2.5 Hz), 13.23 (br s, 1H).

(Step 2-4) Preparation of tert-butyl (5-(3-fluoro-5-(trifluoromethoxy)phenyl)-1-(5-fluoropyridin-3-yl)-1H-pyrazol-3-yl)carbamate

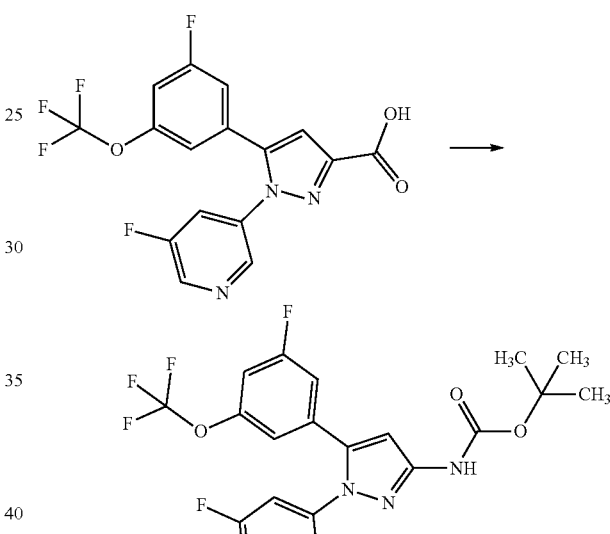

To a solution of 5-(3-fluoro-5-(trifluoromethoxy)phenyl)-1-(5-fluoropyridin-3-yl)-1H-pyrazole-3-carboxylic acid (425.9 mg) obtained in Step 2-3 and triethylamine (0.370 mL) in tert-butanol (4.26 mL)/toluene (8.52 mL) was added diphenylphosphoryl azide (0.286 mL) under argon atmosphere at room temperature. The reaction mixture was stirred at 110° C. for 14 hours 50 minutes. The reaction mixture was cooled to room temperature and concentrated. To the residue was added water, and the mixture was extracted with ethyl acetate. The obtained organic layer was washed with brine, dried over sodium sulfate, and concentrated. To the residue was added a mixture of n-hexane/ethyl acetate (1/1) at room temperature. The suspension was stirred at room temperature. Insoluble substances were filtered off and washed with a mixture of n-hexane/ethyl acetate (1/1). The obtained filtrates were combined and concentrated. The residue was purified by silica gel column chromatography (eluent: n-hexane/ethyl acetate=90/10 to 69/31) to give the title compound (207.4 mg) in 41% yield.

$^1$H-NMR (DMSO-D$_6$) δ: 1.48 (s, 9H), 6.90 (s, 1H), 7.06 (s, 1H), 7.40 (ddd, 1H, J=9.1, 2.4, 1.5 Hz), 7.44-7.49 (m, 1H), 7.73 (ddd, 1H, J=9.5, 2.5, 2.1 Hz), 8.32-8.34 (m, 1H), 8.61 (d, 1H, J=2.3 Hz), 10.05 (br s, 1H).

(Step 2-5) Preparation of 5-(3-fluoro-5-(trifluoromethoxy)phenyl)-1-(5-fluoropyridin-3-yl)-1H-pyrazol-3-amine (Step 2-6) Preparation of ((3R,4R)—N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide

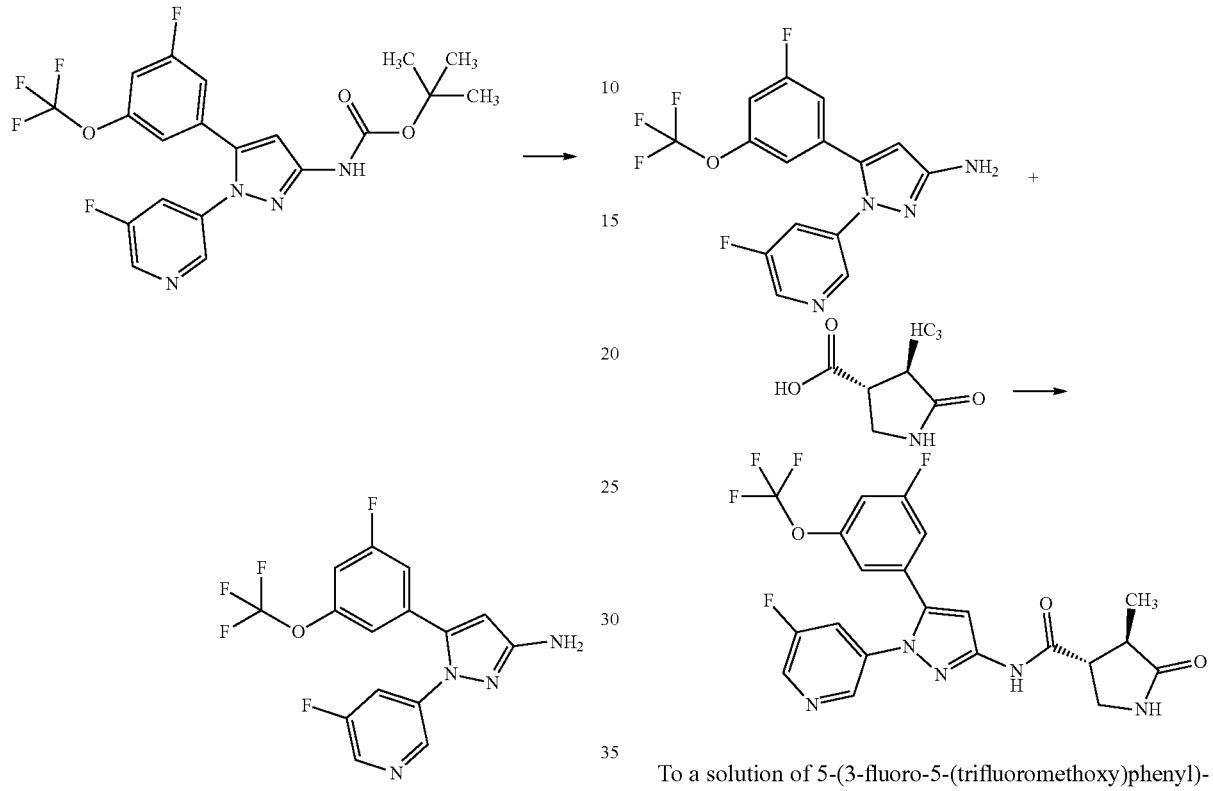

To tert-butyl (5-(3-fluoro-5-(trifluoromethoxy)phenyl)-1-(5-fluoropyridin-3-yl)-1H-pyrazol-3-yl)carbamate (207.4 mg) obtained in Step 2-4 was added trifluoroacetic acid (2.07 mL) under argon atmosphere at room temperature. The reaction mixture was stirred at room temperature for 22 hours 40 minutes. To the reaction mixture was added water at 0° C. To the mixture was added dropwise 8N aqueous sodium hydroxide solution (about 3.36 mL) at 0° C. To the mixture was added saturated aqueous sodium hydrogen carbonate solution at 0° C. The mixture was extracted with ethyl acetate. The obtained organic layer was washed with brine, dried over sodium sulfate, and concentrated. The residue was purified by silica gel column chromatography (eluent: n-hexane/ethyl acetate=64/36 to 43/57) to give a solid. To the solid was added n-hexane at room temperature. The suspension was stirred at room temperature. The solid was collected from the suspension by filtration and washed with n-hexane. The obtained solid was dried under reduced pressure at 60° C. to give the title compound (100.0 mg; including 0.21% by weight of ethyl acetate) in 62% yield.

$^1$H-NMR (CDCl$_3$) δ: 3.89 (br s, 2H), 6.00 (s, 1H), 6.86-6.89 (m, 1H), 6.93 (ddd, 1H, J=8.6, 2.3, 1.4 Hz), 6.96-7.00 (m, 1H), 7.43 (dt, 1H, J=9.2, 2.5 Hz), 8.20-8.22 (m, 1H), 8.36 (d, 1H, J=2.5 Hz).

To a solution of 5-(3-fluoro-5-(trifluoromethoxy)phenyl)-1-(5-fluoropyridin-3-yl)-1H-pyrazol-3-amine (38 mg; including 0.21% by weight of ethyl acetate) obtained in Step 2-5 and (3R,4R)-4-methyl-5-oxopyrrolidine-3-carboxylic acid (18.3 mg) obtained in a similar manner to Step A-6 in pyridine (0.380 mL) was added WSC.HCl (24.5 mg) under argon atmosphere at room temperature. The reaction mixture was stirred at room temperature for 2 hours 54 minutes. To the reaction mixture was added (3R,4R)-4-methyl-5-oxopyrrolidine-3-carboxylic acid (18 mg) obtained in a similar manner to Step A-6 and WSC.HCl (25 mg) at room temperature. The reaction mixture was stirred at room temperature overnight. To the reaction mixture was added 10% by weight of aqueous citric acid solution at room temperature, and the mixture was extracted with ethyl acetate. The obtained organic layer was washed with water and brine, dried over sodium sulfate, and concentrated. The residue was purified by silica gel thin-layer chromatography (eluent: ethyl acetate/methanol=97/3) to give the title compound. To the title compound was added a mixture of n-hexane/ethyl acetate at room temperature. The suspension was stirred at room temperature. The solid was collected from the suspension by filtration and washed with n-hexane. The obtained solid was dried under reduced pressure at 70° C. to give the title compound (46.6 mg; including 3.5% by weight of n-hexane) in 87% yield.

$^1$H-NMR (DMSO-D$_6$) δ: 1.09 (d, 3H, J=7.4 Hz), 2.49-2.59 (m, 1H), 3.01-3.10 (m, 1H), 3.20-3.26 (m, 1H), 3.42-3.49 (m, 1H), 7.06-7.08 (m, 1H), 7.16 (s, 1H), 7.42 (ddd, 1H, J=9.2, 2.3, 1.4 Hz), 7.46-7.51 (m, 1H), 7.68 (br s, 1H), 7.77 (ddd, 1H, J=9.7, 2.5, 2.1 Hz), 8.36-8.39 (m, 1H), 8.63 (d, 1H, J=2.5 Hz), 11.10 (br s, 1H).

MS (M+H) 482, MS (M−H) 480

(Step 2-7) Preparation of a monohydrate of ((3R,4R)—N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide

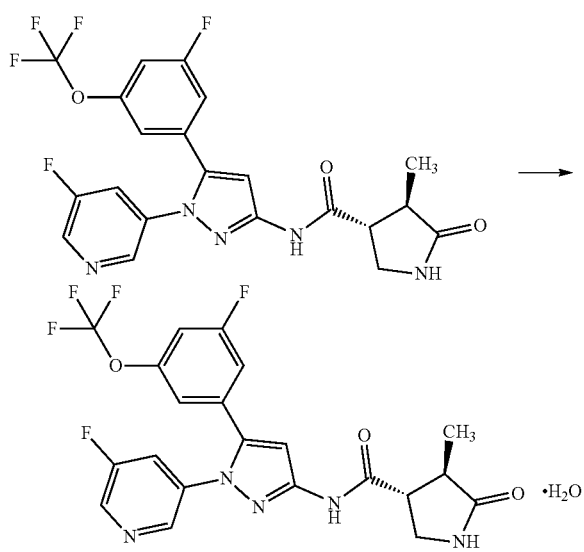

To ((3R,4R)—N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide (200 mg) was added ethanol (0.6 mL), and the mixture was heated at 60° C. to give a solution. The solution was cooled to room temperature. To the solution was added dropwise water (1.2 mL) at room temperature, and the mixture was stirred for 4 hours. The precipitated solid was collected by filtration and washed with a mixture of ethanol/water (=1/2). The obtained solid was dried under reduced pressure at 40° C. to give the title compound (192 mg) in 92% yield.

$^1$H-NMR (DMSO-D$_6$) δ: 1.09 (d, 3H, J=7.2 Hz), 2.48-2.60 (m, 1H), 3.00-3.10 (m, 1H), 3.20-3.27 (m, 1H), 3.41-3.49 (m, 1H), 7.05-7.09 (m, 1H), 7.16 (s, 1H), 7.42 (ddd, 1H, J=9.2, 2.3, 1.4 Hz), 7.47-7.52 (m, 1H), 7.69 (br s, 1H), 7.77 (ddd, 1H, J=9.6, 2.3, 2.1 Hz), 8.36-8.40 (m, 1H), 8.64 (d, 1H, J=2.3 Hz), 11.11 (br s, 1H).
Elemental analysis
Calculated: C 50.51 wt %, H 3.63 wt %, N 14.02 wt %
Observed: C 50.61 wt %, H 3.46 wt %, N 13.95 wt %

[Reference Example D] Preparation of 3-hydrazinyl-5-(trifluoromethyl)pyridine

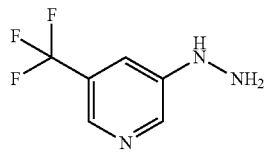 [SMILES: NNc1cncc(C(F)(F)F)c1]

(Step D-1) Preparation of 3-hydrazinyl-5-(trifluoromethyl)pyridine

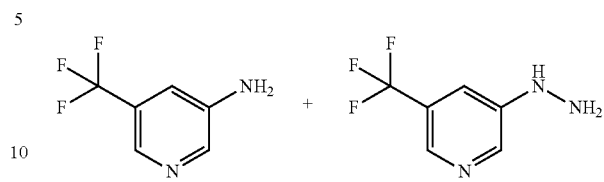

To a solution of 5-(trifluoromethyl)pyridin-3-amine (3 g) in 6N hydrochloric acid (30 mL) was added a solution of sodium nitrite (1.277 g) in water (15 mL) dropwise over 2 minutes at 0° C. The reaction mixture was stirred at 0° C. for 1 hour. To the reaction mixture was added a suspension of tin (II) chloride (8.77 g) in 6N hydrochloric acid (30 mL) dropwise over 3 minutes at 0° C. The reaction mixture was stirred at 0° C. for 28 minutes and at room temperature for 20 hours 9 minutes. To the reaction mixture was added 8N aqueous sodium hydroxide solution (about 68 mL) dropwise at 0° C. The mixture was stirred at 0° C. The mixture was extracted three times with ethyl acetate. The obtained organic layers were combined, washed with brine, dried over sodium sulfate, and concentrated. To the resulting residue was added a seed crystal of the title compound separately synthesized in a similar manner to this step. To the mixture was added a mixture of diisopropylether (2 mL)/n-hexane (30 mL) at room temperature. The suspension was stirred at room temperature. The solid was collected from the suspension by filtration and washed with n-hexane. The solid was dried under reduced pressure at room temperature to give the title compound (2.8464 g) in 87% yield.

$^1$H-NMR (CDCl$_3$) δ: 3.69 (br s, 2H), 5.49 (br s, 1H), 7.43-7.45 (m, 1H), 8.28-8.30 (m, 1H), 8.34 (d, 1H, J=2.8 Hz).

The seed crystal of the title compound used in Step D-1 was obtained by purifying a residue obtained in a similar manner to Step D-1 by silica gel column chromatography (eluent: n-hexane/ethyl acetate=1/1).

[Example 3] Synthesis of ((3R,4R)—N-(5-(3-fluoro-5-(trifluoromethoxy)phenyl)-1-(5-(trifluoromethyl)pyridin-3-yl)-1H-pyrazol-3-yl)-4-methyl-5-oxopyrrolidine-3-carboxamide

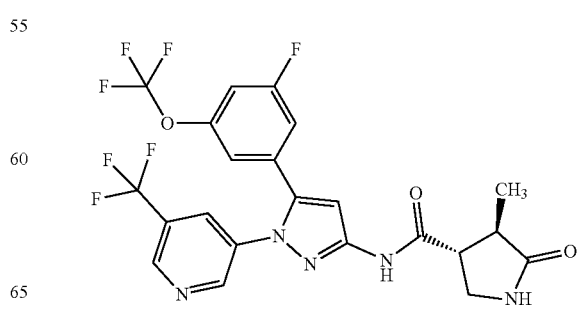

49

(Step 3-1) Preparation of benzyl 5-(3-fluoro-5-(trifluoromethoxy)phenyl)-1-(5-(trifluoromethyl)pyridin-3-yl)-1H-pyrazole-3-carboxylate

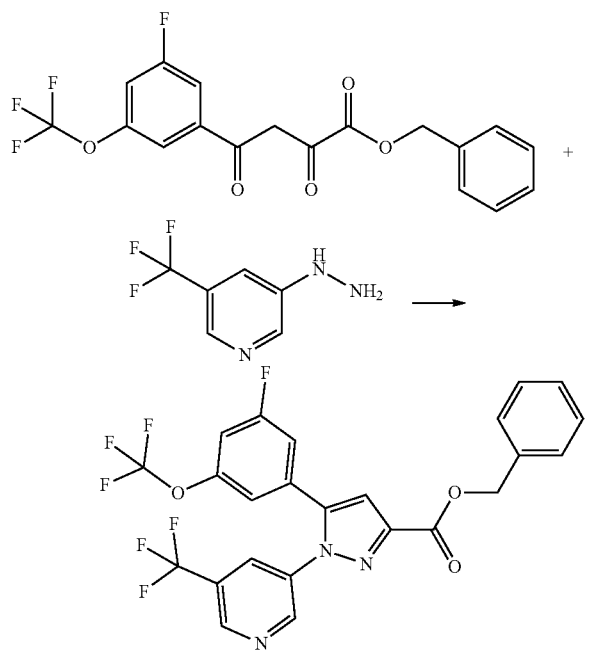

To a solution of a crude product (800 mg) of benzyl 4-(3-fluoro-5-(trifluoromethoxy)phenyl)-2,4-dioxobutanoate obtained in Step 2-1 in acetic acid (6 mL) was added 3-hydrazinyl-5-(trifluoromethyl)pyridine (304 mg) obtained in Step D-1 under argon atmosphere at room temperature. The reaction mixture was stirred at 100° C. for 22 hours 30 minutes. The reaction mixture was cooled to room temperature and concentrated. To the residue was added toluene and concentrated. This procedure was conducted again. The residue was purified by silica gel column chromatography (eluent: n-hexane/ethyl acetate=97/3 to 70/30) to give the title compound (640 mg) in 78% yield for 2 steps.

$^1$H-NMR (CDCl$_3$) δ: 5.45 (s, 2H), 6.80-6.83 (m, 1H), 6.94 (ddd, 1H, J=8.3, 2.3, 1.6 Hz), 7.00-7.05 (m, 1H), 7.14 (s, 1H), 7.33-7.42 (m, 3H), 7.46-7.50 (m, 2H), 8.04-8.07 (m, 1H), 8.69 (d, 1H, J=2.5 Hz), 8.88-8.92 (m, 1H).

(Step 3-2) Preparation of 5-(3-fluoro-5-(trifluoromethoxy)phenyl)-1-(5-(trifluoromethyl)pyridin-3-yl)-1H-pyrazole-3-carboxylic acid

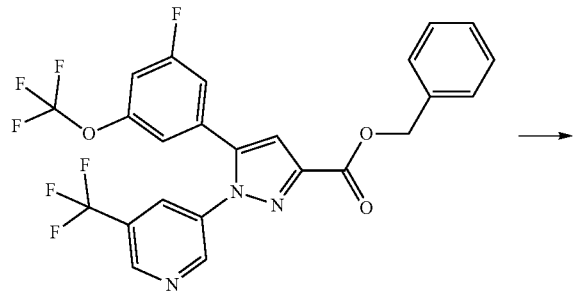

50

-continued

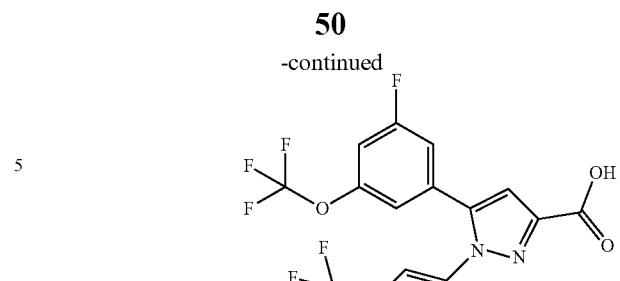

To a solution of benzyl 5-(3-fluoro-5-(trifluoromethoxy)phenyl)-1-(5-(trifluoromethyl)pyridin-3-yl)-1H-pyrazole-3-carboxylate (640 mg) obtained in Step 3-1 in ethyl acetate (6.4 mL) was added 5% by weight of palladium on carbon (32 mg) at room temperature. The reaction mixture was stirred under 1 atm of hydrogen atmosphere for 2 hours. After the atmosphere was replaced with nitrogen, THF was added to the reaction mixture. Palladium on carbon was removed from this reaction mixture through Celite. The used Celite was washed with THF. The obtained filtrates were combined and concentrated. To the residue was added n-hexane, and the mixture was concentrated. This procedure was conducted again. The residue was dried under reduced pressure at room temperature to give a crude product of the title compound (525 mg).

(Step 3-3) Preparation of tert-butyl (5-(3-fluoro-5-(trifluoromethoxy)phenyl)-1-(5-(trifluoromethyl)pyridin-3-yl)-1H-pyrazol-3-yl)carbamate

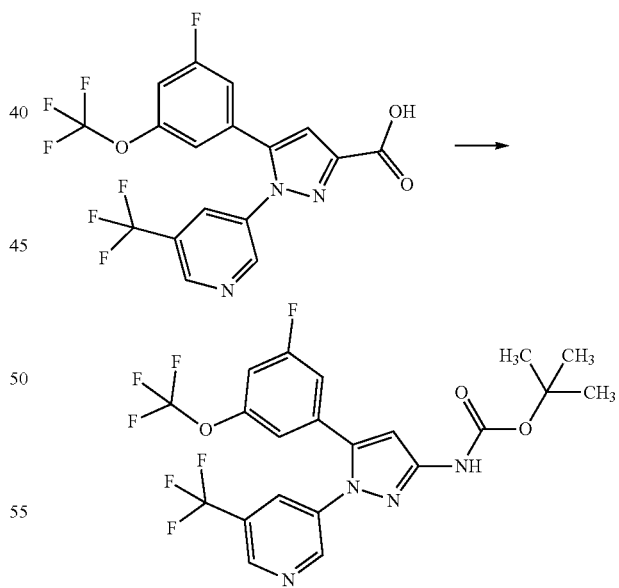

To a solution of the crude product (525 mg) of 5-(3-fluoro-5-(trifluoromethoxy)phenyl)-1-(5-(trifluoromethyl)pyridin-3-yl)-1H-pyrazole-3-carboxylic acid obtained in Step 3-2 and triethylamine (0.403 mL) in tert-butanol (5 mL)/toluene (10 mL) was added diphenylphosphoryl azide (0.311 mL) under argon atmosphere at room temperature. The reaction mixture was stirred at 100° C. for 16 hours. The reaction mixture was cooled to room temperature and concentrated. The residue was purified by silica gel column chromatography (eluent: n-hexane/ethyl acetate=97/3 to 70/30) to give the title compound (420 mg) in 68% yield for 2 steps. Formation of the title compound was confirmed by thin-layer chromatography (eluent: n-hexane/ethyl acetate=4/1, Rf value: 0.46).

(Step 3-4) Preparation of 5-(3-fluoro-5-(trifluoromethoxy)phenyl)-1-(5-(trifluoromethyl)pyridin-3-yl)-1H-pyrazol-3-amine

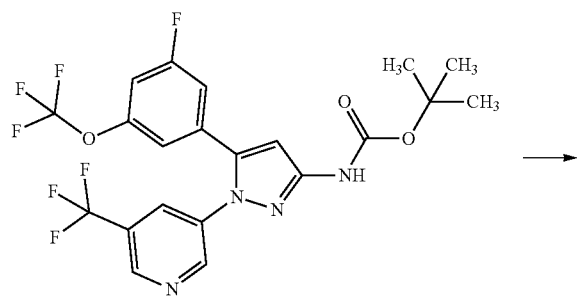

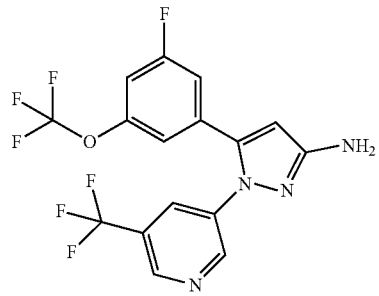

To tert-butyl (5-(3-fluoro-5-(trifluoromethoxy)phenyl)-1-(5-(trifluoromethyl)pyridin-3-yl)-1H-pyrazol-3-yl)carbamate (420 mg) obtained in Step 3-3 was added trifluoroacetic acid (3 mL) at room temperature. The reaction mixture was stirred at room temperature for 1 hour 30 minutes. The reaction mixture was concentrated. To the residue was added toluene, and the mixture was concentrated. This procedure was conducted again. To the residue were added ethyl acetate and saturated aqueous sodium hydrogen carbonate solution. The mixture was separated. The obtained organic layer was washed with brine, dried over sodium sulfate, and concentrated. The residue was purified by silica gel column chromatography (eluent: n-hexane/ethyl acetate=92/8 to 20/80) to give the title compound (313 mg) in 93% yield.

$^1$H-NMR (CDCl$_3$) δ: 3.92 (br s, 2H), 6.03 (s, 1H), 6.84-6.87 (m, 1H), 6.94 (ddd, 1H, J=8.4, 2.2, 1.3 Hz), 6.97-7.02 (m, 1H), 7.87-7.90 (m, 1H), 8.57 (d, 1H, J=2.4 Hz), 8.71-8.74 (m, 1H).

(Step 3-5) Preparation of ((3R,4R)—N-(5-(3-fluoro-5-(trifluoromethoxy)phenyl)-1-(5-(trifluoromethyl)pyridin-3-yl)-1H-pyrazol-3-yl)-4-methyl-5-oxopyrrolidine-3-carboxamide

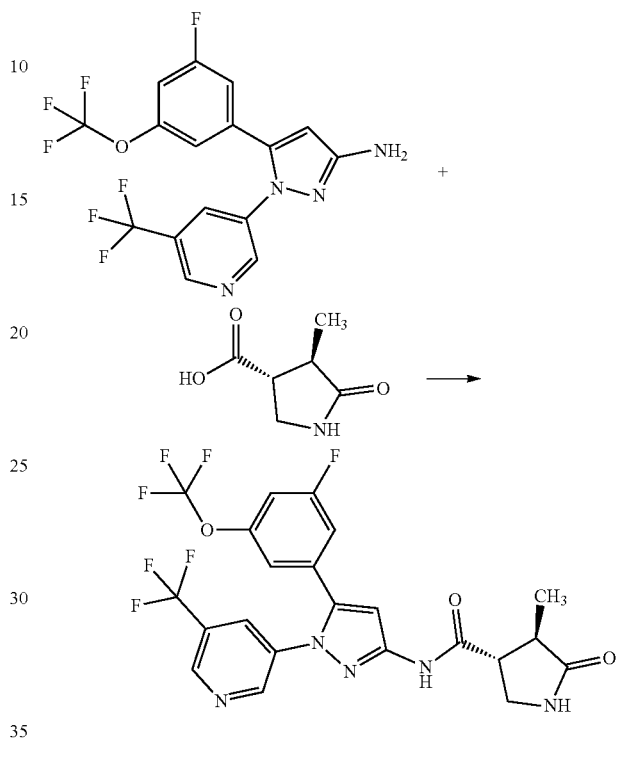

To a solution of 5-(3-fluoro-5-(trifluoromethoxy)phenyl)-1-(5-(trifluoromethyl)pyridin-3-yl)-1H-pyrazol-3-amine (60 mg) obtained in Step 3-4 and (3R,4R)-4-methyl-5-oxopyrrolidine-3-carboxylic acid (23.3 mg) obtained in a similar manner to Step A-6 in pyridine (1 mL) was added WSC.HCl (31.1 mg) at room temperature. The reaction mixture was stirred for 15 hours 30 minutes at room temperature. To this reaction mixture were added water and ethyl acetate at room temperature. The mixture was separated. The obtained organic layer was washed with brine, dried over sodium sulfate, and concentrated. To the residue was added toluene, and the mixture was concentrated. This procedure was conducted again. The residue was purified by silica gel thin-layer chromatography (eluent: ethyl acetate) to give the title compound (75 mg) in 96% yield.

$^1$H-NMR (CDCl$_3$) δ: 1.35 (d, 3H, J=6.9 Hz), 2.85-2.95 (m, 1H), 2.99-3.09 (m, 1H), 3.55-3.68 (m, 2H), 6.51 (br s, 1H), 6.87 (s, 1H), 6.96-7.06 (m, 2H), 7.23 (s, 1H), 7.80-7.85 (m, 1H), 8.73 (d, 1H, J=2.3 Hz), 8.81-8.85 (m, 1H), 9.13 (br s, 1H).

MS (M+H) 532, MS (M−H) 530

The other example compounds were obtained in a similar manner to the general preparation and examples above, and if needed, any other known methods. The following tables show structures and physical property data for the compounds of Examples 1 to 38.

| Example | Structure |
|---|---|
| 1 | 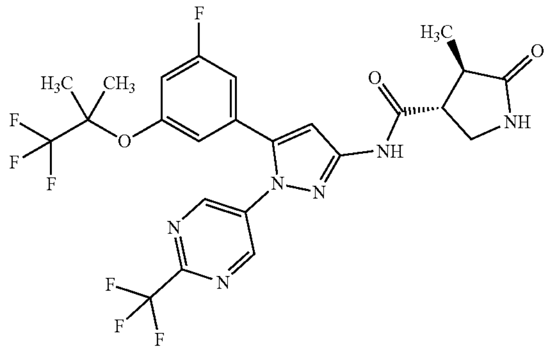 [SMILES: C[C@H]1C(=O)NC[C@@H]1C(=O)Nc1cc(-c2cc(F)cc(OC(C)(C)C(F)(F)F)c2)n(-c2cnc(C(F)(F)F)nc2)n1] |
| 2 | 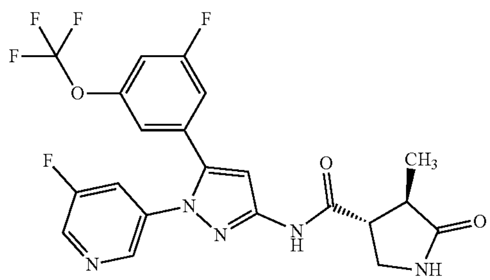 [SMILES: C[C@H]1C(=O)NC[C@@H]1C(=O)Nc1cc(-c2cc(F)cc(OC(F)(F)F)c2)n(-c2cncc(F)c2)n1] |
| 3 | 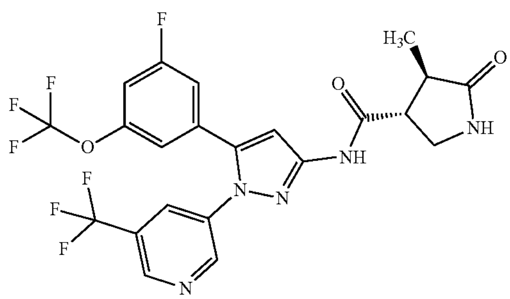 [SMILES: C[C@H]1C(=O)NC[C@@H]1C(=O)Nc1cc(-c2cc(F)cc(OC(F)(F)F)c2)n(-c2cncc(C(F)(F)F)c2)n1] |
| 4 | 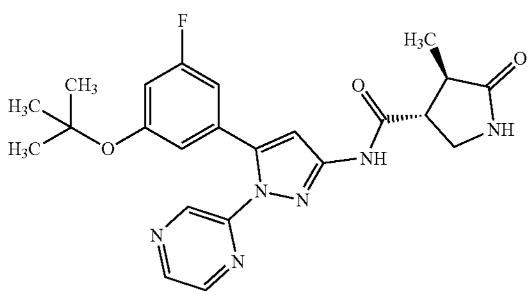 [SMILES: C[C@H]1C(=O)NC[C@@H]1C(=O)Nc1cc(-c2cc(F)cc(OC(C)(C)C)c2)n(-c2cnccn2)n1] |
| 5 | 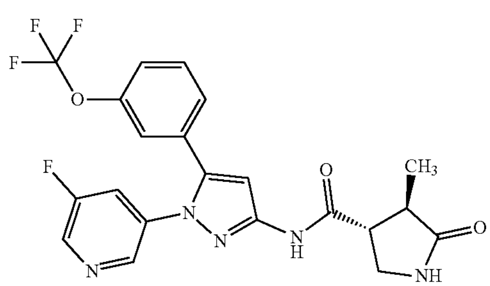 [SMILES: C[C@H]1C(=O)NC[C@@H]1C(=O)Nc1cc(-c2cccc(OC(F)(F)F)c2)n(-c2cncc(F)c2)n1] |

-continued
| Example | Structure |
|---|---|
| 6 | 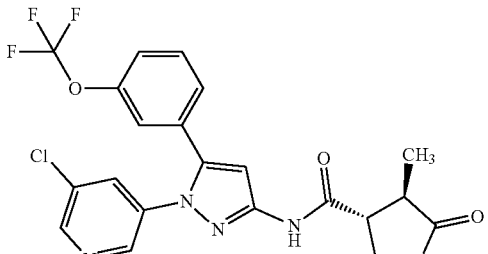 |
| 7 | 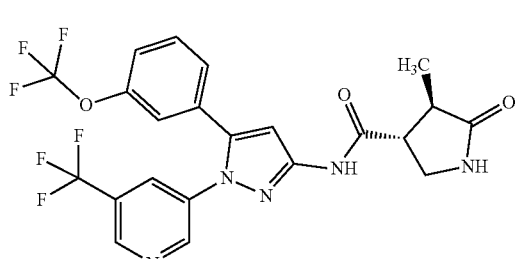 |
| 8 | 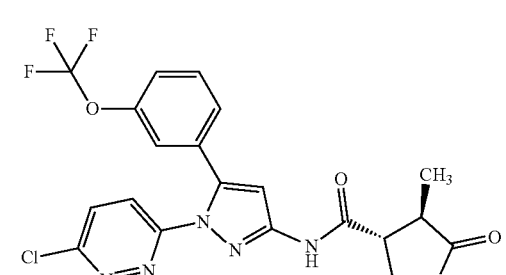 |
| 9 | 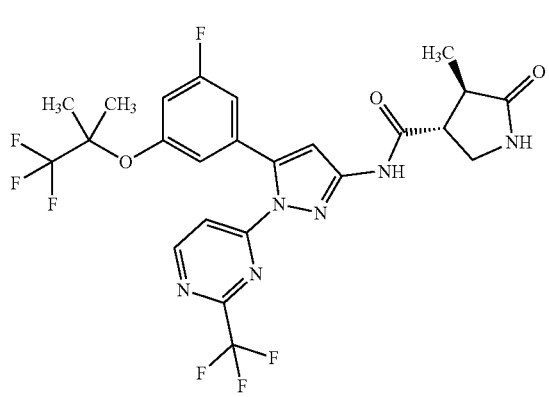 [SMILES: C[C@H]1C(=O)NC[C@@H]1C(=O)Nc1cc(-c2cc(F)cc(OC(C)(C)C(F)(F)F)c2)n(-c2ccnc(C(F)(F)F)n2)n1] |
| 10 | 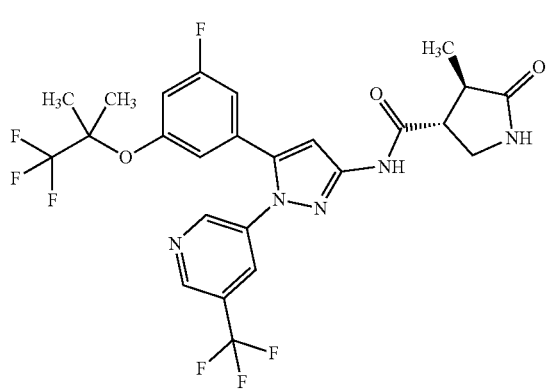 [SMILES: C[C@H]1C(=O)NC[C@@H]1C(=O)Nc1cc(-c2cc(F)cc(OC(C)(C)C(F)(F)F)c2)n(-c2cncc(C(F)(F)F)c2)n1] |

-continued
| Example | Structure |
|---|---|
| 11 | 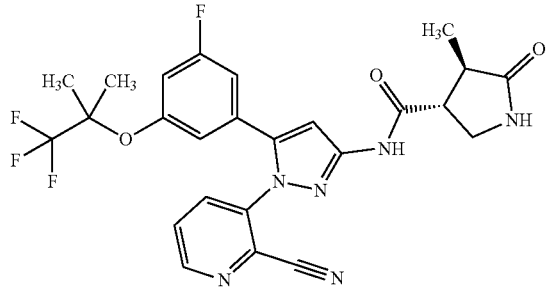 [SMILES: C[C@H]1C(=O)NC[C@@H]1C(=O)Nc1cc(-c2cc(F)cc(OC(C)(C)C(F)(F)F)c2)n(-c2cccnc2C#N)n1] |
| 12 | 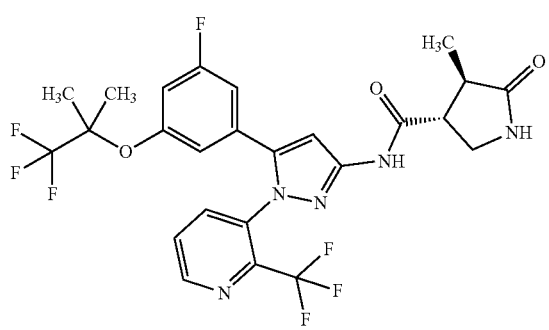 [SMILES: C[C@H]1C(=O)NC[C@@H]1C(=O)Nc1cc(-c2cc(F)cc(OC(C)(C)C(F)(F)F)c2)n(-c2cccnc2C(F)(F)F)n1] |
| 13 | 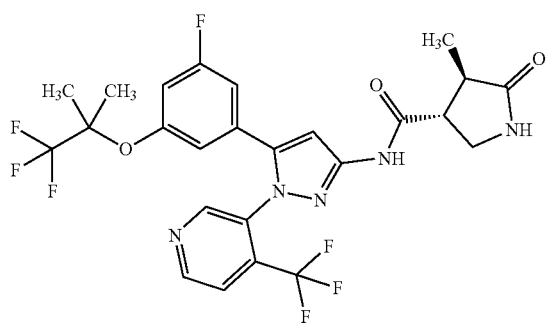 [SMILES: C[C@H]1C(=O)NC[C@@H]1C(=O)Nc1cc(-c2cc(F)cc(OC(C)(C)C(F)(F)F)c2)n(-c2cnccc2C(F)(F)F)n1] |
| 14 | 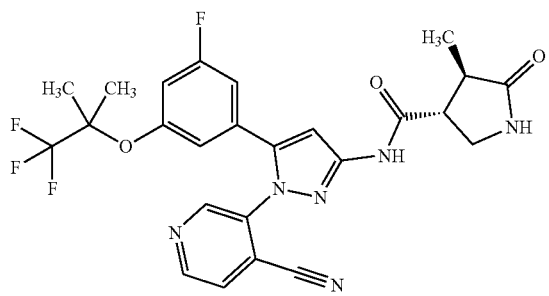 [SMILES: C[C@H]1C(=O)NC[C@@H]1C(=O)Nc1cc(-c2cc(F)cc(OC(C)(C)C(F)(F)F)c2)n(-c2cnccc2C#N)n1] |
| 15 | 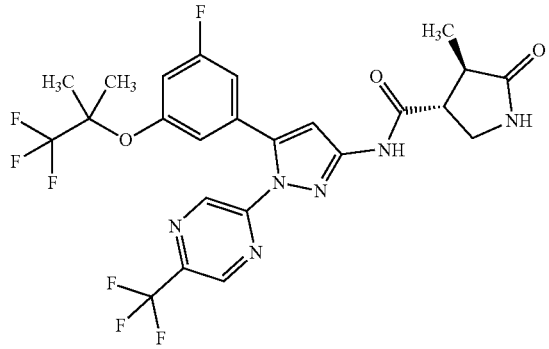 [SMILES: C[C@H]1C(=O)NC[C@@H]1C(=O)Nc1cc(-c2cc(F)cc(OC(C)(C)C(F)(F)F)c2)n(-c2cnc(C(F)(F)F)cn2)n1] |

| Example | Structure |
|---|---|
| 16 | 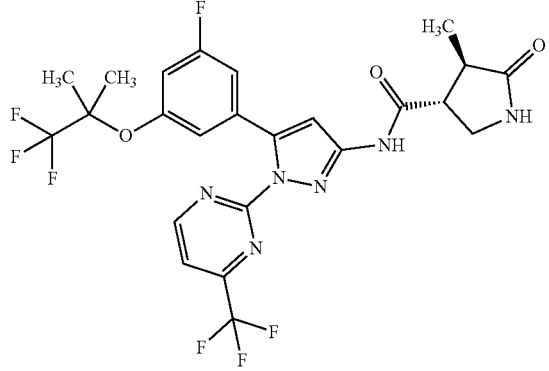 [SMILES: C[C@H]1C(=O)NC[C@@H]1C(=O)Nc1cc(-c2cc(F)cc(OC(C)(C)C(F)(F)F)c2)n(-c2nccc(C(F)(F)F)n2)n1] |
| 17 | 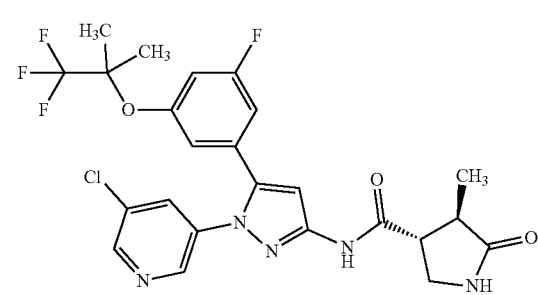 [SMILES: C[C@H]1C(=O)NC[C@@H]1C(=O)Nc1cc(-c2cc(F)cc(OC(C)(C)C(F)(F)F)c2)n(-c2cncc(Cl)c2)n1] |
| 18 | 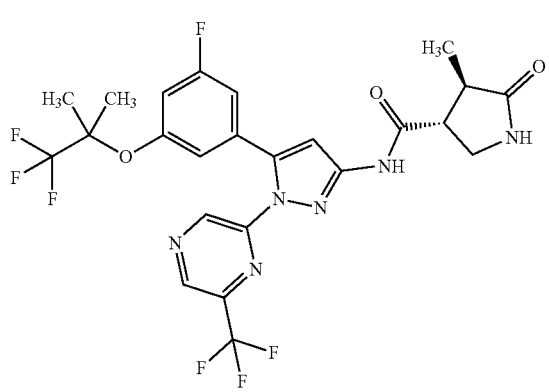 [SMILES: C[C@H]1C(=O)NC[C@@H]1C(=O)Nc1cc(-c2cc(F)cc(OC(C)(C)C(F)(F)F)c2)n(-c2cncc(C(F)(F)F)n2)n1] |
| 19 | 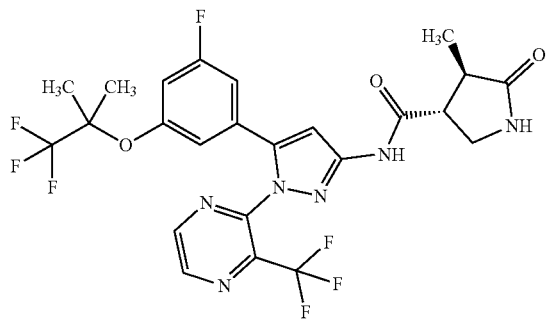 [SMILES: C[C@H]1C(=O)NC[C@@H]1C(=O)Nc1cc(-c2cc(F)cc(OC(C)(C)C(F)(F)F)c2)n(-c2nccnc2C(F)(F)F)n1] |

| Example | Structure |
|---|---|
| 20 | 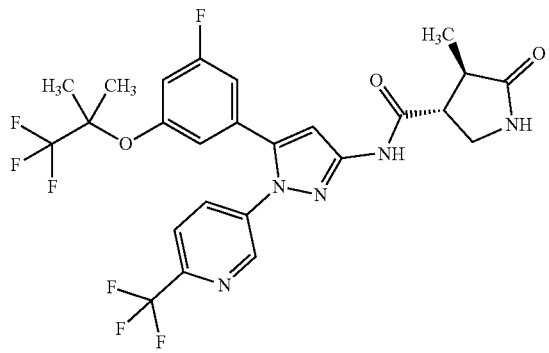 [SMILES: C[C@H]1C(=O)NC[C@@H]1C(=O)Nc1cc(-c2cc(F)cc(OC(C)(C)C(F)(F)F)c2)n(-c2ccc(C(F)(F)F)nc2)n1] |
| 21 | 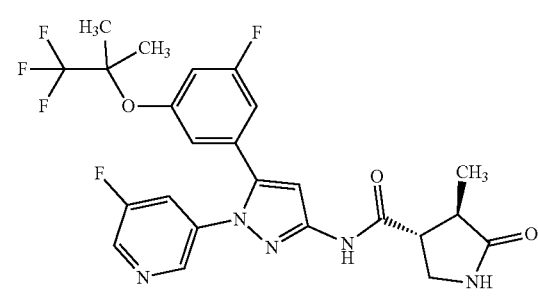 [SMILES: C[C@H]1C(=O)NC[C@@H]1C(=O)Nc1cc(-c2cc(F)cc(OC(C)(C)C(F)(F)F)c2)n(-c2cncc(F)c2)n1] |
| 22 | 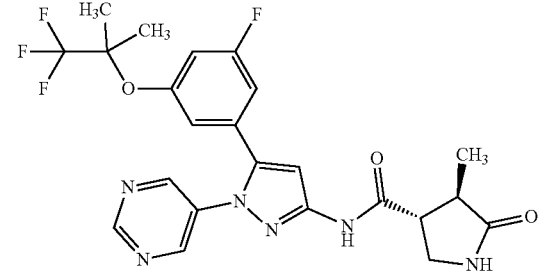 [SMILES: C[C@H]1C(=O)NC[C@@H]1C(=O)Nc1cc(-c2cc(F)cc(OC(C)(C)C(F)(F)F)c2)n(-c2cncnc2)n1] |
| 23 | 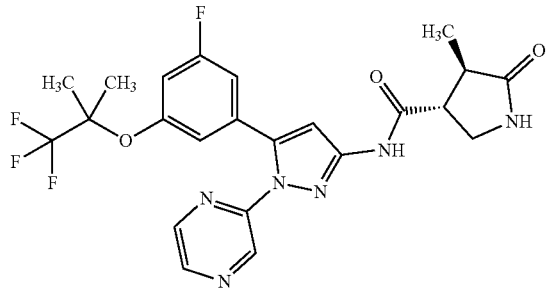 [SMILES: C[C@H]1C(=O)NC[C@@H]1C(=O)Nc1cc(-c2cc(F)cc(OC(C)(C)C(F)(F)F)c2)n(-c2cnccn2)n1] |
| 24 | 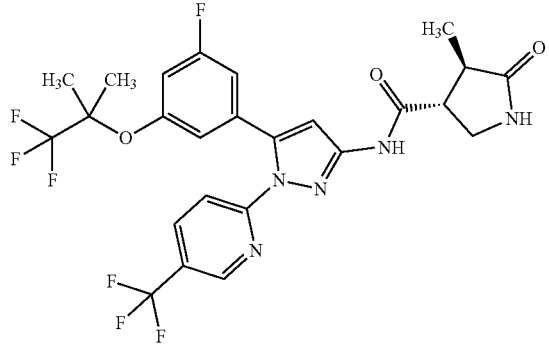 [SMILES: C[C@H]1C(=O)NC[C@@H]1C(=O)Nc1cc(-c2cc(F)cc(OC(C)(C)C(F)(F)F)c2)n(-c2ccc(C(F)(F)F)cn2)n1] |

| Example | Structure |
|---|---|
| 25 | 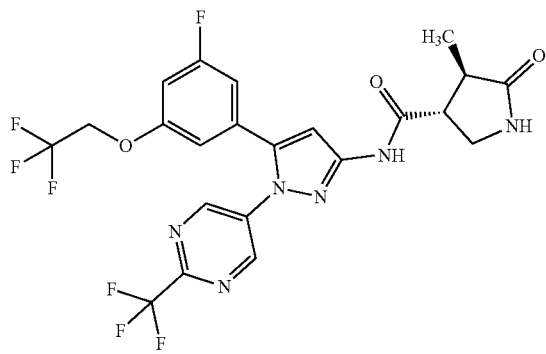 [SMILES: C[C@H]1C(=O)NC[C@@H]1C(=O)Nc1cc(-c2cc(F)cc(OCC(F)(F)F)c2)n(-c2cnc(C(F)(F)F)nc2)n1] |
| 26 | 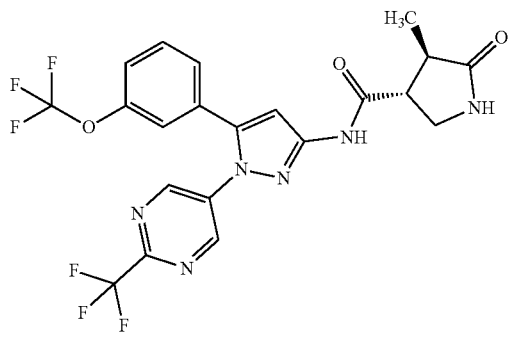 [SMILES: C[C@H]1C(=O)NC[C@@H]1C(=O)Nc1cc(-c2cccc(OC(F)(F)F)c2)n(-c2cnc(C(F)(F)F)nc2)n1] |
| 27 | 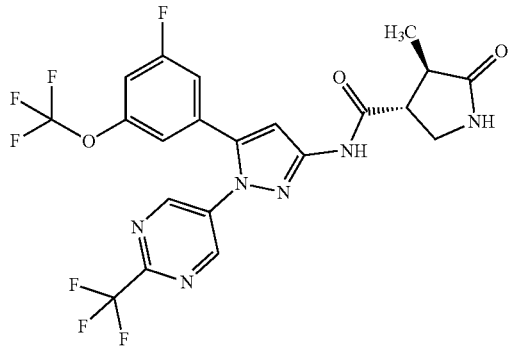 [SMILES: C[C@H]1C(=O)NC[C@@H]1C(=O)Nc1cc(-c2cc(F)cc(OC(F)(F)F)c2)n(-c2cnc(C(F)(F)F)nc2)n1] |
| 28 | 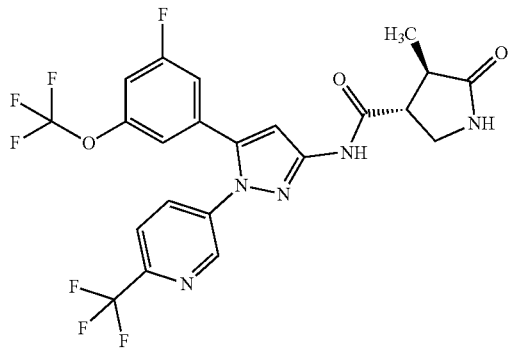 [SMILES: C[C@H]1C(=O)NC[C@@H]1C(=O)Nc1cc(-c2cc(F)cc(OC(F)(F)F)c2)n(-c2ccc(C(F)(F)F)nc2)n1] |

-continued
| Example | Structure |
|---|---|
| 29 | 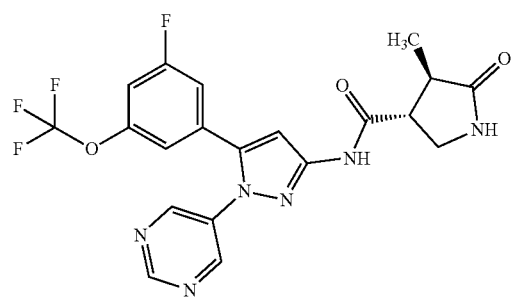 [SMILES: C[C@H]1C(=O)NC[C@@H]1C(=O)Nc1cc(-c2cc(F)cc(OC(F)(F)F)c2)n(-c2cncnc2)n1] |
| 30 | 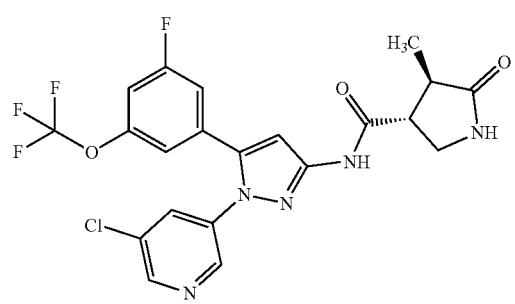 [SMILES: C[C@H]1C(=O)NC[C@@H]1C(=O)Nc1cc(-c2cc(F)cc(OC(F)(F)F)c2)n(-c2cncc(Cl)c2)n1] |
| 31 | 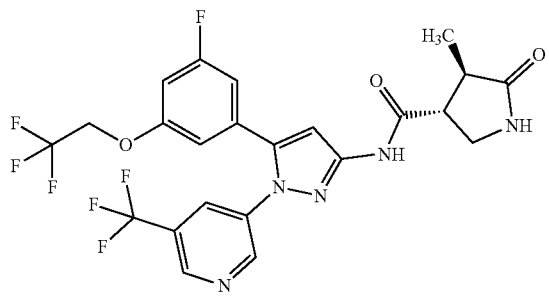 [SMILES: C[C@H]1C(=O)NC[C@@H]1C(=O)Nc1cc(-c2cc(F)cc(OCC(F)(F)F)c2)n(-c2cncc(C(F)(F)F)c2)n1] |
| 32 | 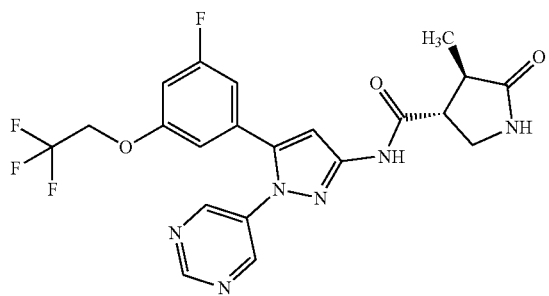 [SMILES: C[C@H]1C(=O)NC[C@@H]1C(=O)Nc1cc(-c2cc(F)cc(OCC(F)(F)F)c2)n(-c2cncnc2)n1] |
| 33 | 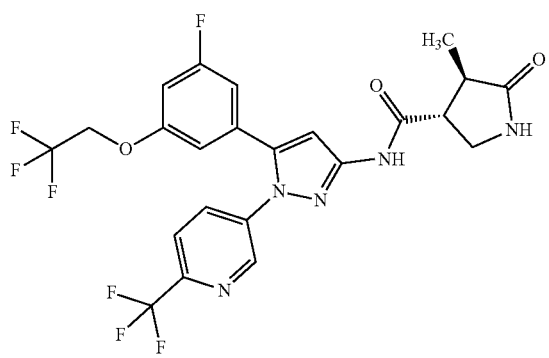 [SMILES: C[C@H]1C(=O)NC[C@@H]1C(=O)Nc1cc(-c2cc(F)cc(OCC(F)(F)F)c2)n(-c2ccc(C(F)(F)F)nc2)n1] |

-continued

| Example | Structure |
|---|---|
| 34 | 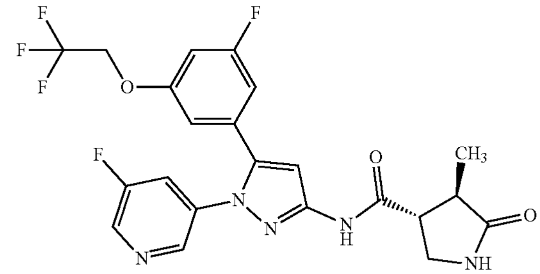 [SMILES: C[C@H]1C(=O)NC[C@@H]1C(=O)Nc1cc(-c2cc(F)cc(OCC(F)(F)F)c2)n(-c2cncc(F)c2)n1] |
| 35 | 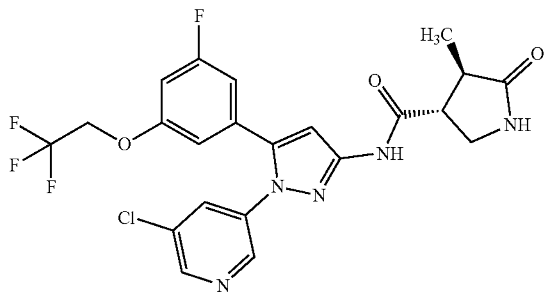 [SMILES: C[C@H]1C(=O)NC[C@@H]1C(=O)Nc1cc(-c2cc(F)cc(OCC(F)(F)F)c2)n(-c2cncc(Cl)c2)n1] |
| 36 | 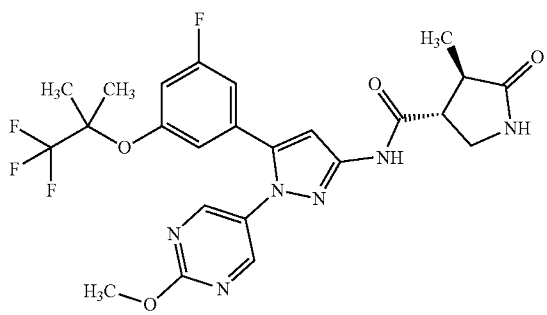 [SMILES: COc1ncc(-n2nc(NC(=O)[C@H]3CNC(=O)[C@@H]3C)cc2-c2cc(F)cc(OC(C)(C)C(F)(F)F)c2)cn1] |
| 37 | 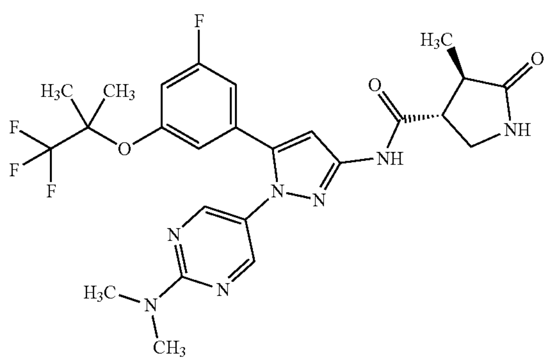 [SMILES: C[C@H]1C(=O)NC[C@@H]1C(=O)Nc1cc(-c2cc(F)cc(OC(C)(C)C(F)(F)F)c2)n(-c2cnc(N(C)C)nc2)n1] |
| 38 | 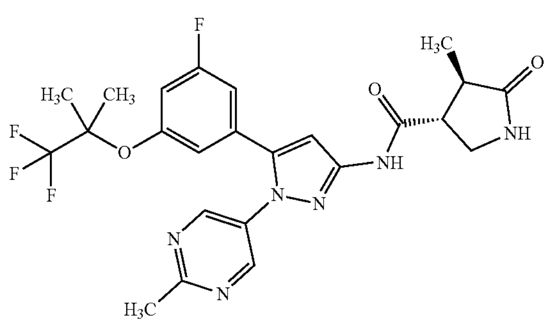 [SMILES: Cc1ncc(-n2nc(NC(=O)[C@H]3CNC(=O)[C@@H]3C)cc2-c2cc(F)cc(OC(C)(C)C(F)(F)F)c2)cn1] |

| Example | ¹H-NMR | MS (M + H) | MS (M − H) |
|---|---|---|---|
| 1 | ¹H-NMR (DMSO-D₆) δ: 1.09 (d, 3H, J = 7.2 Hz), 1.32 (s, 6H), 2.50-2.59 (m, 1H), 3.03-3.11 (m, 1H), 3.20-3.27 (m, 1H), 3.43-3.50 (m, 1H), 6.85-6.87 (m, 1H), 7.13 (dt, 1H, J = 9.9, 2.3 Hz), 7.17 (s, 1H), 7.27-7.32 (m, 1H), 7.68 (s, 1H), 8.95 (s, 2H), 11.20 (br s, 1H). | 575 | 573 |
| 2 | ¹H-NMR (DMSO-D₆) δ: 1.09 (d, 3H, J = 7.4 Hz), 2.49-2.59 (m, 1H), 3.01-3.10 (m, 1H), 3.20-3.26 (m, 1H), 3.42-3.49 (m, 1H), 7.06-7.08 (m, 1H), 7.16 (s, 1H), 7.42 (ddd, 1H, J = 9.2, 2.3, 1.4 Hz), 7.46-7.51 (m, 1H), 7.68 (br s, 1H), 7.77 (ddd, 1H, J = 9.7, 2.5, 2.1 Hz), 8.36-8.39 (m, 1H), 8.63 (d, 1H, J = 2.5 Hz), 11.10 (br s, 1H). | 482 | 480 |
| 3 | ¹H-NMR (CDCl₃) δ: 1.35 (d, 3H, J = 6.9 Hz), 2.85-2.95 (m, 1H), 2.99-3.09 (m, 1H), 3.55-3.68 (m, 2H), 6.51 (br s, 1H), 6.87 (s, 1H), 6.96-7.06 (m, 2H), 7.23 (s, 1H), 7.80-7.85 (m, 1H), 8.73 (d, 1H, J = 2.3 Hz), 8.81-8.85 (m, 1H), 9.13 (br s, 1H). | 532 | 530 |
| 4 | ¹H-NMR (DMSO-D₆) δ: 1.09 (d, 3H, J = 7.2 Hz), 1.20 (s, 9H), 2.52-2.57 (m, 1H), 3.06 (q, 1H, J = 8.6 Hz), 3.23 (t, 1H, J = 8.9 Hz), 3.46 (t, 1H, J = 8.6 Hz), 6.66 (t, 1H, J = 1.7 Hz), 6.86 (dt, 1H, J = 10.6, 2.3 Hz), 7.02 (dq, 1H, J = 9.2, 1.2 Hz), 7.05 (s, 1H), 7.68 (s, 1H), 8.36 (dd, 1H, J = 2.5, 1.4 Hz), 8.60 (d, 1H, J = 2.5 Hz), 8.98 (d, 1H, J = 1.4 Hz), 11.13 (s, 1H). | 453 | 451 |
| 5 | ¹H-NMR (DMSO-Ds) δ: 1.09 (d, 3H, J = 7.2 Hz), 2.53-2.57 (m, 1H), 3.05 (q, 1H, J = 8.6 Hz), 3.23 (t, 1H, J = 9.0 Hz), 3.45 (t, 1H, J = 8.6 Hz), 7.10 (s, 1H), 7.24 (s, 1H), 7.42 (dd, 2H, J = 7.6, 1.4 Hz), 7.58 (t, 1H, J = 8.1 Hz), 7.68 (s, 1H), 7.73 (dt, 1H, J = 9.6, 2.3 Hz), 8.34 (s, 1H), 8.61 (d, 1H, J = 2.5 Hz), 11.08 (s, 1H). | 464 | 462 |
| 6 | ¹H-NMR (DMSO-D₆) δ: 1.09 (d, 3H, J = 6.9 Hz), 2.51-2.58 (m, 1H), 3.05 (q, 1H, J = 8.6 Hz), 3.23 (t, 1H, J = 8.9 Hz), 3.45 (t, 1H, J = 8.6 Hz), 7.09 (s, 1H), 7.25 (s, 1H), 7.44 (dd, 2H, J = 7.7, 1.5 Hz), 7.59 (t, 1H, J = 8.1 Hz), 7.68 (s, 1H), 7.87 (t, 1H, J = 2.2 Hz), 8.42 (d, 1H, J = 2.3 Hz), 8.63 (d, 1H, J = 2.1 Hz), 11.08 (s, 1H). | 480 | 478 |
| 7 | H-NMR (DMSO-D₆) δ: 1.09 (d, 3H, J = 7.2 Hz), 2.51-2.59 (m, 1H), 3.06 (q, 1H, J = 8.6 Hz), 3.24 (t, 1H, J = 9.0 Hz), 3.46 (t, 1H, J = 8.4 Hz), 7.11 (s, 1H), 7.26 (s, 1H), 7.43-7.49 (m, 2H), 7.60 (t, 1H, J = 8.0 Hz), 7.68 (s, 1H), 8.01 (t, 1H, J = 2.0 Hz), 8.78 (d, 1H, J = 2.3 Hz), 8.96 (d, 1H, J = 0.9 Hz), 11.12 (s, 1H). | 514 | 512 |
| 8 | ¹H-NMR (DMSO-D₆) δ: 1.09 (d, 3H, J = 7.2 Hz), 2.53-2.59 (m, 1H), 3.07 (q, 1H, J = 8.6 Hz), 3.24 (t, 1H, J = 8.9 Hz), 3.46 (t, 1H, J = 8.6 Hz), 7.12 (s, 1H), 7.35 (s, 1H), 7.39-7.45 (m, 2H), 7.54 (t, 1H, J = 8.0 Hz), 7.68 (s, 1H), 8.08 (d, 1H, J = 9.2 Hz), 8.13 (d, 1H, J = 9.0 Hz) 11.15 (s, 1H). | 481 | 479 |
| 9 | ¹H-NMR (DMSO-D₆) δ: 1.10 (d, 3H, J = 7.2 Hz), 1.43 (d, 6H, J = 0.9 Hz), 2.50-2.58 (m, 1H), 3.09 (q, 1H, J = 8.7 Hz), 3.24 (t, 1H, J = 8.8 Hz), 3.47 (t, 1H, J = 8.6 Hz), 7.02 (t, 1H, J = 1.6 Hz), 7.07-7.10 (m, 2H), 7.23 (ddd, 1H, J = 9.4, 2.2, 1.4 Hz), 7.69 (br s, 1H), 7.96 (d, 1H, J = 5.8 Hz), 9.05 (d, 1H, J = 5.8 Hz), 11.28 (br s, 1H). | 575 | 573 |

-continued

| Example | ¹H-NMR | MS (M + H) | MS (M − H) |
|---|---|---|---|
| 10 | ¹H-NMR (DMSO-D$_6$) δ: 1.09 (d, 3H, J = 7.2 Hz), 1.29 (s, 6H), 2.50-2.58 (m, 1H), 3.05 (q, 1H, J = 8.4 Hz), 3.23 (t, 1H, J = 8.9 Hz), 3.45 (t, 1H, J = 8.4 Hz), 6.79 (t, 1H, J = 1.6 Hz), 7.07-7.12 (m, 2H), 7.20 (ddd, 1H, J = 9.0, 2.2, 1.4 Hz), 7.68 (br s, 1H), 8.10 (t, 1H, J = 2.0 Hz), 8.77 (d, 1H, J = 2.3 Hz), 8.96 (d, 1H, J = 1.2 Hz), 11.10 (br s, 1H). | 574 | 572 |
| 11 | ¹H-NMR (CDCl$_3$) δ: 1.34 (d, 3H, J = 6.9 Hz), 1.37 (s, 6H), 2.85-2.92 (m, 1H), 2.99 (ddd, 1H, J = 8.5, 8.5, 8.5 Hz), 3.58-3.67 (m, 2H), 5.84 (br s, 1H), 6.66-6.68 (m, 1H), 6.71-6.75 (m, 1H), 6.78 (dt, 1H, J = 9.6, 2.1 Hz), 7.23 (s, 1H), 7.55-7.61 (m, 1H), 7.63-7.67 (m, 1H), 8.54-8.57 (br m, 1H), 8.73 (dd, 1H, J = 4.5, 1.5 Hz). | 531 | 529 |
| 12 | ¹H-NMR (CDCl$_3$) δ: 1.28 (s, 6H), 1.33 (d, 3H, J = 6.9 Hz), 2.83-2.99 (m, 2H), 3.52-3.64 (m, 2H), 6.01 (br s, 1H), 6.55-6.58 (m, 1H), 6.71 (dt, 1H, J = 9.6, 2.3 Hz), 6.74-6.76 (m, 1H), 7.18 (s, 1H), 7.58-7.62 (m, 1H), 7.64-7.66 (m, 1H), 8.55 (br s, 1H), 8.81 (dd, 1H, J = 4.5, 1.3 Hz). | 574 | 572 |
| 13 | ¹H-NMR (DMSO-D$_6$) δ: 1.08 (d, 3H, J = 7.2 Hz), 1.21 (s, 6H), 2.54-2.60 (m, 1H), 3.06 (ddd, 1H, J = 8.4, 8.4, 8.4 Hz), 3.23 (dd, 1H, J = 8.4, 8.4 Hz), 3.45 (dd, 1H, J = 8.4, 8.4 Hz), 6.49-6.51 (m, 1H), 7.03 (dt, 1H, J = 9.9, 2.2 Hz), 7.07-7.11 (m, 1H), 7.19 (s, 1H), 7.67 (br s, 1H), 8.02 (d, 1H, J = 5.3 Hz), 8.86 (s, 1H), 8.99 (d, 1H, J = 5.3 Hz), 11.00 (br s, 1H). | 574 | 572 |
| 14 | ¹H-NMR (CDCl$_3$) δ: 1.33-1.39 (m, 9H), 2.85-3.01 (m, 2H), 3.57-3.68 (m, 2H), 5.83 (br s, 1H), 6.66-6.69 (m, 1H), 6.72-6.76 (m, 1H), 6.78 (dt, 1H, J = 9.6, 2.3Hz), 7.24 (s, 1H), 7.66 (d, 1H, J = 5.5 Hz), 8.53 (br s, 1H), 8.54 (s, 1H), 8.76 (d, 1H, J = 5.5 Hz). | 531 | 529 |
| 15 | ¹H-NMR (DMSO-D$_6$) δ: 1.10 (d, 3H, J = 7.2 Hz), 1.38 (s, 6H), 2.50-2.59 (m, 1H), 3.08 (q, 1H, J = 8.8 Hz), 3.24 (t, 1H, J = 8.8 Hz), 3.47 (t, 1H, J = 8.5 Hz), 6.96 (br s, 1H), 7.06 (dt, 1H, J = 10.2, 2.2 Hz), 7.13 (s, 1H), 7.27 (dt, 1H, J = 9.2, 1.8 Hz), 7.69 (br s, 1H), 8.80 (s, 1H), 9.18 (d, 1H, J = 1.2 Hz), 11.27 (br s, 1H). | 575 | 573 |
| 16 | ¹H-NMR (DMSO-D$_6$) δ: 1.09 (d, 3H, J = 7.2 Hz), 1.40 (s, 6H), 2.49-2.58 (m, 1H), 3.04 (q, 1H, J = 8.9 Hz), 3.24 (t, 1H, J = 9.1 Hz), 3.46 (t, 1H, J = 8.8 Hz), 6.96 (br s, 1H), 7.04 (dt, 1H, J = 10.1, 2.2 Hz), 7.07 (s, 1H), 7.19 (dt, 1H, J = 9.3, 1.8 Hz), 7.68 (br s, 1H), 7.90 (d, 1H, J = 5.1 Hz), 9.04 (d, 1H, J = 5.1 Hz), 11.39 (br s, 1H). | 575 | 573 |
| 17 | ¹H-NMR (DMSO-D$_6$) δ: 1.09 (d, 3H, J = 7.2 Hz), 1.30 (s, 6H), 2.50-2.59 (m, 1H), 3.00-3.09 (m, 1H), 3.20-3.26 (m, 1H), 3.42-3.48 (m, 1H), 6.74-6.76 (m, 1H), 7.05-7.10 (m, 1H), 7.08 (s, 1H), 7.18 (ddd, 1H, J = 9.0, 2.3, 1.4 Hz), 7.67 (br s, 1H), 7.91 (dd, 1H, J = 2.1, 2.1 Hz), 8.46 (dd, 1H, J = 2.1, 0.5 Hz), 8.63 (dd, 1H, J = 2.1, 0.5 Hz), 11.06 (br s, 1H). | 540 | 538 |
| 18 | ¹H-NMR (DMSO-D$_6$) δ: 1.10 (d, 3H, J = 7.4 Hz), 1.40 (d, 6H, J = 0.7 Hz), 2.49-2.58 (m, 1H), 3.08 (q, 1H, J = 8.9 Hz), 3.24 (t, 1H, J = 8.9 Hz), 3.47 (t, 1H, J = 8.6 Hz), 6.99 (t, 1H, J = 1.6 Hz), 7.07 | 575 | 573 |

| Example | ¹H-NMR | MS (M + H) | MS (M − H) |
|---|---|---|---|
| | (dt, 1H, J = 10.0, 2.3 Hz), 7.10 (s, 1H), 7.19 (ddd, 1H, J = 9.4, 2.4, 1.2 Hz), 7.69 (br s, 1H), 9.04 (s, 1H), 9.28 (s, 1H), 11.25 (br s, 1H). | | |
| 19 | ¹H-NMR (DMSO-D₆) δ: 1.09 (d, 3H, J = 6.9 Hz), 1.27 (s, 6H), 2.54-2.60 (m, 1H), 3.08 (ddd, 1H, J = 8.4, 8.4, 8.4 Hz), 3.24 (dd, 1H, J = 8.4, 8.4 Hz), 3.46 (dd, 1H, J = 8.4, 8.4 Hz), 6.51-6.53 (m, 1H), 7.05 (dt, 1H, J = 10.0, 2.3 Hz), 7.13-7.17 (m, 1H), 7.26 (s, 1H), 7.67 (br s, 1H), 8.97 (d, 1H, J = 2.1 Hz), 9.05 (d, 1H, J = 2.1 Hz), 11.03 (br s, 1H). | 575 | 573 |
| 20 | ¹H-NMR (DMSO-D₆) δ: 1.09 (d, 3H, J = 7.2 Hz), 1.27 (s, 6H), 2.48-2.59 (m, 1H), 3.06 (q, 1H, J = 8.9 Hz), 3.23 (t, 1H, J = 9.0 Hz), 3.45 (t, 1H, J = 8.5 Hz), 6.71 (br s, 1H), 7.10 (dt, 1H, J = 10.1, 2.3 Hz), 7.12 (s, 1H), 7.23-7.26 (m, 1H), 7.68 (br s, 1H), 7.93 (dd, 1H, J = 8.4, 2.1 Hz), 8.00 (d, 1H, J = 8.4 Hz), 8.69 (d, 1H, J = 2.4 Hz), 11.13 (s, 1H). | 574 | 572 |
| 21 | ¹H-NMR (DMSO-D₆) δ: 1.09 (d, 3H, J = 7.2 Hz), 1.30 (s, 6H), 2.50-2.60 (m, 1H), 3.00-3.10 (m, 1H), 3.19-3.26 (m, 1H), 3.41-3.49 (m, 1H), 6.73-6.75 (m, 1H), 7.05-7.10 (m, 1H), 7.09 (s, 1H), 7.16 (ddd, 1H, J = 9.2, 2.3, 1.6 Hz), 7.67 (br s, 1H), 7.78 (ddd, 1H, J = 9.5, 2.7, 2.1 Hz), 8.35-8.37 (m, 1H), 8.61 (dd, 1H, J = 2.7, 0.5 Hz), 11.07 (br s, 1H). | 524 | 522 |
| 22 | ¹H-NMR (DMSO-D₆) δ: 1.09 (d, 3H, J = 7.2 Hz), 1.31 (s, 6H), 2.50-2.60 (m, 1H), 3.01-3.10 (m, 1H), 3.20-3.27 (m, 1H), 3.42-3.49 (m, 1H), 6.80-6.83 (m, 1H), 7.08 (ddd, 1H, J = 9.9, 2.3, 2.2 Hz), 7.11 (s, 1H), 7.18 (ddd, 1H, J = 9.1, 2.3, 1.5 Hz), 7.68 (br s, 1H), 8.76 (s, 2H), 9.16 (s, 1H), 11.11 (br s, 1H). | 507 | 505 |
| 23 | ¹H-NMR (DMSO-D₆) δ: 1.08 (d, 3H, J = 7.2 Hz), 1.33 (s, 6H), 2.51-2.57 (m, 1H), 3.05 (ddd, 1H, J = 8.6, 8.6, 8.6 Hz), 3.22 (dd, 1H, J = 8.6, 8.6 Hz), 3.45 (dd, 1H, J = 8.6, 8.6 Hz), 6.80-6.82 (m, 1H), 7.01 (dt, 1H, J = 10.1, 2.3 Hz), 7.07 (s, 1H), 7.14-7.18 (m, 1H), 7.66 (br s, 1H), 8.31-8.33 (m, 1H), 8.58 (d, 1H, J = 2.3 Hz), 8.99 (d, 1H, J = 2.3 Hz), 11.13 (br s, 1H). | 507 | 505 |
| 24 | ¹H-NMR (DMSO-D₆) δ: 1.09 (d, 3H, J = 7.4 Hz), 1.33 (s, 6H), 2.49-2.58 (m, 1H), 3.06 (q, 1H, J = 8.8 Hz), 3.24 (t, 1H, J = 8.9 Hz), 3.46 (t, 1H, J = 8.4 Hz), 6.73 (t, 1H, J = 1.6 Hz), 7.04 (dt, 1H, J = 10.1, 2.3 Hz), 7.07 (s, 1H), 7.21 (ddd, 1H, J = 9.0, 2.4, 1.2 Hz), 7.68 (br s, 1H), 7.91 (d, 1H, J = 8.8 Hz), 8.42 (dd, 1H, J = 8.9, 2.2 Hz), 8.63 (dd, 1H, J = 1.6, 0.9 Hz), 11.14 (br s, 1H). | 574 | 572 |
| 25 | ¹H-NMR (DMSO-D₆) δ: 1.08 (d, 3H, J = 7.4 Hz), 2.51-2.57 (m, 1H), 3.06 (ddd, 1H, J = 8.6, 8.6, 8.6 Hz), 3.23 (dd, 1H, J = 8.6, 8.6 Hz), 3.45 (dd, 1H, J = 8.6, 8.6 Hz), 4.80 (q, 2H, J = 8.9 Hz), 7.00-7.03 (m, 2H), 7.11-7.16 (m, 2H), 7.67 (br s, 1H), 8.89 (s, 2H), 11.19 (br s, 1H). | 547 | 545 |
| 26 | ¹H-NMR (CDCl₃) δ: 1.34 (d, 3H, J = 6.9 Hz), 2.87-2.95 (m, 1H), 3.05 (ddd, 1H, J = 8.6, 8.6, 8.6 Hz), 3.60-3.65 (m, 2H), 6.41 (br s, 1H), 7.13-7.16 (m, 1H), 7.20-7.25 (m, 2H), 7.30-7.34 (m, 1H), 7.49 (t, 1H, J = 8.0 Hz), 8.77 (s, 2H), 8.98 (br s, 1H). | 515 | 513 |

-continued

| Example | ¹H-NMR | MS (M + H) | MS (M − H) |
|---|---|---|---|
| 27 | ¹H-NMR (CDCl₃) δ: 1.36 (d, 3H, J = 6.9 Hz), 2.86-2.94 (m, 1H), 3.02 (ddd, 1H, J = 8.6, 8.6, 8.6 Hz), 3.60-3.68 (m, 2H), 6.14 (br s, 1H), 6.93-6.96 (m, 1H), 6.98-7.01 (m, 1H), 7.07-7.10 (m, 1H), 7.26 (s, 1H), 8.64 (s, 1H), 8.80 (s, 2H). | 533 | 531 |
| 28 | ¹H-NMR (DMSO-D₆) δ: 1.09 (d, 3H, J = 7.2 Hz), 2.49-2.59 (m, 1H), 3.06 (q, 1H, J = 9.4 Hz), 3.24 (t, 1H, J = 9.0 Hz), 3.46 (t, 1H, J = 8.7 Hz), 7.09 (br s, 1H), 7.18 (s, 1H), 7.46-7.53 (m, 2H), 7.69 (br s, 1H), 7.90 (dd, 1H, J = 8.4, 2.4 Hz), 7.98 (d, 1H, J = 8.4 Hz), 8.71 (d, 1H, J = 2.4 Hz), 11.16 (br s, 1H). | 532 | 530 |
| 29 | ¹H-NMR (DMSO-D₆) δ: 1.09 (d, 3H, J = 7.2 Hz), 2.49-2.58 (m, 1H), 3.06 (q, 1H, J = 8.8 Hz), 3.23 (t, 1H, J = 9.0 Hz), 3.46 (t, 1H, J = 8.7 Hz), 7.16 (br s, 1H), 7.18 (s, 1H), 7.43-7.52 (m, 2H), 7.68 (br s, 1H), 8.76 (s, 2H), 9.18 (s, 1H), 11.14 (br s, 1H). | 465 | 463 |
| 30 | ¹H-NMR (CDCl₃) δ: 1.35 (d, 3H, J = 7.2 Hz), 2.84-2.92 (m, 1H), 2.99 (ddd, 1H, J = 8.6, 8.6, 8.6 Hz), 3.56-3.67 (m, 2H), 6.17 (br s, 1H), 6.88-6.90 (m, 1H), 6.96-7.03 (m, 2H), 7.19 (s, 1H), 7.64 (t, 1H, J = 2.2 Hz), 8.40 (d, 1H, J = 2.2 Hz), 8.54 (d, 1H, J = 2.2 Hz), 8.76 (br s, 1H). | 498 | 496 |
| 31 | ¹H-NMR (DMSO-D₆) δ: 1.08 (d, 3H, J = 7.2 Hz), 2.51-2.57 (m, 1H), 3.04 (ddd, 1H, J = 8.6, 8.6, 8.6 Hz), 3.22 (dd, 1H, J = 8.6, 8.6 Hz), 3.44 (dd, 1H, J = 8.6, 8.6 Hz), 4.79 (q, 2H, J = 8.8 Hz), 6.85-6.88 (m, 1H), 6.96-6.98 (m, 1H), 7.08-7.12 (m, 2H), 7.66 (br s, 1H), 8.04-8.06 (m, 1H), 8.70-8.71 (m, 1H), 8.93-8.94 (m, 1H), 11.09 (br s, 1H). | 546 | 544 |
| 32 | ¹H-NMR (DMSO-D₆) δ: 1.09 (d, 3H, J = 7.2 Hz), 2.49-2.58 (m, 1H), 3.05 (q, 1H, J = 8.9 Hz), 3.23 (t, 1H, J = 8.8 Hz), 3.45 (t, 1H, J = 8.5 Hz), 4.82 (q, 2H, J = 8.9 Hz), 6.88 (dt, 1H, J = 9.1, 1.7 Hz), 6.98 (br s, 1H), 7.08-7.13 (m, 2H), 7.68 (br s, 1H), 8.73 (s, 2H), 9.16 (s, 1H), 11.11 (br s, 1H). | 479 | 477 |
| 33 | ¹H-NMR (DMSO-D₆) δ: 1.09 (d, 3H, J = 7.2 Hz), 2.50-2.58 (m, 1H), 3.06 (q, 1H, J = 8.9 Hz), 3.23 (t, 1H, J = 8.8 Hz), 3.46 (t, 1H, J = 8.5 Hz), 4.80 (q, 2H, J = 8.9 Hz), 6.88-6.92 (m, 1H), 6.96 (s, 1H), 7.09-7.14 (m, 2H), 7.68 (br s, 1H), 7.86 (dd, 1H, J = 8.7, 2.4 Hz), 7.98 (d, 1H, J = 8.7 Hz), 8.70 (d, 1H, J = 2.4 Hz), 11.13 (br s, 1H). | 546 | 544 |
| 34 | ¹H-NMR (DMSO-D₆) δ: 1.09 (d, 3H, J = 7.2 Hz), 2.50-2.60 (m, 1H), 3.00-3.09 (m, 1H), 3.19-3.27 (m, 1H), 3.41-3.49 (m, 1H), 4.82 (q, 2H, J = 8.9 Hz), 6.81 (ddd, 1H, J = 9.1, 2.3, 1.2 Hz), 6.93-6.96 (m, 1H), 7.07-7.12 (m, 1H), 7.10 (s, 1H), 7.68 (br s, 1H), 7.73 (ddd, 1H, J = 9.6, 2.5, 2.3 Hz), 8.31-8.34 (m, 1H), 8.61 (dd, 1H, J = 2.5, 0.5 Hz), 11.07 (br s, 1H). | 496 | 494 |
| 35 | ¹H-NMR (CDCl₃) δ: 1.34 (d, 3H, J = 6.9 Hz), 2.85-2.93 (m, 1H), 3.03 (ddd, 1H, J = 8.6, 8.6, 8.6 Hz), 3.56-3.65 (m, 2H), 4.31 (q, 2H, J = 7.9 Hz), 6.51 (br s, 1H), 6.61-6.65 (m, 1H), 6.70-6.74 (m, 2H), 7.15 (s, 1H), 7.65 (t, 1H, J = 2.2 Hz), 8.42 (d, 1H, J = 2.2 Hz), 8.52 (d, 1H, J = 2.2 Hz), 9.17 (br s, 1H). | 512 | 510 |
| 36 | ¹H-NMR (DMSO-D₆) δ: 1.08 (d, 3H, J = 7.2 Hz), 1.31 (s, 6H), 2.50-2.58 (m, 1H), | 537 | 535 |

-continued

| Example | ¹H-NMR | MS (M + H) | MS (M − H) |
|---|---|---|---|
| | 3.04 (q, 1H, J = 8.9 Hz), 3.22 (t, 1H, J = 9.0 Hz), 3.44 (t, 1H, J = 8.5 Hz), 3.94 (s, 3H), 6.76 (br s, 1H), 7.04-7.09 (m, 2H), 7.17 (dt, 1H, J = 8.9, 1.9 Hz), 7.68 (br s, 1H), 8.59 (s, 2H), 11.05 (br s, 1H). | | |
| 37 | ¹H-NMR (DMSO-D₆) δ: 1.08 (d, 3H, J = 7.2 Hz), 1.30 (s, 6H), 2.51-2.58 (m, 1H), 3.02 (ddd, 1H, J = 8.6, 8.6, 8.6 Hz), 3.13 (s, 6H), 3.22 (dd, 1H, J = 8.6, 8.6 Hz), 3.44 (dd, 1H, J = 8.6, 8.6 Hz), 6.72-6.73 (m, 1H), 7.01-7.04 (m, 2H), 7.14-7.17 (m, 1H), 7.67 (br s, 1H), 8.31 (s, 2H), 10.98 (br s, 1H). | 550 | 548 |
| 38 | ¹H-NMR (DMSO-D₆) δ: 1.08 (d, 3H, J = 7.2 Hz), 1.30 (s, 6H), 2.49-2.57 (m, 1H), 2.64 (s, 3H), 3.04 (q, 1H, J = 8.9 Hz), 3.23 (t, 1H, J = 9.0 Hz), 3.45 (t, 1H, J = 8.7 Hz), 6.77 (br s, 1H), 7.05-7.10 (m, 2H), 7.18 (dt, 1H, J = 8.8, 1.8 Hz), 7.68 (br s, 1H), 8.63 (s, 2H), 11.09 (br s, 1H). | 521 | 519 |

Compounds A to E as shown in the following table were obtained according to the description of WO 2013/031922.

Compound A
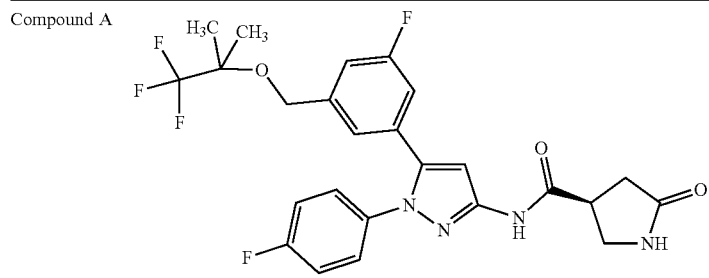

Compound B
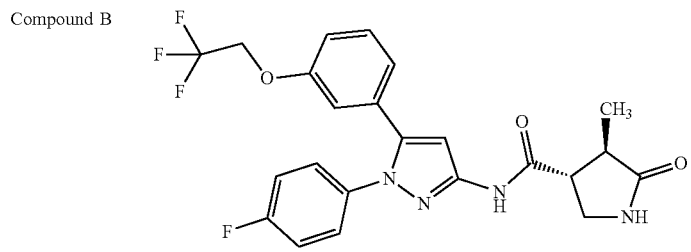

Compound C
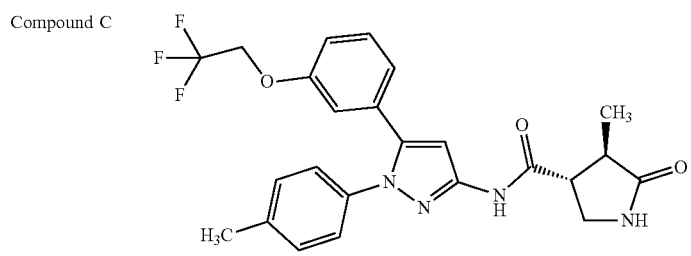

| | |
|---|---|
| Compound D | 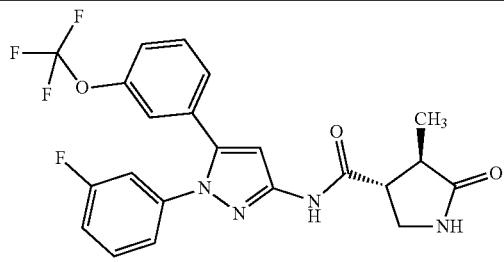 |
| Compound E | 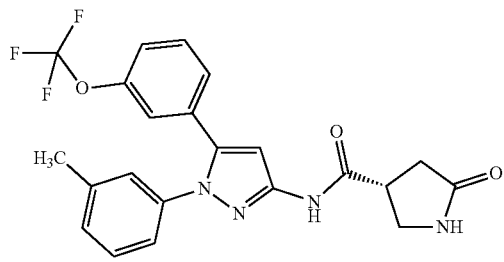 [SMILES: Cc1cccc(-n2nc(NC(=O)[C@H]3CNC(=O)C3)cc2-c2cccc(OC(F)(F)F)c2)c1] |
Metabolites 1 to 3 (i.e., metabolites of the compounds of Examples 1 to 3) and Metabolites A to E (i.e., metabolites of Compounds A to E), each of which is shown in the following table, were obtained according to the above Examples 1 to 3 and the description of WO 2013/031922.
| | |
|---|---|
| Metabolite 1 | 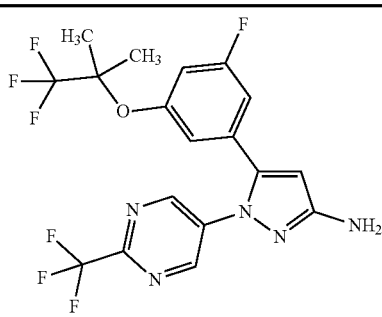 |
| Metabolite 2 | 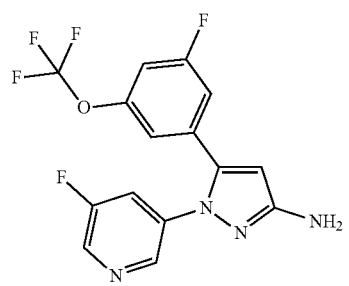 [SMILES: Nc1cc(-c2cc(F)cc(OC(F)(F)F)c2)n(-c2cncc(F)c2)n1] |
| Metabolite 3 | 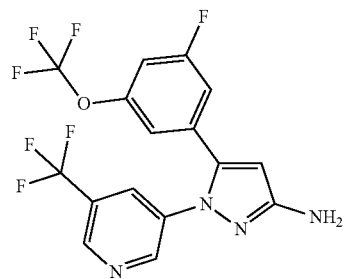 [SMILES: Nc1cc(-c2cc(F)cc(OC(F)(F)F)c2)n(-c2cncc(C(F)(F)F)c2)n1] |
| Metabolite A | 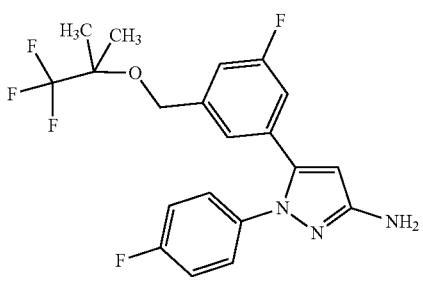 [SMILES: CC(C)(OCc1cc(F)cc(-c2cc(N)nn2-c2ccc(F)cc2)c1)C(F)(F)F] |
| Metabolite B | 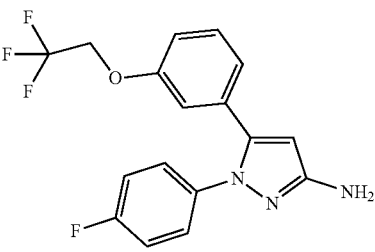 [SMILES: Nc1cc(-c2cccc(OCC(F)(F)F)c2)n(-c2ccc(F)cc2)n1] |
| Metabolite C | 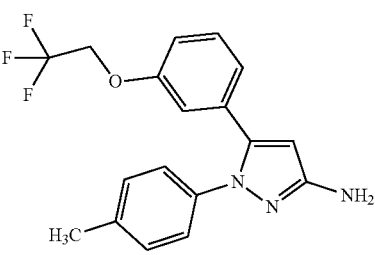 [SMILES: Cc1ccc(-n2nc(N)cc2-c2cccc(OCC(F)(F)F)c2)cc1] |

Metabolite D

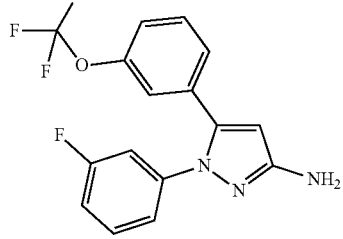

Metabolite E

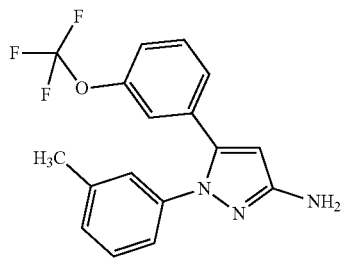 [SMILES: Cc1cccc(-n2nc(N)cc2-c2cccc(OC(F)(F)F)c2)c1]

Test Example 1

SGLT1 inhibitory activities of test compounds ($IC_{50}$ values) were calculated based on the amount of intracellular uptake of labelled α-methyl-D-glucopyranoside ($^{14}$C-AMG) transported by SGLT1.

1) Formation of Human SGLT1-Expressing Plasmid

A DNA fragment containing human SGLT1 was amplified by PCR (Polymerase Chain Reaction) using pCMV6-hSGLT1 (OriGene) as a template. In the human SGLT1, NheI recognition and cleavage sequence was added to the upstream of Kozac consensus sequence derived from a vector, and a stop codon, TAG, and SalI recognition and cleavage sequence were added to the immediate downstream of the protein-translating region of human SGLT1. The purified DNA fragment was cleaved by restriction enzymes NheI and SalI, followed by ligation with pcDNA3.1 (+) which was cleaved by NheI and XhoI, thereby forming human SGLT1-expressing plasmid, pcDNA-hSGLT1. The nucleic acid sequence of human SGLT1 inserted into a vector was completely identical to the protein-translated region of human SGLT1 sequence (Accession number NM_000343) registered in GenBank, and the sequence of the portion connected to the vector was as expected.

2) Establishment of Human SGLT1-Stably-Expressing Cell Lines

Human SGLT-expressing plasmid, pcDNA-hSGLT1, was transfected into each CHO-K1 cell by Lipofectamine 2000 (Invitrogen) and cultured in the presence of G418 (Nacalai Tesque) to select drug-resistant cell lines. A cell line having the highest ratio (S/B ratio) of the amount of intracellular uptake of $^{14}$C-AMG per cell to the amount of intracellular uptake of $^{14}$C-AMG after treatment with a SGLT inhibitor, phlorizin, was selected as a human SGLT1-stably-expressing cell line from the drug-resistant cell lines.

3) Assessment of SGLT1 Inhibitory Activity

Human SGLT1-stably-expressing cell lines were seeded at 5×10$^4$ cells/well on BioCoat™ Poly-D-Lysine 96 well plate with Lid (Becton, Dickinson and Company) and cultured at 37° C. under 5% $CO_2$ overnight. The medium was replaced with 100 µL/well of Na(−) buffer (140 mM choline chloride, 2 mM KCl, 1 mM $MgCl_2$, 1 mM $CaCl_2$, 10 mM HEPES, 5 mM Tris, pH 7.4), and then the mixture was let stand at 37° C. under 5% $CO_2$ for 20 minutes. After removal of Na(−) buffer, thereto was added 40 µL/well of a test compound solution prepared with Na(+) buffer (140 mM NaCl, 2 mM KCl, 1 mM $MgCl_2$, 1 mM $CaCl_2$, 10 mM HEPES, 5 mM Tris, pH 7.4) comprising BSA. Then, thereto was added 40 µL/well of Na(+) buffer comprising 8 kBq of $^{14}$C-AMG and 2 mM AMG, and the mixture was mixed well. For a blank, 40 µL/well of Na(−) buffer comprising BSA was added, and in addition, 40 µL/well of Na(−) buffer comprising 8 kBq of $^{14}$C-AMG and 2 mM AMG was added, and the mixture was mixed well. After incubation by being let stand for 1 hour at 37° C. under 5% $CO_2$, cells were washed twice with 100 µL/well of ice-cooled wash buffer (100 mM AMG, 140 mM choline chloride, 2 mM KCl, 1 mM $MgCl_2$, 1 mM $CaCl_2$, 10 mM HEPES, 5 mM Tris, pH 7.4) to terminate the reaction. A cell lysate was prepared by addition of 50 µL/well of 0.2N aqueous NaOH solution. In the assessment for the uptake ability of $^{14}$C-AMG, the total amount of the cell lysate was transferred to OptiPlate 96 (Perkin-Elmer) with 100 µL/well of MicroScint-40 (Perkin-Elmer) dispensed and $^{14}$C of CPM was measured with TOPCOUNT NXT (Perkin-Elmer).

Data was calculated by deducting the average value of CPM for blank well from the average value of CPM for each well treated. An inhibition rate for each test compound in each concentration was calculated from the following equation:

$[(A-B)/A] \times 100$ wherein A is data for a solvent control and B is data for treatment with each test compound.

Each $IC_{50}$ value (50% inhibitory concentration) for each test compound was calculated based on two concentrations before and after a 50% inhibition rate and the inhibition rate. Results of the example compounds are shown in the following table.

| Example | hSGLT1 $IC_{50}$ (µM) |
| --- | --- |
| 1 | 0.0019 |
| 2 | 0.014 |
| 3 | 0.0086 |
| 4 | 0.023 |
| 5 | 0.022 |
| 6 | 0.009 |
| 7 | 0.017 |
| 8 | 45% inhibition in 0.3 µM |
| 9 | 0.073 |
| 10 | 0.0012 |
| 11 | 0.0084 |
| 12 | 0.0043 |
| 13 | 0.0029 |
| 14 | 0.0037 |
| 15 | 0.0061 |
| 16 | 0.083 |
| 17 | 0.0013 |
| 18 | 0.029 |
| 19 | 0.029 |
| 20 | 0.0012 |
| 21 | 0.0012 |
| 22 | 0.0034 |
| 23 | 0.011 |
| 24 | 0.0053 |
| 25 | 0.0057 |
| 26 | 0.047 |
| 27 | 0.03 |
| 28 | 0.0072 |
| 29 | 0.052 |
| 30 | 0.0027 |
| 31 | 0.0057 |

-continued

| Example | hSGLT1 IC$_{50}$ (µM) |
|---|---|
| 32 | 0.069 |
| 33 | 0.0059 |
| 34 | 0.0098 |
| 35 | 0.0046 |
| 36 | 0.0019 |
| 37 | 0.00098 |
| 38 | 0.004 |

Test Example 2

Ames Test (Reverse Mutation Test)

Metabolites 1 to 3 and Metabolites A to E were each tested herein. The purpose of this test is to evaluate the potential of each metabolite to induce reverse mutations in the standard strains of *Salmonella typhimurium* (TA98, TA1537, TA100, and TA1535) and *Escherichia coli* (WP2uvrA), in either the presence or absence of a rat liver metabolic activation system (S9 mix).

The solvent used herein was dimethyl sulfoxide (DMSO, 100 µL/plate).

The test was performed by the pre-incubation method with or without S9 mix. When the test was performed without S9 mix, sodium phosphate buffer solution (pH 7.4) was added.

0.5 mL of S9 mix or 0.5 mL of 0.1 mol/L sodium phosphate buffer solution (pH 7.4), and 0.1 mL of the bacterial culture solution were added to a test tube containing 0.1 mL of the negative control formulation (DMSO alone), the metabolite, or the positive control formulation. The mixtures were pre-incubated at 37° C. for 20 minutes while shaking. After the pre-incubation period, 2 mL of top agar were added and the mixtures were vortex-mixed and seeded onto plates. Two plates per treatment were used. Each plate was incubated at 37±1° C. for 48 hours or more and the revertant colonies were counted. The mean number of revertant colonies for each treatment plate was then calculated. The presence or absence of growth inhibition due to any antibacterial effect of the test article and precipitation of the test article was observed grossly or under a stereomicroscope. The results were judged as positive if the mean number of revertant colonies showed a dose dependent increase which reached 2-fold over that of the negative control at one or more doses. Evaluation was based on mean values with no statistical comparisons being used.

The results of the test are shown in the following tables (Tables 1-1 to 3-2 and Tables A-1 to E-2). In conclusion, Metabolites 1 to 3 did not have potential to induce reverse mutations in any of the bacterial tester strains, whereas Metabolites A to E had potential to induce reverse mutations in at least one of the bacterial tester strains in the presence and/or absence of S9 mix.

Metabolite A had potential to induce reverse mutations in the bacterial tester strains of TA98 and TA1537 in the presence of S9 mix.

Metabolite B had potential to induce reverse mutations in the bacterial tester strains of TA98, TA1537, TA100, and TA1535 in the presence of S9 mix and TA1537 in the absence of S9 mix.

Metabolite C had potential to induce reverse mutations in the bacterial tester strains of TA98, TA1537, and TA100 in the presence of S9 mix and WP2uvrA in the absence of S9 mix.

Metabolite D had potential to induce reverse mutations in the bacterial tester strains of TA100 in the presence of S9 mix and TA1535 in the absence of S9 mix.

Metabolite E had potential to induce reverse mutations in the bacterial tester strains of TA98, TA1537, and TA100 in the presence of S9 mix.

TABLE 1-1

| Test article | Dose (µg/plate) | S9 Mix | Number of revertant colonies ||||||||||
|---|---|---|---|---|---|---|---|---|---|---|---|---|
| | | | TA98 | | TA1537 | | TA100 | | TA1535 | | WP2uvrA | |
| DMSO | (0.1 mL) | + | 38 | | 14 | | 118 | | 9 | | 18 | |
| Metabolite 1 | 6.9 | + | 37 | | 13 | | 132 | | 10 | | 18 | |
| | 21 | + | 39 | | 12 | | 132 | | 8 | | 20 | |
| | 62 | + | 40 | | 13 | | 113 | | 9 | | 18 | |
| | 185 | + | 40 | | 13 | | 108 | † | 10 | | 16 | |
| | 556 | + | 34 | * | 10 | * | 128 | † | 9 | | 18 | |
| | 1667 | + | 27 | *† | 9 | *† | 131 | *† | 10 | *† | 14 | *† |
| | 5000 | + | 21 | *† | 4 | *† | 121 | *† | 7 | *† | 11 | *† |
| 2AA | 0.5 | + | 289 | | — | | — | | — | | — | |
| | 1 | + | — | | — | | 858 | | — | | — | |
| | 2 | + | — | | 135 | | — | | 146 | | — | |
| | 10 | + | — | | — | | — | | — | | 169 | |

—: Not tested

*: Growth inhibition

†: Precipitation

DMSO: Dimethyl sulfoxide

2AA: 2-Aminoanthracene

The number of revertant colonies shows the mean number of each plate.

TABLE 1-2

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| DMSO | (0.1 mL) | — | 33 | 10 | 89 | 13 | 20 |
| Metabolite 1 | 6.9 | — | 32 | 8 | 89 | 11 | 17 |
| | 21 | — | 32 | 8 | 87 | 10 | 19 |
| | 62 | — | 31 | 8 | 87 | 9 | 16 |
| | 185 | — | 29 | 9 | 89 | 7 | 17 |
| | 556 | — | 30 | 9 | 80 | 9 | 18 |
| | 1667 | — | 15 *† | 5 *† | 69 *† | 5 *† | 15 *† |
| | 5000 | — | 7 *† | 3 *† | 47 *† | 7 *† | 9 *† |
| AF-2 | 0.01 | — | — | — | 404 | — | 154 |
| | 0.1 | — | 510 | — | — | — | — |
| 9AA | 80 | — | — | 372 | — | — | — |
| SA | 0.5 | — | — | — | — | 269 | — |

—: Not tested
*: Growth inhibition
†: Precipitation
DMSO: Dimethyl sulfoxide
AF-2: 2-(2-Furyl)-3-(5-nitro-2-furyl)acrylamide
9AA: 9-Aminoacridine hydrochloride monohydrate
SA: Sodium azide The number of revertant colonies shows the mean number of each plate.

TABLE 2-1

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| DMSO | (0.1 mL) | + | 38 | 14 | 100 | 9 | 18 |
| Metabolite 2 | 6.9 | + | 35 | 12 | 109 | 8 | 19 |
| | 21 | + | 37 | 13 | 119 | 9 | 19 |
| | 62 | + | 35 | 12 | 118 | 11 | 19 |
| | 185 | + | 36 | 12 | 125 | 9 | 19 |
| | 556 | + | 22 * | 8 * | 115 *† | 4 * | 17 * |
| | 1667 | + | 20 *† | 0 *† | 97 *† | 3 *† | 14 *† |
| | 5000 | + | 16 *† | 1 *† | 92 *† | 1 *† | 9 *† |
| 2AA | 0.5 | + | 289 | — | — | — | — |
| | 1 | + | — | — | 687 | — | — |
| | 2 | + | — | 135 | — | 146 | — |
| | 10 | + | — | — | — | — | 169 |

—: Not tested
*: Growth inhibition
†: Precipitation
DMSO: Dimethyl sulfoxide
2AA: 2-Aminoanthracene The number of revertant colonies shows the mean number of each plate.

TABLE 2-2

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| DMSO | (0.1 mL) | – | 33 | 10 | 89 | 13 | 20 |
| Metabolite 2 | 6.9 | – | 30 | 9 | 89 | 9 | 21 |
| | 21 | – | 30 | 8 | 90 | 11 | 16 |
| | 62 | – | 28 | 8 | 87 | 10 | 23 |
| | 185 | – | 28 | 8 | 86 | 8 | 20 |
| | 556 | – | 12 * | 3 * | 6 * | 8 * | 16 * |
| | 1667 | – | 9 *† | 3 *† | 5 *† | 0 *† | 13 *† |
| | 5000 | – | 7 *† | 2 *† | 5 *† | 0 *† | 8 *† |
| AF-2 | 0.01 | – | — | — | 404 | — | 154 |
| | 0.1 | – | 510 | — | — | — | — |

TABLE 2-2-continued

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| 9AA | 80 | − | — | 372 | — | — | — |
| SA | 0.5 | − | — | — | — | 269 | — |

—: Not tested
*: Growth inhibition
†: Precipitation
DMSO: Dimethyl sulfoxide
AF-2: 2-(2-Furyl)-3-(5-nitro-2-furyl)acrylamide
9AA: 9-Aminoacridine hydrochloride monohydrate
SA: Sodium azide
The number of revertant colonies shows the mean number of each plate.

TABLE 3-1

| Test article | Dose (μg/plate) | S9 Mix | Number of revertant colonies | | | | | | | | |
|---|---|---|---|---|---|---|---|---|---|---|---|
| | | | TA98 | | TA1537 | | TA100 | | TA1535 | | WP2uvrA |
| DMSO | (0.1 mL) | + | 38 | | 14 | | 106 | | 9 | | 18 |
| Metabolite 3 | 6.9 | + | 36 | | 13 | | 134 | | 10 | | 22 |
| | 21 | + | 38 | | 11 | | 123 | | 11 | | 22 |
| | 62 | + | 38 | | 12 | | 108 | | 10 | | 21 |
| | 185 | + | 33 | | 12 | | 103 | | 9 | | 21 |
| | 556 | + | 27 | | 8 | * | 99 | | 7 | * | 18 | * |
| | 1667 | + | 25 | *† | 3 | *† | 67 | *† | 4 | *† | 21 | *† |
| | 5000 | + | 17 | *† | 1 | *† | 43 | #† | 2 | *† | 19 | *† |
| 2AA | 0.5 | + | 289 | | — | | — | | — | | — |
| | 1 | + | — | | — | | 702 | | — | | — |
| | 2 | + | — | | 135 | | — | | 146 | | — |
| | 10 | + | — | | — | | — | | — | | 169 |

—: Not tested
*: Growth inhibition
†: Precipitation
: The condition of background bacterial flora was not able to be observed due to precipitation.
DMSO: Dimethyl sulfoxide
2AA: 2-Aminoanthracene
The number of revertant colonies shows the mean number of each plate.

TABLE 3-2

| Test article | Dose (μg/plate) | S9 Mix | Number of revertant colonies | | | | | | | | |
|---|---|---|---|---|---|---|---|---|---|---|---|
| | | | TA98 | | TA1537 | | TA100 | | TA1535 | | WP2uvrA |
| DMSO | (0.1 mL) | − | 33 | | 10 | | 89 | | 13 | | 20 |
| Metabolite 3 | 6.9 | − | 29 | | 8 | | 88 | | 9 | | 23 |
| | 21 | − | 28 | | 7 | | 91 | | 11 | | 15 |
| | 62 | − | 29 | | 8 | | 93 | | 4 | | 23 |
| | 185 | − | 26 | | 7 | | 92 | | 7 | | 20 |
| | 556 | − | 24 | | 2 | * | 59 | * | 6 | * | 22 |
| | 1667 | − | 18 | * | 3 | * | 29 | * | 3 | * | 19 | * |
| | 5000 | − | 14 | *† | 2 | *† | 12 | *† | 4 | *† | 14 | *† |
| AF-2 | 0.01 | − | — | | — | | 404 | | — | | 154 |
| | 0.1 | − | 510 | | — | | — | | — | | — |
| 9AA | 80 | − | — | | 372 | | — | | — | | — |
| SA | 0.5 | − | — | | — | | — | | 269 | | — |

—: Not tested
*: Growth inhibition
†: Precipitation
DMSO: Dimethyl sulfoxide
AF-2: 2-(2-Furyl)-3-(5-nitro-2-furyl)acrylamide
9AA: 9-Aminoacridine hydrochloride monohydrate
SA: Sodium azide
The number of revertant colonies shows the mean number of each plate.

TABLE A-1

| Test article | Dose (μg/plate) | | S9 Mix | Number of revertant colonies | | | | |
|---|---|---|---|---|---|---|---|---|
| | | | | TA98 | TA1537 | TA100 | TA1535 | WP2uvrA |
| DMSO | (0.1 mL) | | + | 36 | 10 | 140 | 10 | 30 |
| Metabolite A | 2.3 | | + | 39 | 14 | 139 | 10 | 31 |
| | 6.9 | | + | 42 | 20 | 203 | 15 | 18 |
| | 21 | | + | 52 | 13 | 237 | 14 | 24 |
| | 62 | | + | 47 | 18 | 185 | 11 | 18 |
| | 185 | | + | 49 | 15 | * 151 | 9 | 23 |
| | 556 | | + | 51 | 15 | * 119 | 7 | 32 |
| | 1667 | † | + | 57 | 19 | * 100 | 7 | 28 |
| | 5000 | † | + | 88 | 24 | * 98 | 3 | 28 |
| B[a]P | 5.0 | | + | 396 | 112 | 1053 | — | — |
| 2AA | 2.0 | | + | — | — | — | 332 | — |
| | 10.0 | | + | — | — | — | — | 702 |

—: Not tested
*: Growth inhibition
†: Precipitation
DMSO: Dimethyl sulfoxide
B[a]P: Benzo[a]pyrene
2AA: 2-Aminoanthracene
The number of revertant colonies shows the mean number of each plate.

TABLE A-2

| Test article | Dose (μg/plate) | | S9 Mix | Number of revertant colonies | | | | |
|---|---|---|---|---|---|---|---|---|
| | | | | TA98 | TA1537 | TA100 | TA1535 | WP2uvrA |
| DMSO | (0.1 mL) | | − | 26 | 8 | 106 | 11 | 25 |
| Metabolite A | 2.3 | | − | 27 | 11 | 99 | 20 | 25 |
| | 6.9 | | − | 22 | 13 | 98 | 21 | 27 |
| | 21 | | − | 23 | 11 | 71 | 11 | 22 |
| | 62 | | − | 25 | 7 | 96 | 6 | 21 |
| | 185 | | − | 32 | 6 | 85 | 9 * | 22 |
| | 556 | | − | 21 * | 7 * | 86 * | 5 * | 16 |
| | 1667 | † | − | 23 * | 6 * | 69 * | 6 * | 18 |
| | 5000 | † | − | 21 * | 8 * | 82 * | 7 * | 20 |
| AF-2 | 0.01 | | − | — | — | 517 | — | 89 |
| | 0.1 | | − | 337 | — | — | — | — |
| ICR-191 | 1.0 | | − | — | 1448 | — | — | — |
| SAZ | 0.5 | | − | — | — | — | 368 | — |

—: Not tested
*: Growth inhibition
†: Precipitation
DMSO: Dimethyl sulfoxide
AF-2: 2-(2-Furyl)-3-(5-nitro-2-furyl)acrylamide
ICR-191: 2-Methoxy-6-chloro-9-[3-(2-chloroethyl)aminopropylamino]acridinedihydrochloride
SAZ: Sodium azide
The number of revertant colonies shows the mean number of each plate.

TABLE B-1

| Test article | Dose (μg/plate) | | S9 Mix | Number of revertant colonies | | | | |
|---|---|---|---|---|---|---|---|---|
| | | | | TA98 | TA1537 | TA100 | TA1535 | WP2uvrA |
| DMSO | (0.1 mL) | | + | 23 | 13 | 128 | 11 | 21 |
| Metabolite B | 2.3 | | + | 589 | 65 | 1338 | 18 | 26 |
| | 6.9 | | + | 1310 | 227 | 2032 | 32 | 32 |
| | 21 | | + | 1001 | 180 | 2016 | 20 | 24 |
| | 62 | | + | 490 | 102 | 2320 | 21 | 30 |
| | 185 | | + | 268 | 85 * | 1799 | 15 * | 18 |
| | 556 | | + | 77 * | 0 * | 1082 * | 7 * | 19 * |
| | 1667 | † | + | 15 * | 0 * | 182 * | 0 * | 13 * |
| | 5000 | † | + | 12 * | 0 * | 157 * | 0 * | 12 * |

TABLE B-1-continued

| Test article | Dose (μg/plate) | S9 Mix | TA98 | TA1537 | TA100 | TA1535 | WP2uvrA |
|---|---|---|---|---|---|---|---|
| B[a]P | 5.0 | + | 397 | 87 | 973 | — | — |
| 2AA | 2.0 | + | — | — | — | 308 | — |
|  | 10.0 | + | — | — | — | — | 608 |

—: Not tested
*: Growth inhibition
†: Precipitation
DMSO: Dimethyl sulfoxide
B[a]P: Benzo[a]pyrene
2AA: 2-Aminoanthracene
The number of revertant colonies shows the mean number of each plate.

TABLE B-2

| Test article | Dose (μg/plate) | S9 Mix | TA98 | TA1537 | TA100 | TA1535 | WP2uvrA |
|---|---|---|---|---|---|---|---|
| DMSO | (0.1 mL) | − | 23 | 5 | 119 | 13 | 22 |
| Metabolite B | 2.3 | − | 26 | 17 | 110 | 10 | 20 |
|  | 6.9 | − | 27 | 20 | 96 | 18 | 26 |
|  | 21 | − | 28 | 16 | 96 | 12 | 24 |
|  | 62 | − | 32 | 11 | 101 | 15 | 27 |
|  | 185 | − | 17 | 3 * | 75 * | 6 * | 22 |
|  | 556 | − | 12 * | 0 * | 38 * | 0 * | 10 * |
|  | 1667 † | − | 6 * | 0 * | 27 * | 0 * | 15 * |
|  | 5000 † | − | 2 * | 0 * | 0 * | 0 * | 7 * |
| AF-2 | 0.01 | − | — | — | 526 | — | 100 |
|  | 0.1 | − | 417 | — | — | — | — |
| ICR-191 | 1.0 | − | — | 1435 | — | — | — |
| SAZ | 0.5 | − | — | — | — | 335 | — |

—: Not tested
*: Growth inhibition
†: Precipitation
DMSO: Dimethyl sulfoxide
AF-2: 2-(2-Furyl)-3-(5-nitro-2-furyl)acrylamide
ICR-191: 2-Methoxy-6-chloro-9-[3-(2-chloroethyl)aminopropylamino]acridinedihydrochloride
SAZ: Sodium azide
The number of revertant colonies shows the mean number of each plate.

TABLE C-1

| Test article | Dose (μg/plate) | S9 Mix | TA98 | TA1537 | TA100 | TA1535 | WP2uvrA |
|---|---|---|---|---|---|---|---|
| DMSO | (0.1 mL) | + | 33 | 14 | 121 | 13 | 19 |
| Metabolite C | 2.3 | + | 93 | 41 | 553 | 22 | 25 |
|  | 6.9 | + | 218 | 92 | 1417 | 21 | 20 |
|  | 21 | + | 522 | 157 | 2888 | 20 | 30 |
|  | 62 | + | 484 | 227 | 3713 | 23 | 24 |
|  | 185 | + | 287 | 151 * | 2889 | 13 * | 20 |
|  | 556 | + | 151 * | 54 * | 1288 * | 7 * | 24 |
|  | 1667 † | + | 61 * | 39 * | 1576 * | 0 * | 16 |
|  | 5000 † | + | 0 * | 3 * | 1160 * | 0 * | 6 * |
| B[a]P | 5.0 | + | 366 | 95 | 1058 | — | — |
| 2AA | 2.0 | + | — | — | — | 331 | — |
|  | 10.0 | + | — | — | — | — | 611 |

—: Not tested
*: Growth inhibition
†: Precipitation
DMSO: Dimethyl sulfoxide
B[a]P: Benzo[a]pyrene
2AA: 2-Aminoanthracene
The number of revertant colonies shows the mean number of each plate.

TABLE C-2

| Test article | Dose (μg/plate) | | S9 Mix | Number of revertant colonies | | | | | | | | |
|---|---|---|---|---|---|---|---|---|---|---|---|---|
| | | | | TA98 | | TA1537 | | TA100 | | TA1535 | | WP2uvrA |
| DMSO | (0.1 mL) | | − | 26 | | 9 | | 100 | | 10 | | 22 |
| Metabolite C | 2.3 | | − | 25 | | 9 | | 107 | | 17 | | 24 |
| | 6.9 | | − | 32 | | 16 | | 104 | | 13 | | 23 |
| | 21 | | − | 21 | | 16 | | 115 | | 19 | | 26 |
| | 62 | | − | 21 | | 10 | | 109 | | 11 | | 19 |
| | 185 | | − | 20 | | 3 * | | 93 | | 3 * | | 13 |
| | 556 | † | − | 19 | | 0 * | | 62 * | | 0 * | | 74 |
| | 1667 | † | − | 6 * | | 0 * | | 58 * | | 0 * | | 8 * |
| | 5000 | † | − | 0 * | | 0 * | | 40 * | | 0 * | | 5 * |
| AF-2 | 0.01 | | − | — | | — | | 488 | | — | | 87 |
| | 0.1 | | − | 360 | | — | | — | | — | | — |
| ICR-191 | 1.0 | | − | — | | 1413 | | — | | — | | — |
| SAZ | 0.5 | | − | — | | — | | — | | 403 | | — |

—: Not tested
*: Growth inhibition
†: Precipitation
DMSO: Dimethyl sulfoxide
AF-2: 2-(2-Furyl)-3-(5-nitro-2-furyl)acrylamide
ICR-191: 2-Methoxy-6-chloro-9-[3-(2-chloroethyl)aminopropylamino]acridinedihydrochloride
SAZ: Sodium azide
The number of revertant colonies shows the mean number of each plate.

TABLE D-1

| Test article | Dose (μg/plate) | | S9 Mix | Number of revertant colonies | | | | | | | | |
|---|---|---|---|---|---|---|---|---|---|---|---|---|
| | | | | TA98 | | TA1537 | | TA100 | | TA1535 | | WP2uvrA |
| DMSO | (0.1 mL) | | + | 39 | | 11 | | 118 | | 11 | | 20 |
| Metabolite D | 2.3 | | + | 35 | | 13 | | 153 | | 12 | | 34 |
| | 6.9 | | + | 63 | | 13 | | 248 | | 14 | | 39 |
| | 21 | | + | 76 | | 16 | | 506 | | 11 | | 22 |
| | 62 | | + | 75 | | 15 * | | 630 | | 8 | | 24 * |
| | 185 | | + | 45 * | | 13 * | | 380 * | | 5 * | | 16 * |
| | 556 | † | + | 12 * | | 0 * | | 82 * | | 5 * | | 14 * |
| | 1667 | † | + | 11 * | | 0 * | | 94 * | | 4 * | | 9 * |
| | 5000 | † | + | 0 * | | 0 * | | 226 * | | 4 * | | 14 * |
| B[a]P | 5.0 | | + | 409 | | 110 | | 1038 | | — | | — |
| 2AA | 2.0 | | + | — | | — | | — | | 261 | | — |
| | 10.0 | | + | — | | — | | — | | — | | 570 |

—: Not tested
*: Growth inhibition
†: Precipitation
DMSO: Dimethyl sulfoxide
B[a]P: Benzo[a]pyrene
2AA: 2-Aminoanthracene
The number of revertant colonies shows the mean number of each plate.

TABLE D-2

| Test article | Dose (μg/plate) | | S9 Mix | Number of revertant colonies | | | | | | | | |
|---|---|---|---|---|---|---|---|---|---|---|---|---|
| | | | | TA98 | | TA1537 | | TA100 | | TA1535 | | WP2uvrA |
| DMSO | (0.1 mL) | | − | 28 | | 10 | | 89 | | 10 | | 19 |
| Metabolite D | 2.3 | | − | 31 | | 15 | | 91 | | 15 | | 26 |
| | 6.9 | | − | 30 | | 15 | | 101 | | 16 | | 23 |
| | 21 | | − | 31 | | 17 | | 93 | | 21 | | 16 |
| | 62 | | − | 30 | | 7 * | | 90 | | 9 | | 14 * |
| | 185 | | − | 13 * | | 0 * | | 80 | | 9 * | | 15 * |
| | 556 | † | − | 15 * | | 0 * | | 59 | | 0 * | | 10 * |
| | 1667 | † | − | 8 * | | 0 * | | 61 | | 0 * | | 17 * |
| | 5000 | † | − | 0 * | | 0 * | | 47 * | | 0 * | | 6 * |
| AF-2 | 0.01 | | − | — | | — | | 520 | | — | | 100 |
| | 0.1 | | − | 423 | | — | | — | | — | | — |

TABLE D-2-continued

| Test article | Dose (μg/plate) | S9 Mix | TA98 | TA1537 | TA100 | TA1535 | WP2uvrA |
|---|---|---|---|---|---|---|---|
| ICR-191 | 1.0 | − | — | 1096 | — | — | — |
| SAZ | 0.5 | − | — | — | — | 356 | — |

—: Not tested
*: Growth inhibition
†: Precipitation
DMSO: Dimethyl sulfoxide
AF-2: 2-(2-Furyl)-3-(5-nitro-2-furyl)acrylamide
ICR-191: 2-Methoxy-6-chloro-9-[3-(2-chloroethyl)aminopropylamino]acridinedihydrochloride
SAZ: Sodium azide
The number of revertant colonies shows the mean number of each plate.

TABLE E-1

| Test article | Dose (μg/plate) | | S9 Mix | TA98 | | TA1537 | | TA100 | | TA1535 | | WP2uvrA |
|---|---|---|---|---|---|---|---|---|---|---|---|---|
| DMSO | (0.1 mL) | | + | 38 | | 12 | | 130 | | 12 | | 30 |
| Metabolite E | 2.3 | | + | 56 | | 11 | | 449 | | 11 | | 23 |
| | 6.9 | | + | 61 | | 15 | | 1035 | | 14 | | 25 |
| | 21 | | + | 152 | | 26 | | 2000 | | 19 | | 25 |
| | 62 | | + | 194 | | 35 | | 2212 | | 15 | | 35 |
| | 185 | † | + | 85 | | 18 | * | 722 | * | 13 | * | 26 |
| | 556 | † | + | 56 | | 10 | * | 373 | * | 6 | * | 20 |
| | 1667 | † | + | 48 | * | 19 | * | 242 | * | 3 | * | 19 |
| | 5000 | † | + | 20 | * | 15 | | 75 | * | 3 | * | 9 |
| B[a]P | 5.0 | | + | 333 | | 92 | | 1070 | | — | | — |
| 2AA | 2.0 | | + | — | | — | | — | | 349 | | — |
| | 10.0 | | + | — | | — | | — | | — | | 643 |

—: Not tested
*: Growth inhibition
†: Precipitation
DMSO: Dimethyl sulfoxide
B[a]P: Benzo[a]pyrene
2AA: 2-Aminoanthracene
The number of revertant colonies shows the mean number of each plate.

TABLE E-2

| Test article | Dose (μg/plate) | | S9 Mix | TA98 | | TA1537 | | TA100 | | TA1535 | | WP2uvrA |
|---|---|---|---|---|---|---|---|---|---|---|---|---|
| DMSO | (0.1 mL) | | − | 21 | | 12 | | 117 | | 11 | | 20 |
| Metabolite E | 2.3 | | − | 18 | | 9 | | 130 | | 12 | | 21 |
| | 6.9 | | − | 23 | | 9 | | 127 | | 17 | | 18 |
| | 21 | | − | 18 | | 11 | | 136 | | 18 | | 18 |
| | 62 | | − | 20 | | 9 | * | 113 | | 14 | * | 20 |
| | 185 | † | − | 22 | | 4 | * | 103 | * | 14 | * | 20 |
| | 556 | † | − | 20 | | 6 | * | 88 | * | 6 | * | 17 |
| | 1667 | † | − | 17 | * | 5 | * | 79 | * | 6 | * | 13 |
| | 5000 | † | − | 3 | * | 2 | * | 55 | * | 4 | * | 8 |
| AF-2 | 0.01 | | − | — | | — | | 525 | | — | | 79 |
| | 0.1 | | − | 337 | | — | | — | | — | | — |
| ICR-191 | 1.0 | | − | — | | 1397 | | — | | — | | — |
| SAZ | 0.5 | | − | — | | — | | — | | 328 | | — |

—: Not tested
*: Growth inhibition
†: Precipitation
DMSO: Dimethyl sulfoxide
AF-2: 2-(2-Furyl)-3-(5-nitro-2-furyl)acrylamide
ICR-191: 2-Methoxy-6-chloro-9-[3-(2-chloroethyl)aminopropylamino]acridinedihydrochloride
SAZ: Sodium azide
The number of revertant colonies shows the mean number of each plate.

FORMULATION EXAMPLES

Formulation Examples of the present compound include, for example, the following formulations. The present invention, however, is not intended to be limited to these Formulation Examples.

Formulation Example 1 (Preparation of a Capsule)

| | |
|---|---|
| (1) Example 1 compound | 30 mg |
| (2) Microcrystalline cellulose | 10 mg |
| (3) Lactose | 19 mg |
| (4) Magnesium stearate | 1 mg |

Ingredients (1), (2), (3), and (4) are mixed to be filled in a gelatin capsule.

Formulation Example 2 (Preparation of a Tablet)

| | |
|---|---|
| (1) Example 1 compound | 10 g |
| (2) Lactose | 50 g |
| (3) Cornstarch | 15 g |
| (4) Carmellose calcium | 44 g |
| (5) Magnesium stearate | 1 g |

The total amounts of Ingredients (1), (2), and (3) and 30 g of Ingredient (4) are combined with water, dried in vacuo, and then granulated. The resulted granules are mixed with 14 g of Ingredient (4) and 1 g of Ingredient (5), and tableted with a tableting machine. In this manner, 1000 tablets comprising 10 mg of Example 1 compound for each tablet are obtained.

INDUSTRIAL APPLICABILITY

A compound of Formula [X] or a pharmaceutically acceptable salt thereof has an SGLT1 inhibitory activity and thus may be useful for the treatment and/or prevention of various diseases or conditions that are expected to be improved by regulating the SGLT1 activity.

The invention claimed is:

1. A compound of Formula [X]:

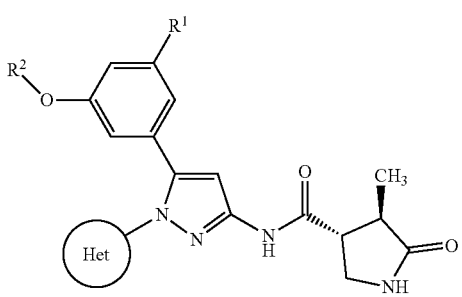

wherein $R^1$ is hydrogen or halogen;

$R^2$ is $C_{1-6}$ alkyl or halo-$C_{1-6}$ alkyl;

Ring Het is:

(1) pyridyl substituted with $R^3$; or (2) pyrazinyl, pyrimidinyl, or pyridazinyl, optionally substituted with $R^4$;

$R^3$ is cyano, halogen, or halo-$C_{1-3}$ alkyl;

$R^4$ is halogen, hydroxy, $C_{1-3}$ alkyl, halo-$C_{1-3}$ alkyl, $C_{1-3}$ alkoxy, or —N($R^5$)($R^6$); and $R^5$ and $R^6$ are each independently hydrogen or $C_{1-3}$ alkyl, or a pharmaceutically acceptable salt thereof.

2. The compound or pharmaceutically acceptable salt thereof according to claim 1, wherein $R^1$ is halogen.

3. The compound or pharmaceutically acceptable salt thereof according to claim 1, wherein $R^2$ is halo-$C_{1-6}$ alkyl.

4. The compound or pharmaceutically acceptable salt thereof according to claim 1, wherein Ring Het is pyridyl substituted with $R^3$.

5. The compound or pharmaceutically acceptable salt thereof according to claim 1, wherein Ring Het is pyrazinyl, pyrimidinyl, or pyridazinyl, optionally substituted with $R^4$.

6. A compound of Formula [I]:

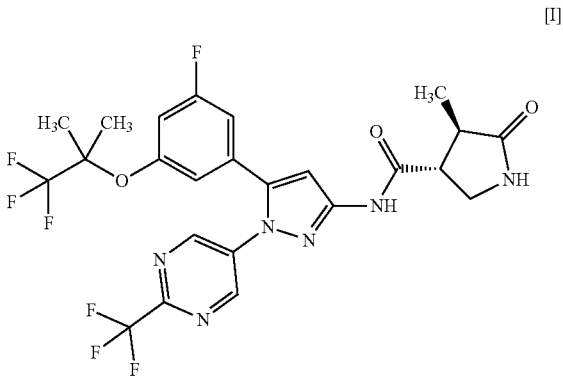 [SMILES: C[C@H]1C(=O)NC[C@@H]1C(=O)Nc1cc(-c2cc(F)cc(OC(C)(C)C(F)(F)F)c2)n(-c2cnc(C(F)(F)F)nc2)n1]

or a pharmaceutically acceptable salt thereof.

7. A compound of Formula [II]:

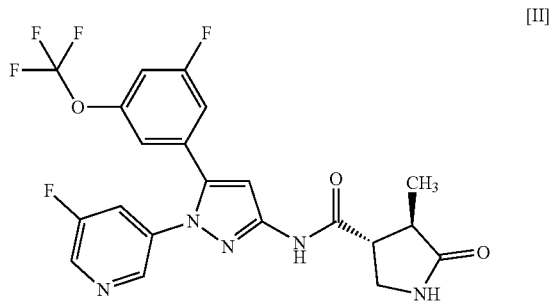 [SMILES: C[C@H]1C(=O)NC[C@@H]1C(=O)Nc1cc(-c2cc(F)cc(OC(F)(F)F)c2)n(-c2cncc(F)c2)n1]

or a pharmaceutically acceptable salt thereof.

8. A compound of Formula [III]:

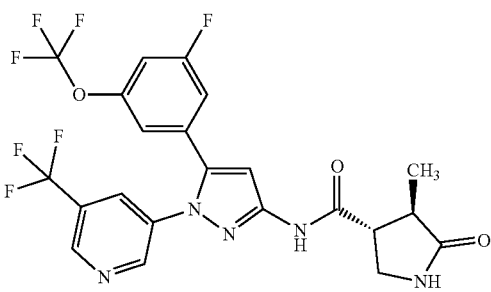

[III]

or a pharmaceutically acceptable salt thereof.

9. A compound of Formula [IV]:

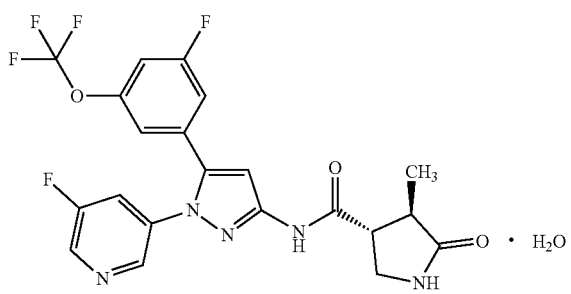

[IV]

or a pharmaceutically acceptable salt thereof.

10. A pharmaceutical composition comprising the compound or pharmaceutically acceptable salt thereof according to any one of claims 1, 7, and 9, and a pharmaceutically acceptable carrier.

11. An SGLT1 inhibitor comprising the compound or pharmaceutically acceptable salt thereof according to any one of claims 1, 7, and 9 to a mammal.

12. A method for inhibiting SGLT1 comprising administering a therapeutically effective amount of the compound or pharmaceutically acceptable salt thereof according to any one of claims 1, 7, and 9 to a mammal.

13. The method according to claim 12, wherein the diabetes is type 2 diabetes.

14. A compound of Formula [IV]:

[IV]

15. A pharmaceutical composition comprising the compound according to claim 14, and a pharmaceutically acceptable carrier.

16. A method for inhibiting SGLT1 comprising administering a therapeutically effective amount of the compound according to claim 14 to a mammal.

17. A method for treating diabetes comprising administering a therapeutically effective amount of the compound according to claim 14 to a mammal.

18. The method according to claim 17, wherein the diabetes is type 2 diabetes.

* * * * *

UNITED STATES PATENT AND TRADEMARK OFFICE
CERTIFICATE OF CORRECTION

PATENT NO. : 10,988,462 B2
APPLICATION NO. : 16/374460
DATED : April 27, 2021
INVENTOR(S) : Tomoya Miura It is certified that error appears in the above-identified patent and that said Letters Patent is hereby corrected as shown below:

In the Claims

Claim 11:
Column 100, Line 1: replace:
"An SGLT1 inhibitor comprising the compound"
With:
--A method for inhibiting SGLT1 comprising administering a therapeutically effective amount of the compound--

Claim 12:
Column 100, Line 4: replace:
"inhibiting SGLT1"
With:
--treating diabetes--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*